(12) United States Patent
Ichikawa et al.

(10) Patent No.: US 8,993,210 B2
(45) Date of Patent: *Mar. 31, 2015

(54) SALT AND PHOTORESIST COMPOSITION CONTAINING THE SAME

(75) Inventors: Koji Ichikawa, Toyonaka (JP); Hiromu Sakamoto, Ibaraki (JP)

(73) Assignee: Sumitomo Chemical Company, Limited, Tokyo (JP)

(*) Notice: Subject to any disclaimer, the term of this patent is extended or adjusted under 35 U.S.C. 154(b) by 629 days.

This patent is subject to a terminal disclaimer.

(21) Appl. No.: 13/027,575

(22) Filed: Feb. 15, 2011

(65) Prior Publication Data

US 2011/0200936 A1   Aug. 18, 2011

(30) Foreign Application Priority Data

Feb. 18, 2010 (JP) ................................. 2010-033421
Apr. 27, 2010 (JP) ................................. 2010-101850

(51) Int. Cl.

| G03F 7/004 | (2006.01) |
|---|---|
| G03F 7/38 | (2006.01) |
| C07C 303/32 | (2006.01) |
| C07C 309/06 | (2006.01) |
| C07C 309/12 | (2006.01) |
| C07C 309/19 | (2006.01) |
| C07D 303/17 | (2006.01) |
| C07D 303/40 | (2006.01) |
| C07D 305/06 | (2006.01) |
| C07D 317/72 | (2006.01) |
| C07C 381/12 | (2006.01) |
| G03F 7/039 | (2006.01) |
| C07D 303/12 | (2006.01) |

(52) U.S. Cl.
CPC ............ *C07C 381/12* (2013.01); *G03F 7/0397* (2013.01); *C07D 305/06* (2013.01); *C07C 303/32* (2013.01); *G03F 7/38* (2013.01); *G03F 7/0045* (2013.01); *C07C 309/06* (2013.01); *C07D 303/40* (2013.01); *C07C 309/19* (2013.01); *C07D 303/17* (2013.01); *C07D 317/72* (2013.01); *C07C 309/12* (2013.01); *C07D 303/12* (2013.01); *Y10S 430/122* (2013.01); *Y10S 430/123* (2013.01)
USPC ........ 430/270.1; 430/326; 430/921; 430/922; 549/341; 549/511; 549/546; 549/557; 549/558; 549/561; 549/562; 562/109; 562/111; 562/113

(58) Field of Classification Search
CPC ......... G03F 7/0045; G03F 7/039; G03F 7/38; C07C 303/32; C07C 309/06; C07C 309/12; C07C 309/19; C07D 303/17; C07D 303/40; C07D 305/06; C07D 317/72
USPC ............... 430/270.1, 921, 922, 326; 526/243; 560/15, 85; 549/78, 341, 511, 546, 549/557, 558, 561, 562; 562/36, 109, 111, 562/113
See application file for complete search history.

(56) References Cited

U.S. PATENT DOCUMENTS

| 2007/0100096 | A1 | 5/2007 | Harada et al. | |
|---|---|---|---|---|
| 2010/0203446 | A1* | 8/2010 | Ichikawa et al. | ........... 430/270.1 |
| 2010/0330497 | A1* | 12/2010 | Ichikawa et al. | ........... 430/270.1 |
| 2011/0065041 | A1* | 3/2011 | Ichikawa et al. | ........... 430/270.1 |

* cited by examiner

*Primary Examiner* — John Chu
(74) *Attorney, Agent, or Firm* — Birch, Stewart, Kolasch & Birch, LLP

(57) ABSTRACT

A salt represented by the formula (I):

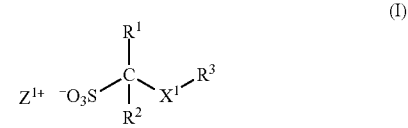

wherein $R^1$ and $R^2$ each independently represent a fluorine atom or a C1-C6 perfluoroalkyl group, $X^1$ represents a C1-C17 divalent saturated hydrocarbon group which can have one or more fluorine atoms and in which one or more —$CH_2$— can be replaced by —O— or —CO—, $R^3$ represents a group having a cyclic ether structure, and $Z^{1+}$ represents an organic cation.

10 Claims, No Drawings

SALT AND PHOTORESIST COMPOSITION CONTAINING THE SAME

This nonprovisional application claims priority under 35 U.S.C. §119(a) on Patent Application No. 2010-033421 filed in JAPAN on Feb. 18, 2010 and on Patent Application No. 2010-101850 filed in JAPAN on Apr. 27, 2010, the entire contents of which are hereby incorporated by reference.

FIELD OF THE INVENTION

The present invention relates to a salt and a photoresist composition containing the same.

BACKGROUND OF THE INVENTION

A chemically amplified positive photoresist composition used for semiconductor microfabrication employing a lithography process contains an acid generator comprising a compound generating an acid by irradiation.

US 2007/0100096 A1 discloses a salt represented by the following formula:

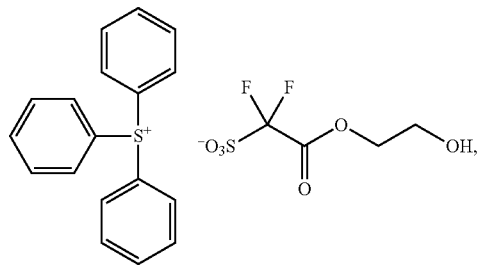

and a photoresist composition containing the same as an acid generator.

SUMMARY OF THE INVENTION

An object of the present invention is to provide a novel salt and a photoresist composition containing the same.

The present invention relates to the followings:

<1> A salt represented by the formula (I):

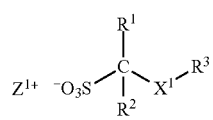

wherein $R^1$ and $R^2$ each independently represent a fluorine atom or a C1-C6 perfluoroalkyl group, $X^1$ represents a C1-C17 divalent saturated hydrocarbon group which can have one or more fluorine atoms and in which one or more —$CH_2$— can be replaced by —O— or —CO—, $R^3$ represents a group having a cyclic ether structure, and $Z^{1+}$ represents an organic cation;

<2> The salt according to <1>, wherein $R^3$ represents a group represented by the formula (IA) or (IE):

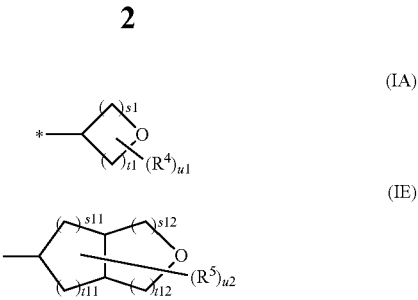

wherein $R^4$ is independently in each occurrence a C1-C12 saturated hydrocarbon group or a C6-C18 aromatic hydrocarbon group, and the saturated hydrocarbon group and the aromatic hydrocarbon group can have one or more substituents selected from the group consisting of a C1-C6 alkyl group and a nitro group, and one or more —$CH_2$— in the saturated hydrocarbon group can be replaced by —O—, u1 represents an integer of 0 to 8, s1 represents an integer of 1 to 4, t1 represents an integer of 0 to 2, with the proviso that sum of s1 and t1 is an integer of 1 to 4, $R^5$ is independently in each occurrence a hydroxyl group, a halogen atom, a C1-C6 alkyl group, a C1-C6 alkoxy group, a C1-C6 hydroxyalkyl group, a C2-C7 acyl group, a C2-C7 acyloxy group or a C2-C7 acylamino group, and two of $R^5$ can be bonded each other to form a single bond or a ring, u2 represents an integer of 0 to 16, s11 represents an integer of 1 to 4, t11 represents an integer of 0 to 2, s12 represents an integer of 1 to 4, t12 represents an integer of 0 to 2, with the proviso that sum of s12 and t12 is an integer of 1 to 4, and * represents a binding position to —$X^1$—;

<3> The salt according to <1> or <2>, wherein the salt represented by the formula (I) is a salt represented by the formula (II):

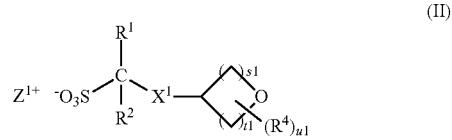

wherein $R^1$, $R^2$, $R^4$, $X^1$, s1, t1, u1 and $Z^{1+}$ are the same as defined above;

<4> The salt according to <1>, <2>, <3>, wherein X' is *—CO—O—$CH_2$— in which * represents a binding position to —$C(R^1)(R^2)$—;

<5> The salt according to any one of <1> to <4>, wherein $Z^{1+}$ is a triarylsulfonium cation;

<6> An acid generator comprising the salt according to any one of <1> to <5>;

<7> A photoresist composition comprising the acid generator according to <6> and a resin;

<8> The photoresist composition according to <7>, wherein the resin comprises a structural unit having an acid-labile group, being insoluble or poorly soluble in an aqueous alkali solution but becoming soluble in an aqueous alkali solution by the action of an acid;

<9> The photoresist composition according to <7> or <8>, which further contains a basic compound;

<10> A process for producing a photoresist pattern comprising the following steps (1) to (5):

(1) a step of applying the photoresist composition according to any one of <7> to <9> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

DESCRIPTION OF PREFERRED EMBODIMENTS

The salt of the present invention is represented by the formula (I):

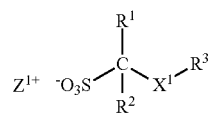
(I)

wherein $R^1$ and $R^2$ each independently represent a fluorine atom or a C1-C6 perfluoroalkyl group, $X^1$ represents a C1-C17 divalent saturated hydrocarbon group which can have one or more fluorine atoms and in which one or more —$CH_2$— can be replaced by —O— or —CO—, $R^3$ represents a group having a cyclic ether structure, and $Z^{1+}$ represents an organic cation (hereinafter, simply referred to as SALT (I)).

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $R^1$ and $R^2$ each independently preferably represent a fluorine atom or a trifluoromethyl group, and $R^1$ and $R^2$ are more preferably fluorine atoms.

Examples of the C1-C17 divalent saturated hydrocarbon group include a C1-C17 linear alkanediyl group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group; a C2-C17 branched alkanediyl group such as a 1-methyl-1,3-propylene group, a 2-methyl-1,3-propylene group, a 2-methyl-1,2-propylene group, a 1-methyl-1,4-butylene group, and a 2-methyl-1,4-butylene group; a divalent monocyclic saturated hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group; a divalent polycyclic saturated hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2,6-diyl group; and a group formed by combining two or more groups selected from the group consisting of the above-mentioned groups.

Examples of the C1-C17 divalent saturated hydrocarbon group in which one or more —$CH_2$— are replaced by —O— or —CO— include *—CO—O-$L^{b2}$-, *—CO—O-$L^{b4}$-CO—O-$L^{b3}$-, *-$L^{b5}$-O—CO—, *-$L^{b7}$-O-$L^{b6}$-, *—CO—O-$L^{b8}$-O—, and *—CO—O-$L^{b10}$-O-$L^{b9}$-CO—O—, wherein $L^{b2}$ represents a single bond or a C1-C15 saturated hydrocarbon group, $L^{b3}$ represents a single bond or a C1-C12 saturated hydrocarbon group, $L^{b4}$ represents C1-C3 saturated hydrocarbon group, with the proviso that total carbon number of $L^{b3}$ and $L^{b4}$ is 1 to 13, $L^{b5}$ represents a C1-C15 saturated hydrocarbon group, $L^{b6}$ represents a C1-C15 saturated hydrocarbon group, $L^{b7}$ represents a C1-C15 saturated hydrocarbon group, with the proviso that total carbon number of $L^{b6}$ and $L^{b7}$ is 1 to 16, $L^{b8}$ represents a C1-C14 saturated hydrocarbon group, $L^{b9}$ represents a C1-C11 saturated hydrocarbon group, $L^{b10}$ represents a C1-C11 saturated hydrocarbon group, with the proviso that total carbon number of $L^{b9}$ and $L^{b10}$ is 1 to 12, and * represents a binding position to —$C(R^1)(R^2)$—. Among them, preferred is *—CO—O-$L^{b2}$-, and more preferred is *—CO—O-$L^{b2}$- in which $L^{b2}$ is a single bond or —$CH_2$—.

Examples of *—CO—O-$L^{b2}$- include *—CO—O— and *—CO—O—$CH_2$—. Examples of *—CO—O-$L^{b4}$-CO—O-$L^{b3}$- include *—CO—O—$CH_2$—CO—O—, *—CO—O—$(CH_2)_2$—CO—, *—CO—O—$(CH_2)_3$—CO—O—, *—CO—O—$(CH_2)_4$—CO—O—, *—CO—O—$(CH_2)_6$—CO—O—, *—CO—O—$(CH_2)_8$—CO—O—, *—CO—O—$CH_2$—CH$(CH_3)$—CO—O— and *—CO—O—$CH_2$—$C(CH_3)_2$—CO—O—. Examples of *-$L^{b5}$-O—CO— include *—$CH_2$—O—CO—, *—$(CH_2)_2$—O—CO—, *—$(CH_2)_3$—O—CO—, *—$(CH_2)_4$—O—CO—, *—$(CH_2)_6$—O—CO— and *—$(CH_2)_8$—O—CO—. Examples of *-$L^{b7}$-O-$L^{b6}$- include *—$CH_2$—O—$CH_2$—. Examples of *—CO—O-$L^{b8}$-O— include *—CO—O—$CH_2$—O—, *—CO—O—$(CH_2)_2$—O—, *—CO—O—$(CH_2)_3$—O—, *—CO—O—$(CH_2)_4$—O— and *—CO—O—$(CH_2)_6$—O—. Examples of *—CO—O-$L^{b10}$-O-$L^{b9}$-CO—O— include the followings.

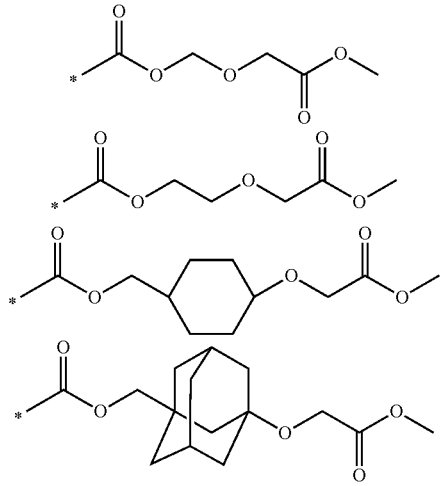

The saturated hydrocarbon group can have one or more fluorine atoms.

$R^3$ represents a group having a cyclic ether structure, and a C2-C5 cyclic ether structure is preferable as the cyclic ether structure.

Examples of the cyclic ether structure include a structure containing an oxirane ring, a structure containing an oxetane ring, a structure containing a five-membered cyclic ether structure having 4 carbon atoms, and a structure containing a six-membered cyclic ether structure having 5 carbon atoms, and among them, preferred are a structure containing an oxirane ring and a structure containing an oxetane ring, and more preferred is a structure containing an oxirane ring.

Preferable examples of the group containing the cyclic ether structure include the group containing the groups represented by the formulae (IA) and (IE):

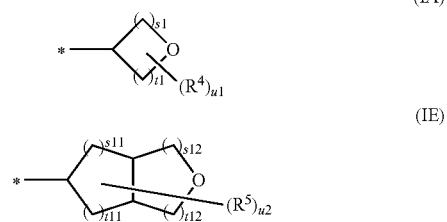

wherein $R^4$ is independently in each occurrence a C1-C12 saturated hydrocarbon group or a C6-C18 aromatic hydrocarbon group, and the saturated hydrocarbon group and the aromatic hydrocarbon group can have one or more substituents selected from the group consisting of a C1-C6 alkyl group and a nitro group, and one or more —$CH_2$— in the saturated hydrocarbon group can be replaced by —O—, u1 represents an integer of 0 to 8, s1 represents an integer of 1 to 4, t1 represents an integer of 0 to 2, with the proviso that sum of s1 and t1 is an integer of 1 to 4, $R^5$ is independently in each occurrence a hydroxyl group, a halogen atom, a C1-C6 alkyl group, a C1-C6 alkoxy group, a C1-C6 hydroxyalkyl group, a C2-C7 acyl group, a C2-C7 acyloxy group or a C2-C7 acylamino group, and two of $R^5$ can be bonded each other to form a single bond or a ring, u2 represents an integer of 0 to 16, s11 represents an integer of 1 to 4, t11 represents an integer of 0 to 2, s12 represents an integer of 1 to 4, t12 represents an integer of 0 to 2, with the proviso that sum of s12 and t12 is an integer of 1 to 4, and * represents a binding position to the neighboring atom.

Examples of the C1-C12 saturated hydrocarbon group include a C1-C12 alkyl group such as a methyl group, an ethyl group, a propyl group, an isopropyl group, a butyl group, a pentyl group, a hexyl group, a heptyl group and a decyl group, and a C3-C12 monocyclic or polycyclic saturated hydrocarbon group such as a cyclohexyl group, an adamantyl group. Examples of the C6-C18 aromatic hydrocarbon group include a phenyl group. Examples of the substituted aromatic group include a tolyl group and a nitrophenyl group. Examples of the C1-C12 saturated hydrocarbon group in which one or more —$CH_2$— are replaced by —O— include $CH_3$—O—$CH_2$O$H_2$—O—$CH_2CH_2$— and the following.

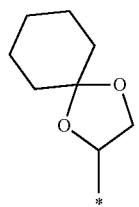

Examples of the halogen atom include a bromine atom and a chlorine atom, and examples of the C1-C4 alkyl group include a methyl group, an ethyl group, a propyl group, an isopropyl group and a butyl group. Examples of the C1-C4 alkoxy group include a methoxy group, an ethoxy group, a propoxy group, an isopropoxy group and a butoxy group. Examples of the C1-C6 hydroxyalkyl group include a hydroxymethyl group and a 2-hydroxyethyl group, and examples of the C2-C7 acyl group include an acetyl group, a propionyl group and a benzoyl group. Examples of the C2-C7 acyloxy group include an acetyloxy group, a propionyloxy group and a benzoyloxy group, and examples of the C2-C7 acylamino group include an acetylamino group, a propionylamino group and a benzoylamino group.

In the formula (IA), u is preferably 0 or 1, and in the formula (IE), u2 is preferably an integer of 0 to 3.

In the formula (IA), s1 is preferably 1, and t1 is preferably 0 or 1, and sum of s1 and t1 is preferably 1 or 2. In the formula (IE), sum of s12 and t12 is preferably 1 or 2.

Examples of the group represented by the formula (IA) include the groups represented by the formulae (IC):

wherein s3 and s4 independently represent 0 or 1, with the proviso that sum of s3 and s4 is 1 or 2, and * represents a binding position to the neighboring atom.

The group containing the cyclic ether structure may be divalent group, and examples thereof include a group containing the group represented by the formula (ID):

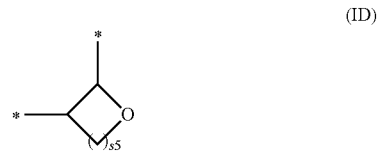

wherein s5 represents 0 or 1 and * represents a binding position to the neighboring atom.

Examples of the group represented by the formula (IA) include the following.

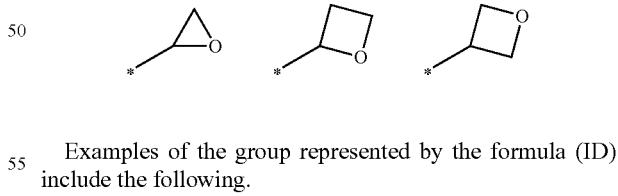

Examples of the group represented by the formula (ID) include the following.

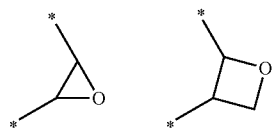

Examples of the group represented by the formula (IE) include the following.

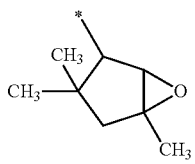 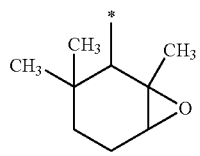
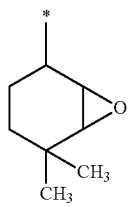 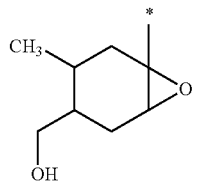
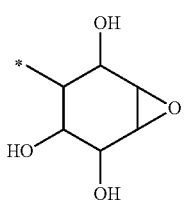 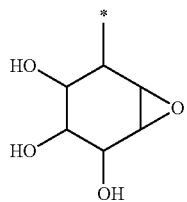
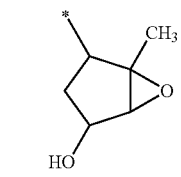 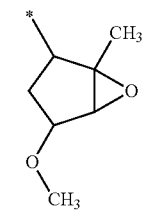
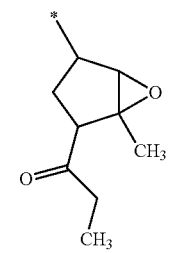 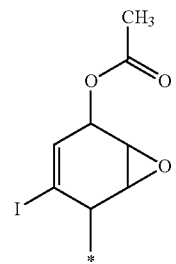
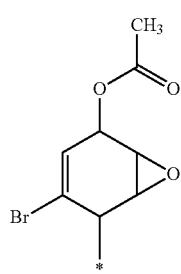 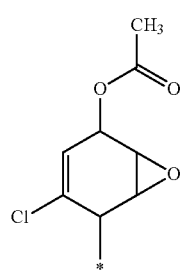
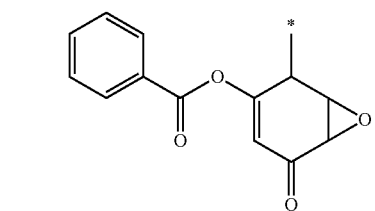 [SMILES: CC1C(NC(=O)c2ccccc2)=CC(=O)C2OC12]
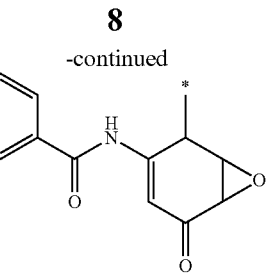
Examples of the cyclic ether structure include the following.
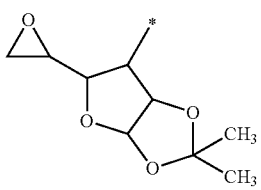
Examples of $R^3$ include the following.
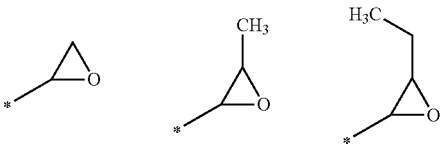
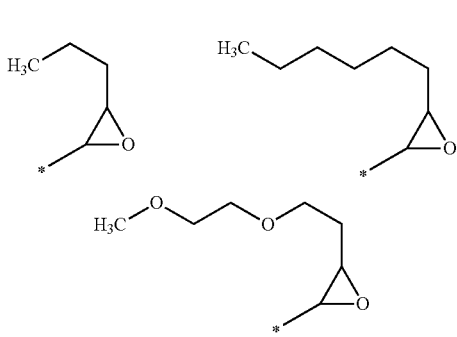
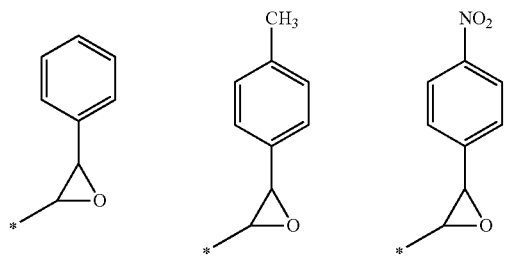
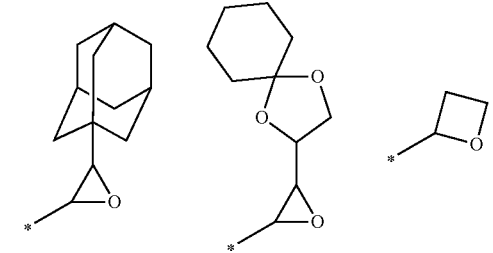

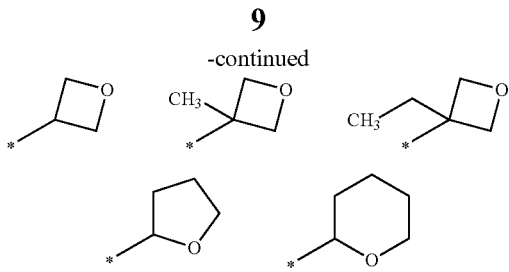
SALT (I) is preferably a salt represented by the formula (II):
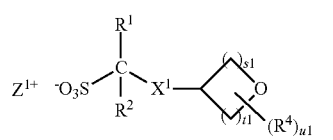 (II)
wherein $R^1$, $R^2$, $R^4$, $X^1$, s1, t1, u1 and $Z^{1+}$ are the same as defined above.
SALT (I) is also preferably a salt represented by the formula (III):
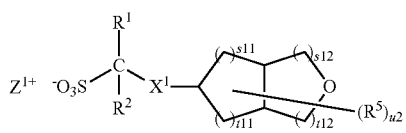 (III)
wherein $R^1$, $R^2$, $R^5$, $X^1$, s11, t11, s12, t12, u2 and $Z^{1+}$ are the same as defined above.
Examples of SALT (I) include the following.
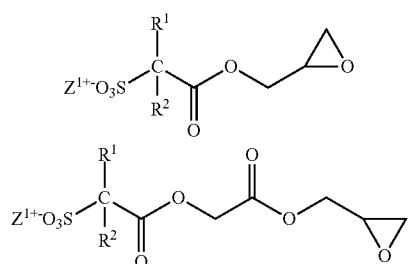
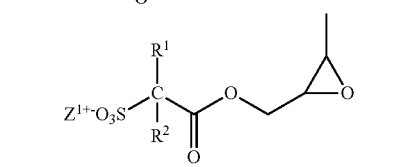
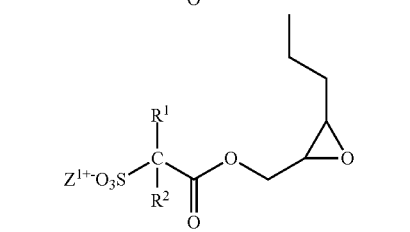
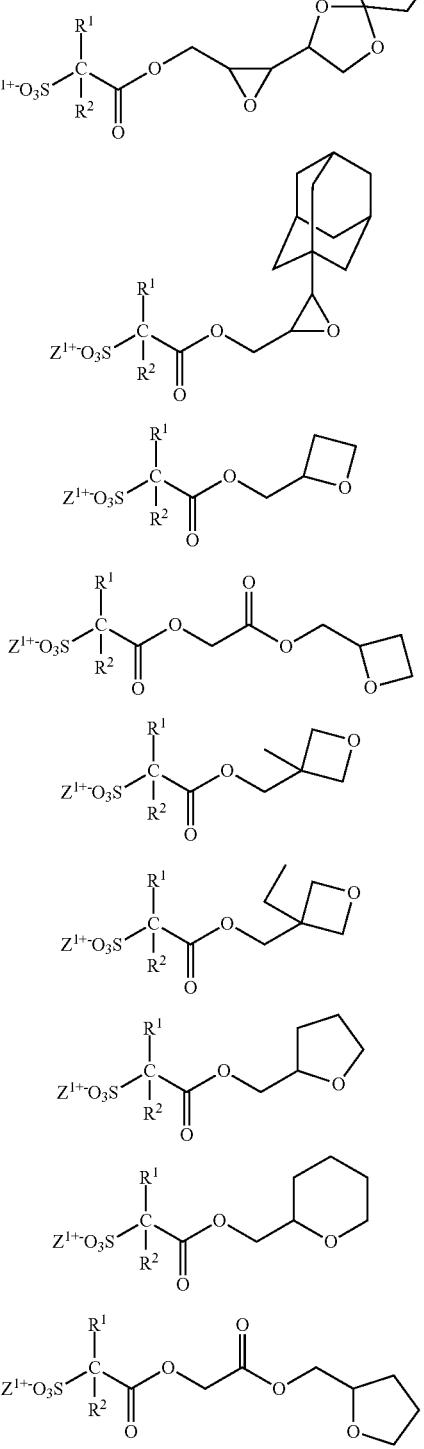

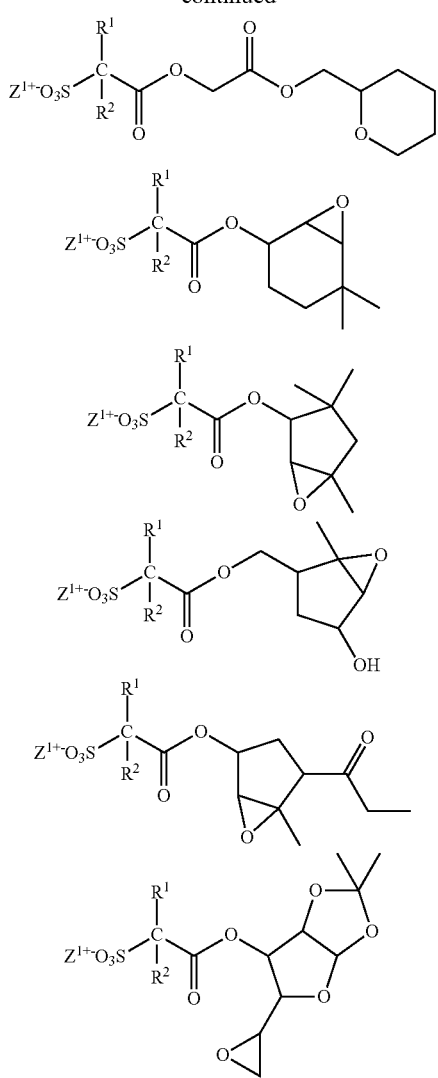

Examples of the organic cation represented by $Z^{1+}$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable, and triarylsulfonium cation is especially preferable.

Preferable examples of the organic cation represented by $Z^{1+}$ include the cations represented by the formulae (b2-1) to (b2-4):

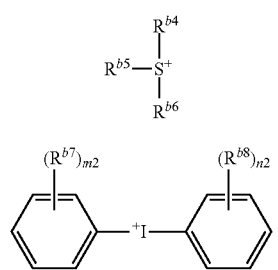

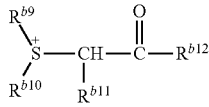

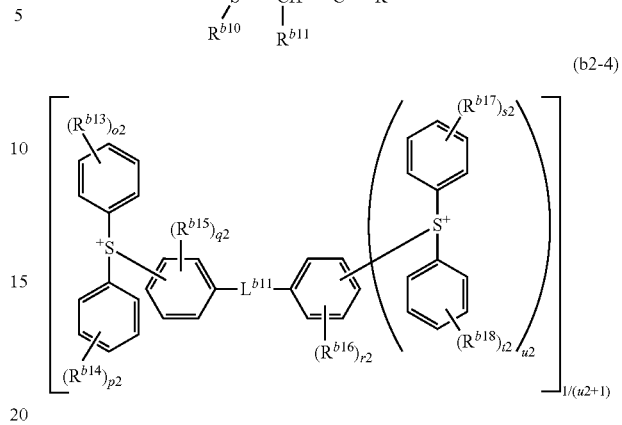

wherein $R^{b4}$, $R^{b5}$ and $R^{b6}$ independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C18 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 aliphatic hydrocarbon group, a C3-C18 saturated cyclic hydrocarbon group and a C1-C12 alkoxy group, $R^{b7}$ and $R^{b8}$ are independently in each occurrence a hydroxyl group, a C1-C12 aliphatic hydrocarbon group or a C1-C12 alkoxy group, m2 and n2 independently represents an integer of 0 to 5, $R^{b9}$ and $R^{b10}$ independently represent a C1-C18 aliphatic hydrocarbon group or a C3-C18 saturated cyclic hydrocarbon group, or $R^{b9}$ and $R^{b10}$ are bonded to form a C2-C11 divalent acyclic hydrocarbon group which forms a ring together with the adjacent $S^+$, and one or more —CH$_2$— in the divalent acyclic hydrocarbon group may be replaced by —CO—, —O— or —S—, and $R^{b11}$ represents a hydrogen atom, a C1-C18 aliphatic hydrocarbon group, a C3-C18 saturated cyclic hydrocarbon group or a C6-C18 aromatic hydrocarbon group, $R^{b12}$ represents a C1-C12 aliphatic hydrocarbon group, a C3-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and a C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —CH$_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ independently represent a hydroxyl group, a C1-C12 aliphatic hydrocarbon group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 18 carbon atoms and more preferably 4 to 12 carbon atoms.

Preferable examples of the aliphatic hydrocarbon group include an alkyl group such as a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group include a cyclopropyl group, a cyclobutyl group, a cyclopentyl group, a cyclohexyl group, a cycloheptyl group, a cyclodecyl group, a 2-alkyl-a-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b12}$ include a trimethylene group, a tetramethylene group and a pentamethylene group. Examples of the ring group formed together with the adjacent S+ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

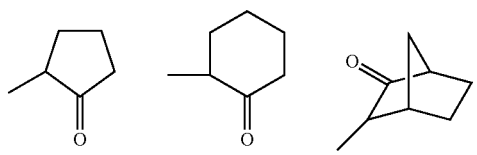

A C1-C5 divalent acyclic hydrocarbon group is preferable.

Among the above-mentioned cations, preferred is the cation represented by the formula (b2-1), and more preferred is the cation represented by the formula (b2-1-1). A triphenylsulfonium cation is especially preferable.

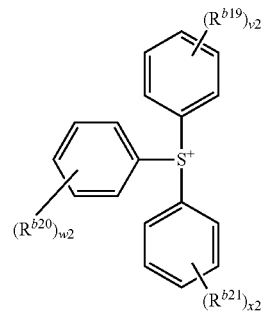

(b2-1-1)

wherein $R^{b19}$, $R^{b20}$ and $R^{b21}$ are independently in each occurrence a halogen atom (preferably a fluorine atom), a hydroxyl group, a C1-C18 aliphatic hydrocarbon group, a C3-C18 saturated cyclic hydrocarbon group or a C1-C12 alkoxy group, and one or more hydrogen atoms of the aliphatic hydrocarbon group can be replaced by a hydroxyl group, a C1-C12 alkoxy group or a C6-C18 aromatic hydrocarbon group, and one or more hydrogen atoms of the saturated cyclic hydrocarbon group can be replaced by a halogen atom, a glycidyloxy group or a C2-C4 acyl group, and v2, w2 and x2 independently each represent an integer of 0 to 5.

The aliphatic hydrocarbon group has preferably 1 to 12 carbon atoms, and the saturated cyclic hydrocarbon group has preferably 4 to 18 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the cation represented by the formula (b2-1) include the following.

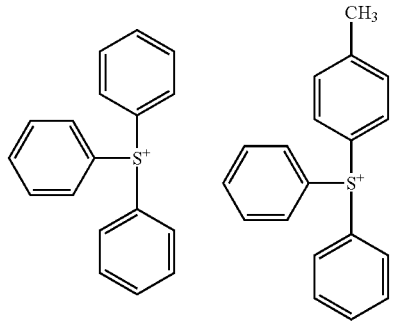

-continued
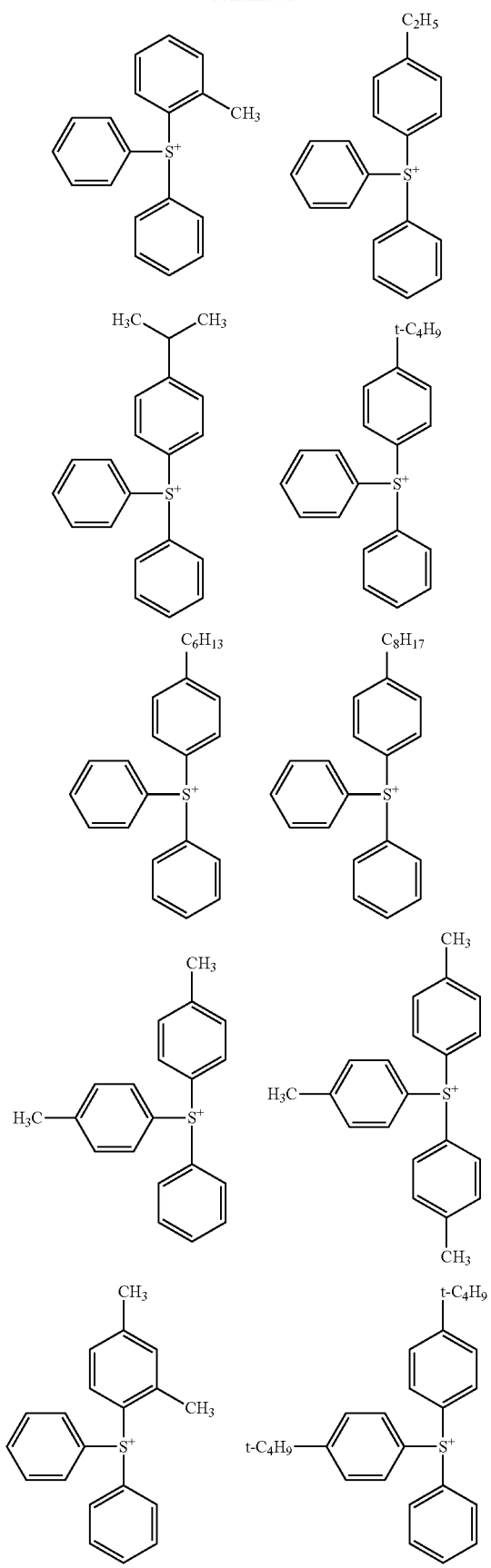
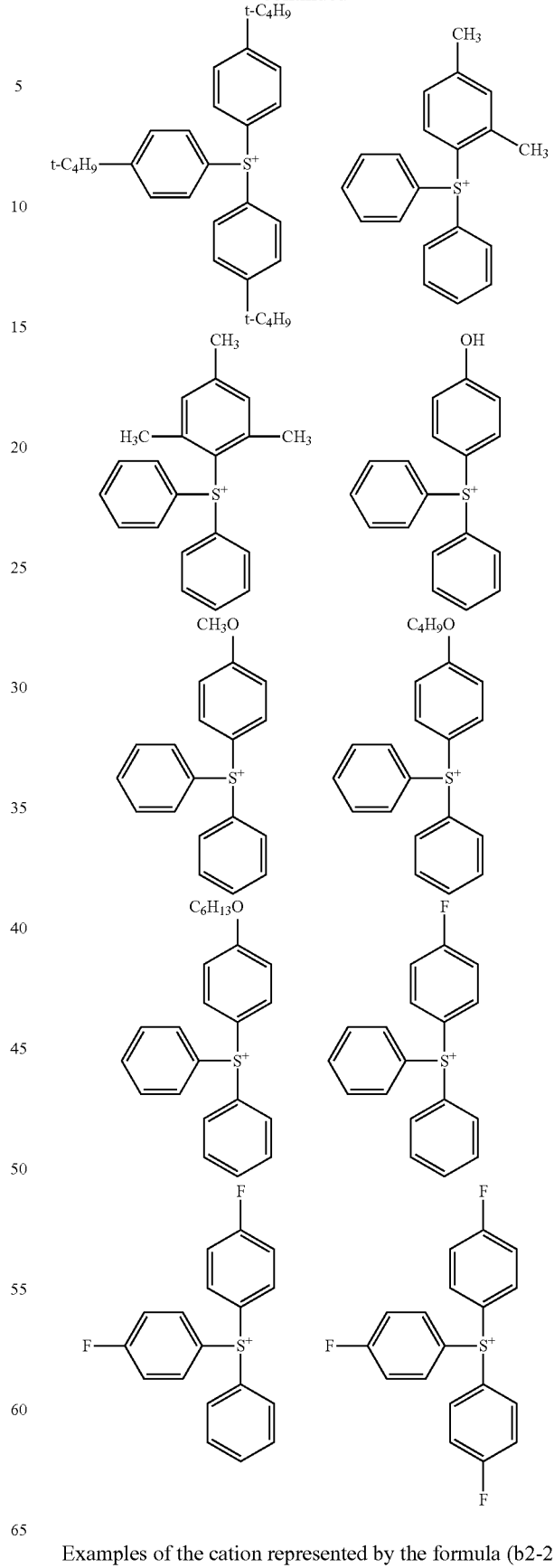
Examples of the cation represented by the formula (b2-2) include the followings.

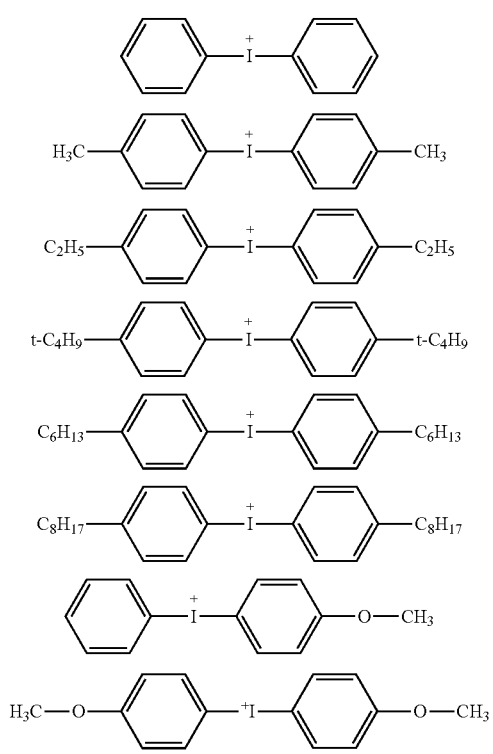
Examples of the cation represented by the formula (b2-3) include the followings.
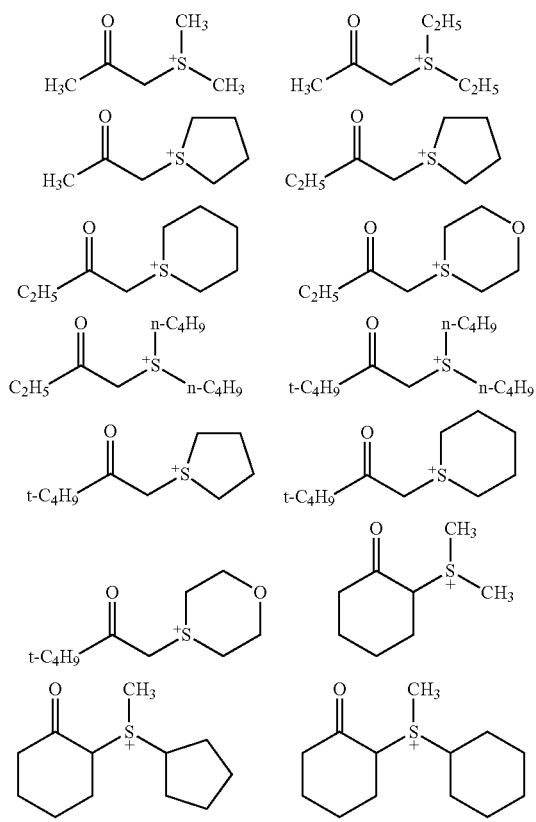
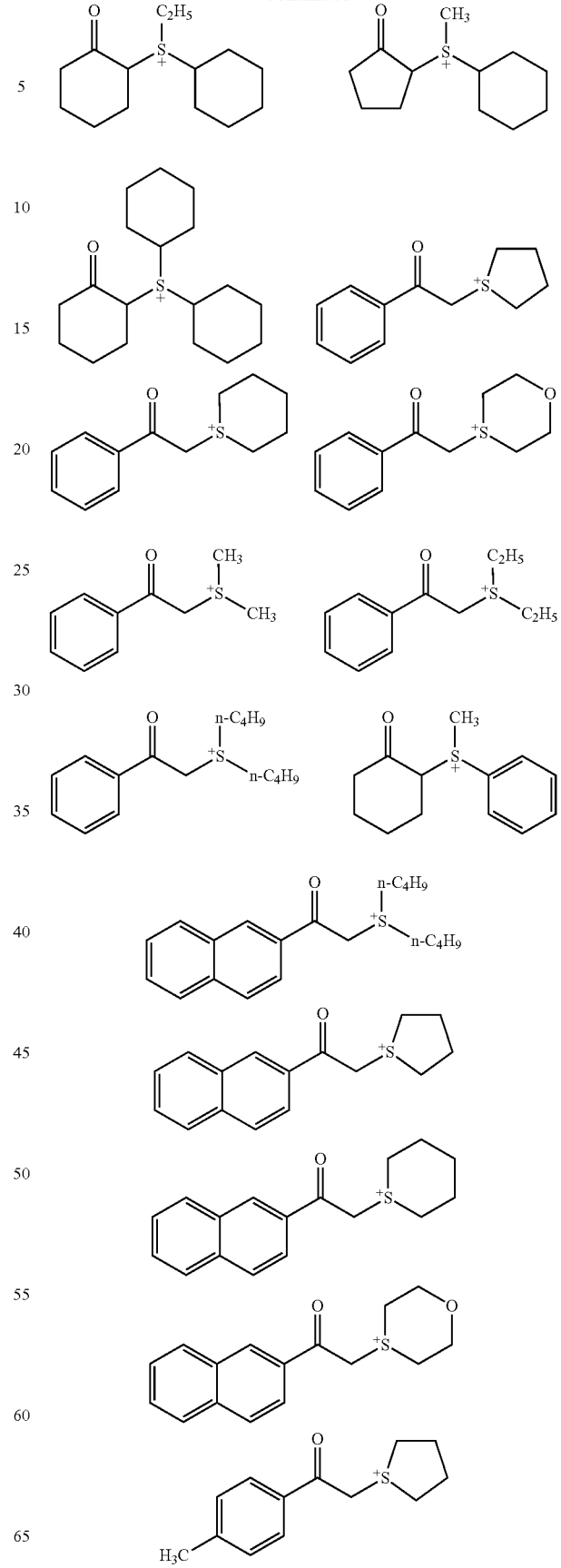

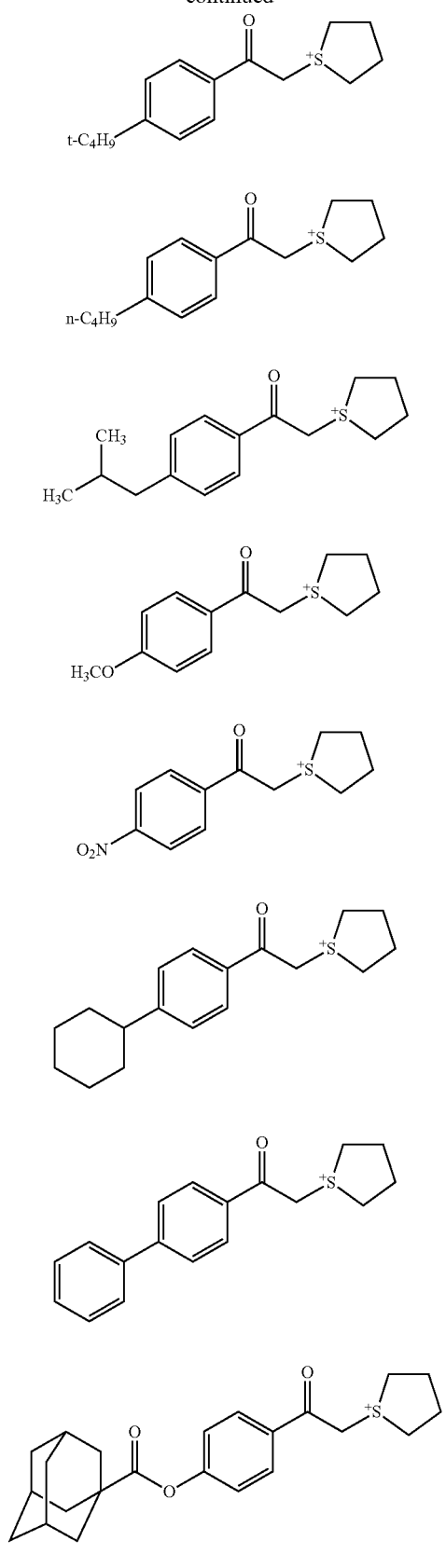
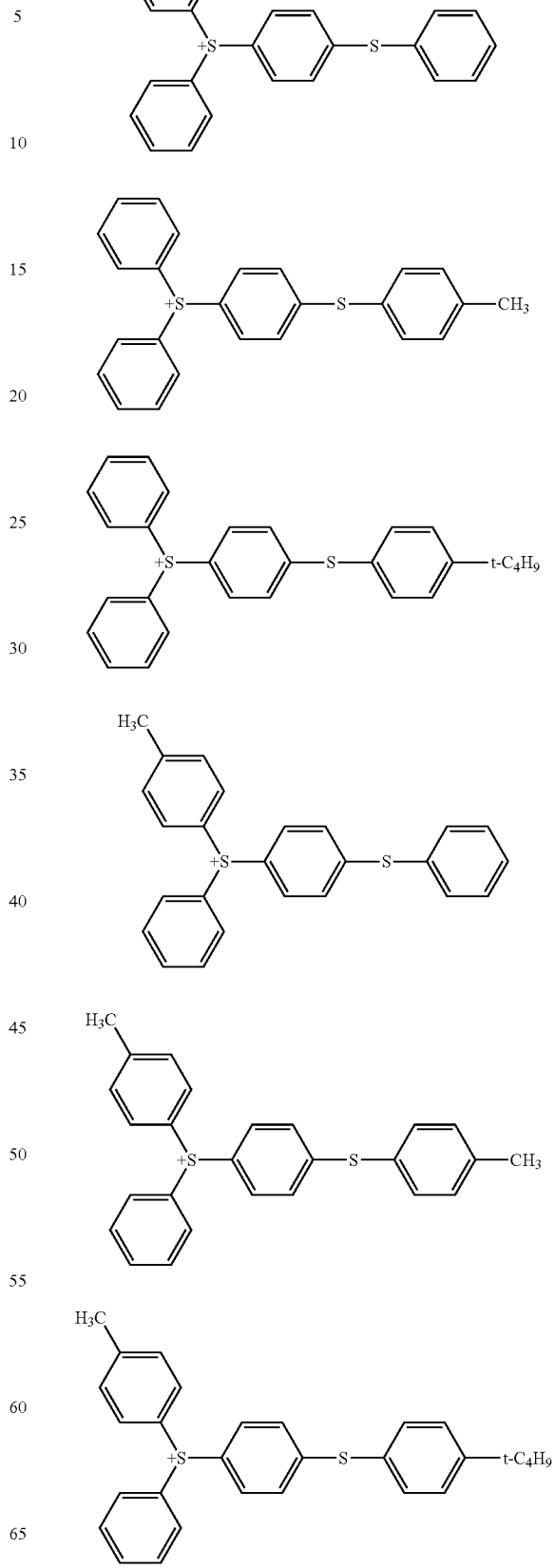
Examples of the cation represented by the formula (b2-4) include the followings.

-continued
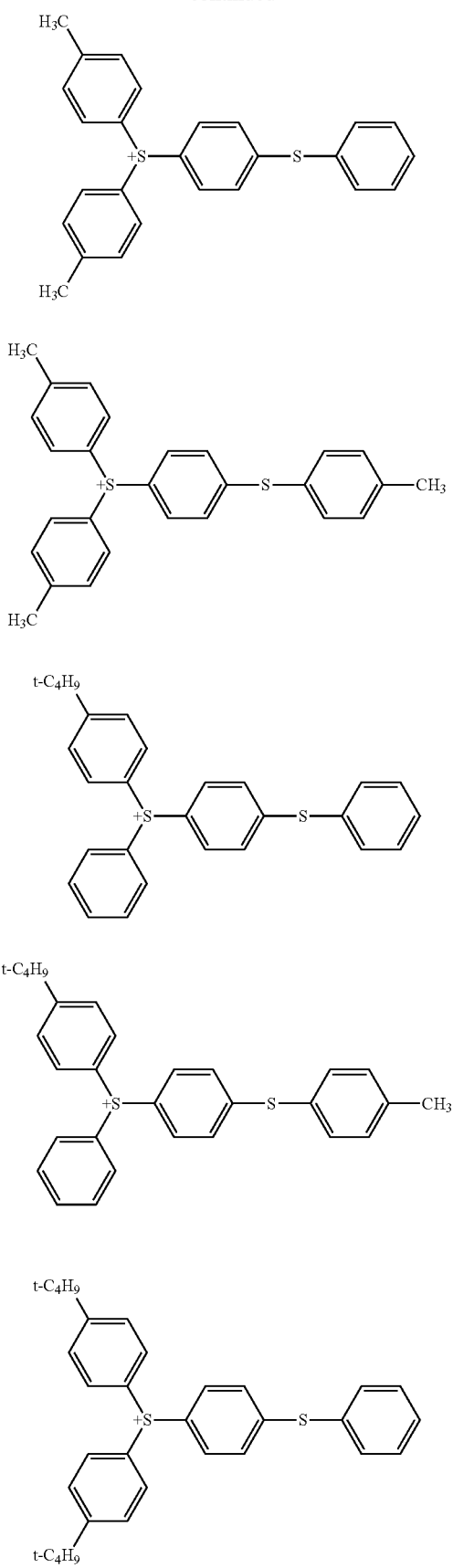
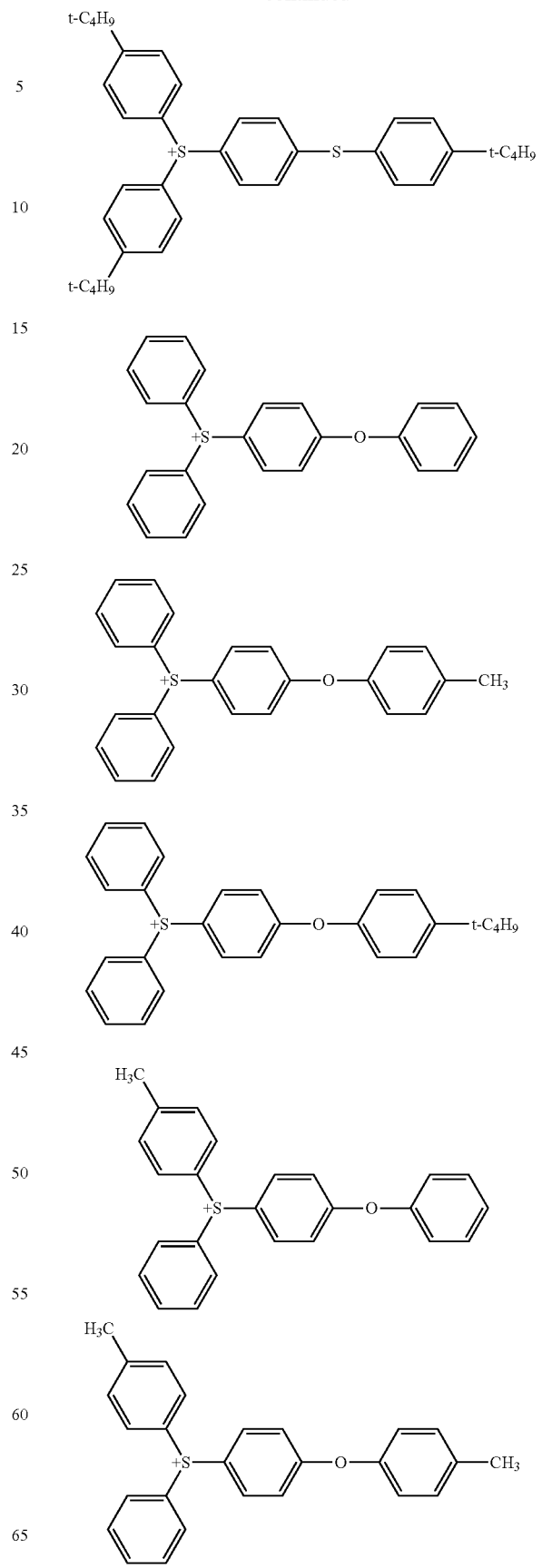

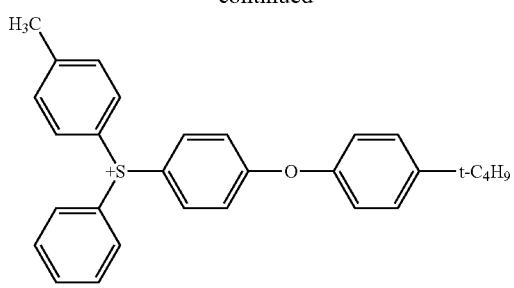
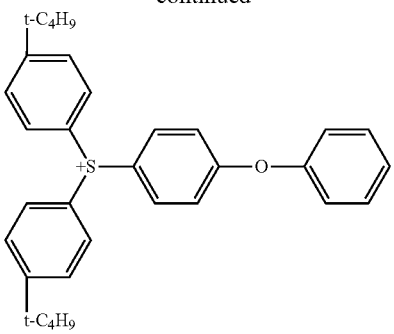
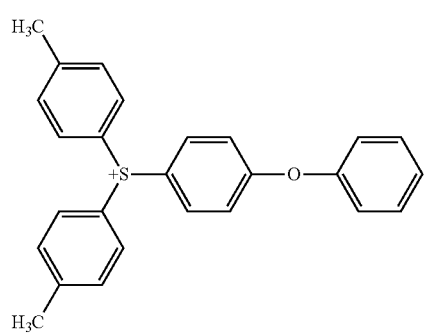
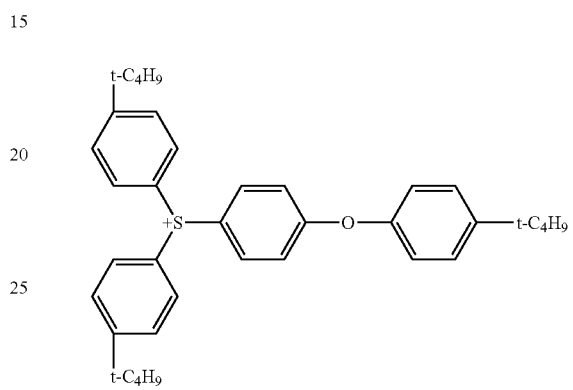
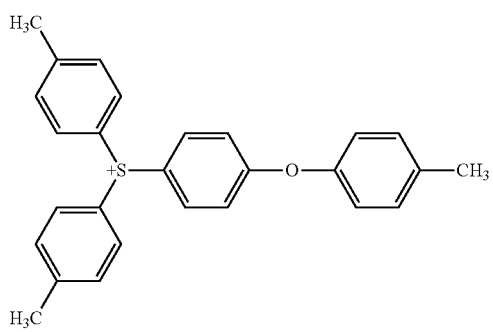
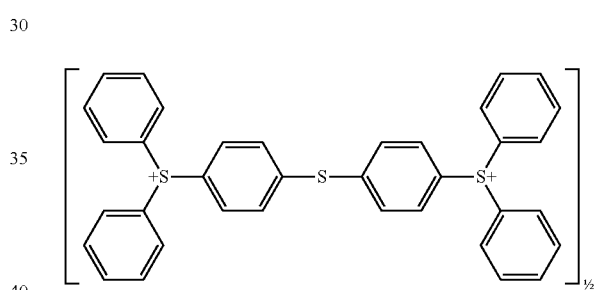
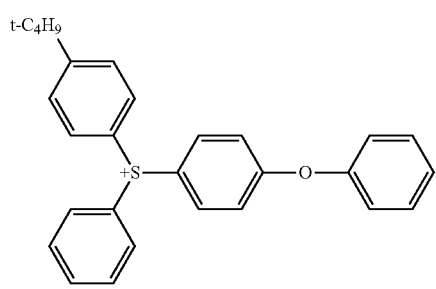
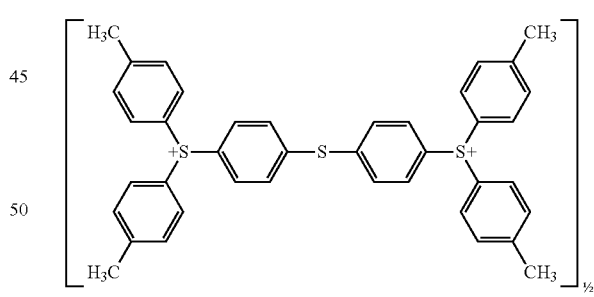
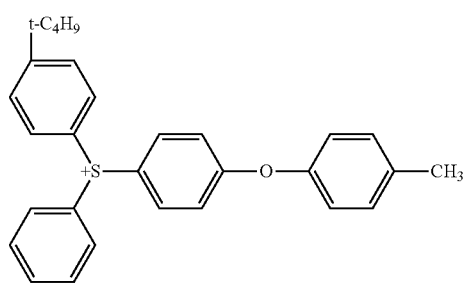
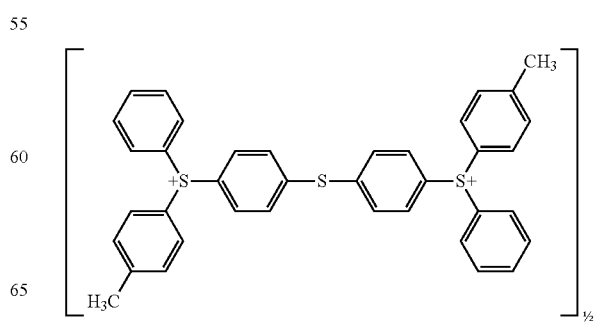

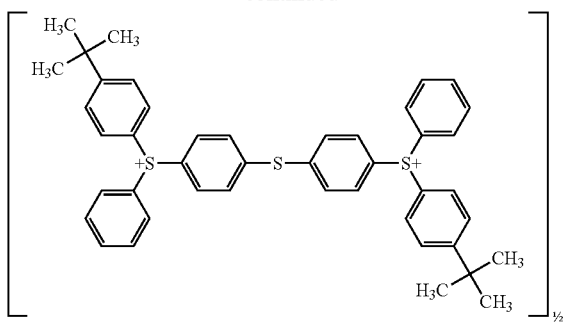
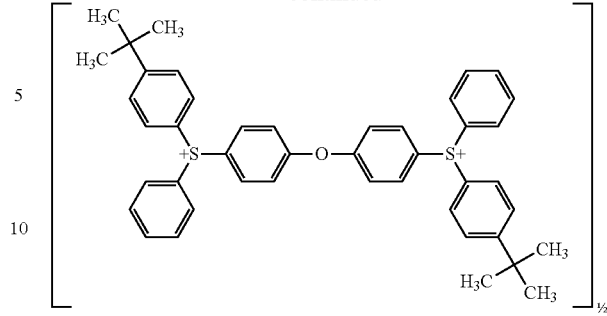
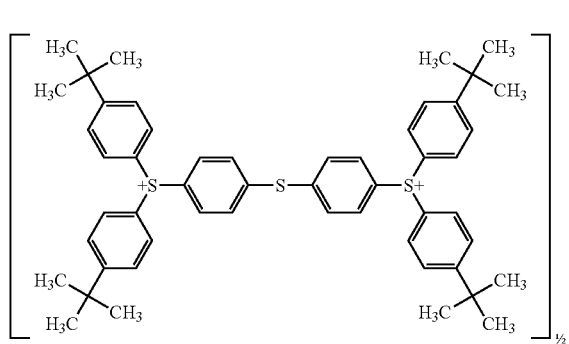
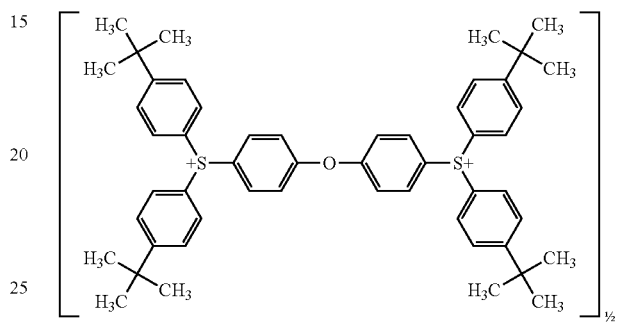
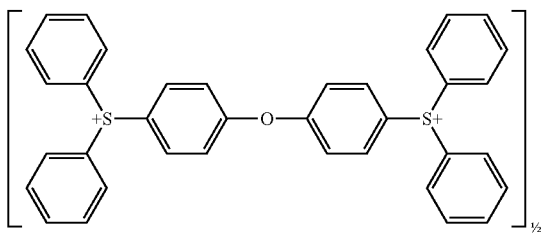
Examples of SALT (I) include a salt wherein the anion is any one of the above-mentioned anions and the cation is any one of organic cations. Preferable examples of SALT (I) include the following.
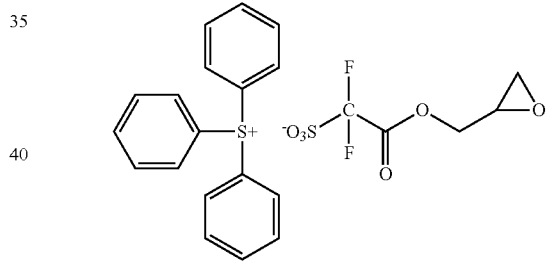
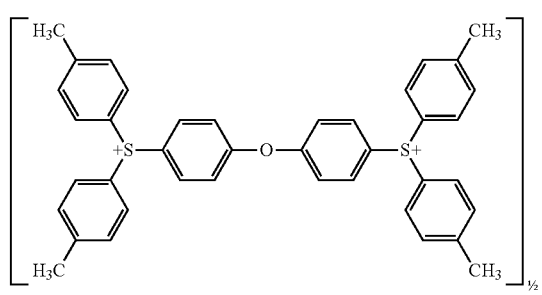
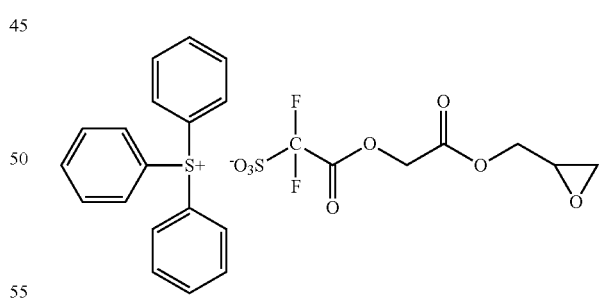
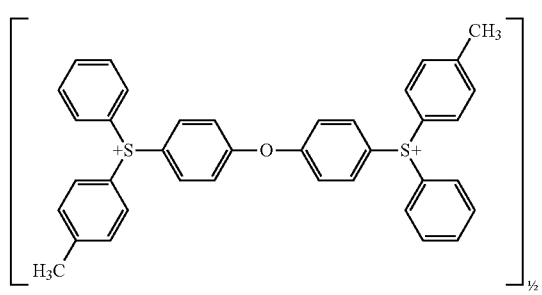
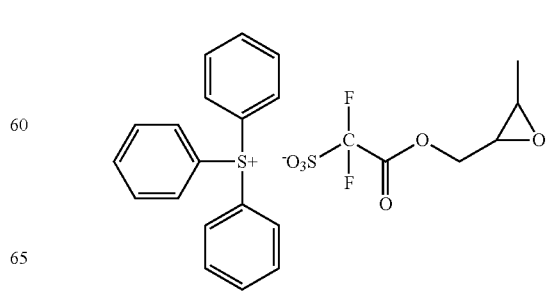

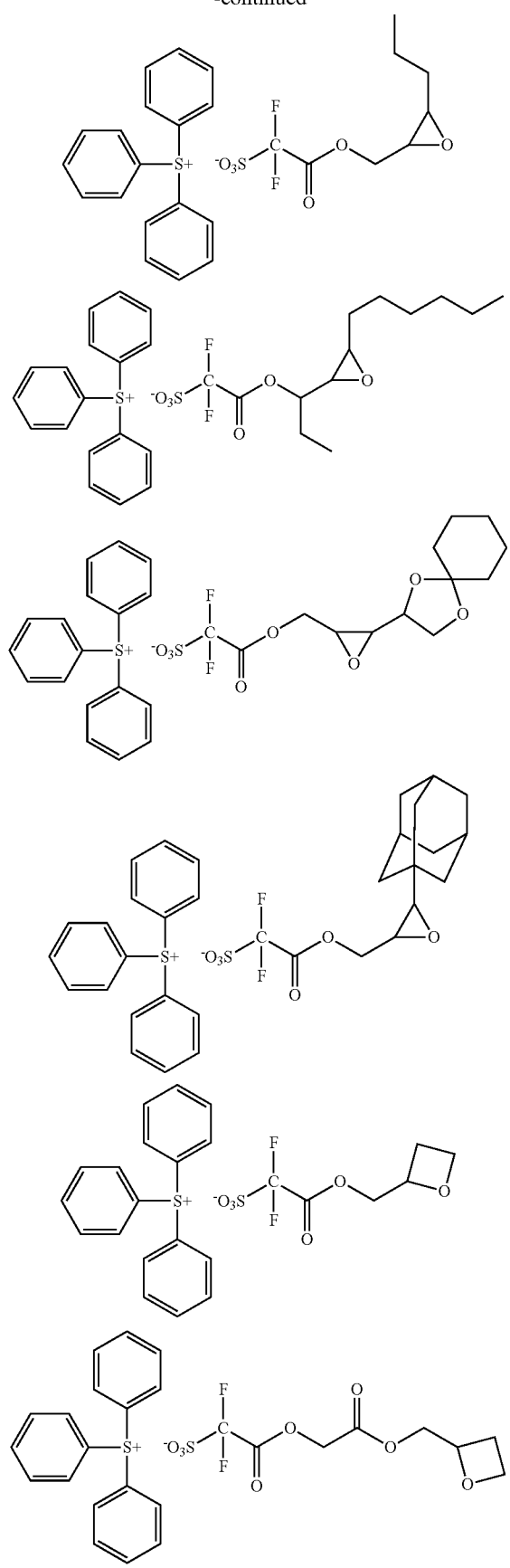
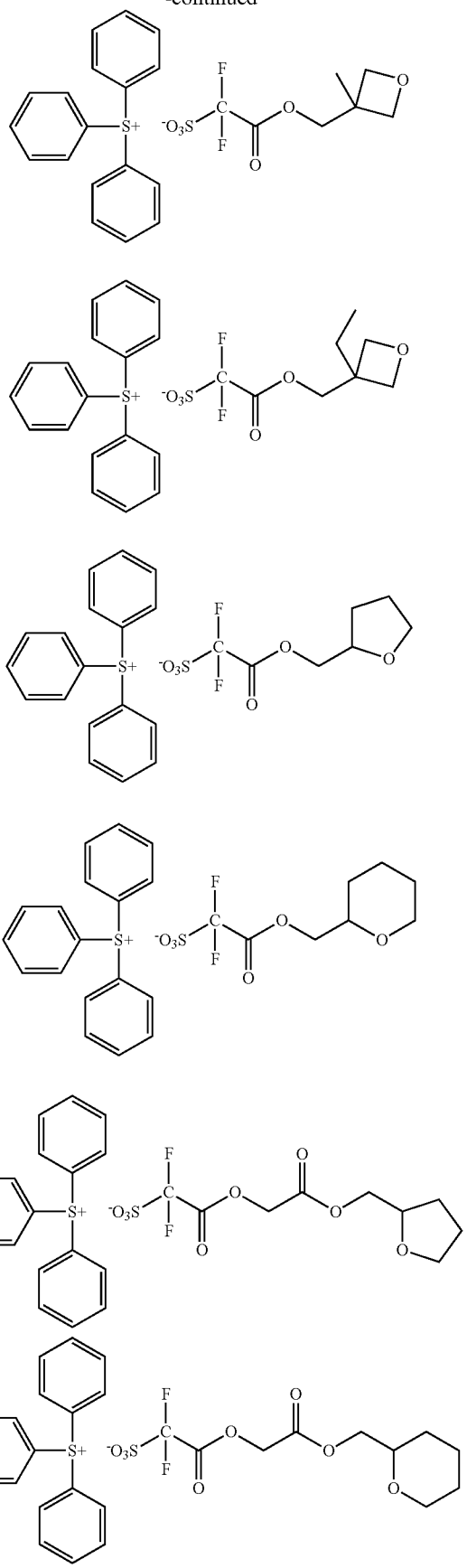

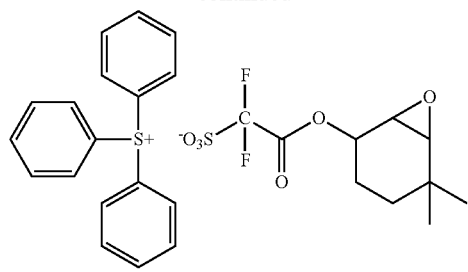
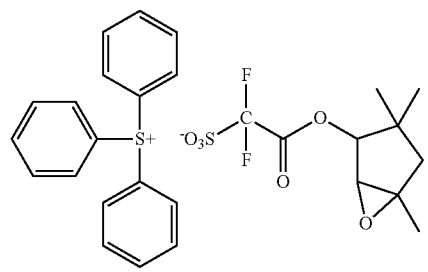
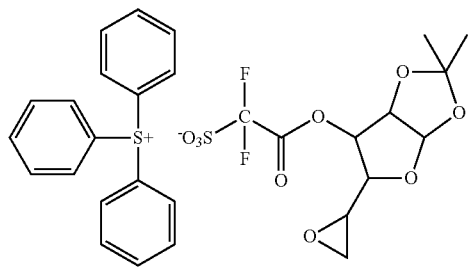
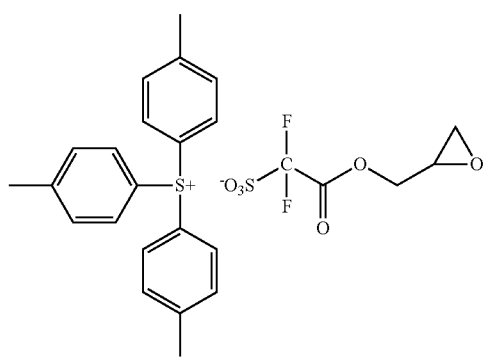
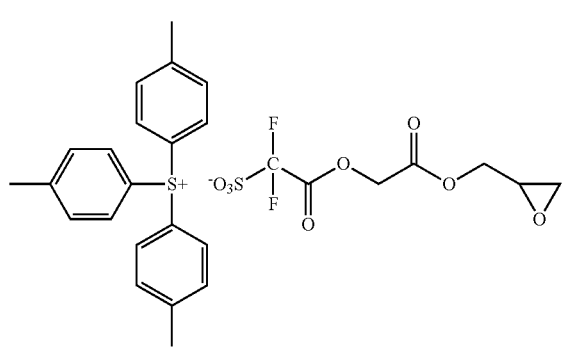
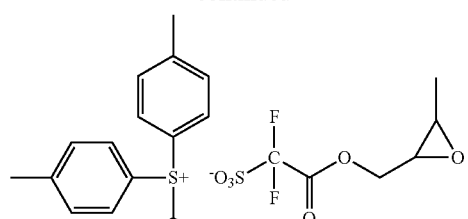
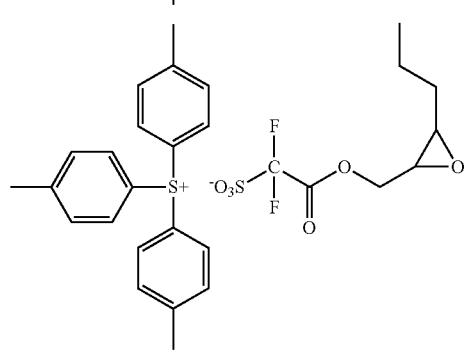
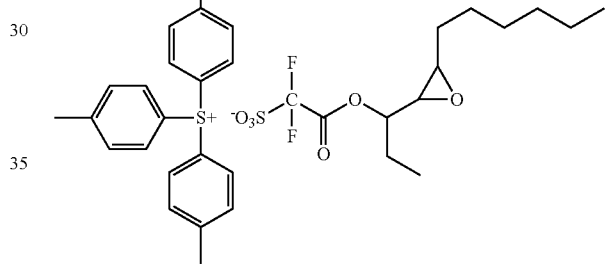
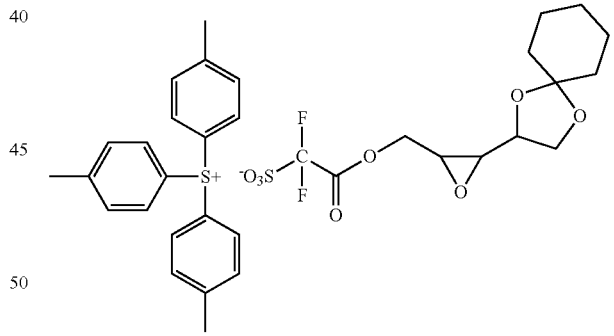
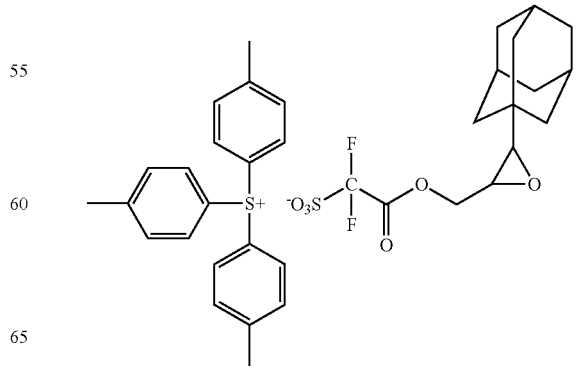

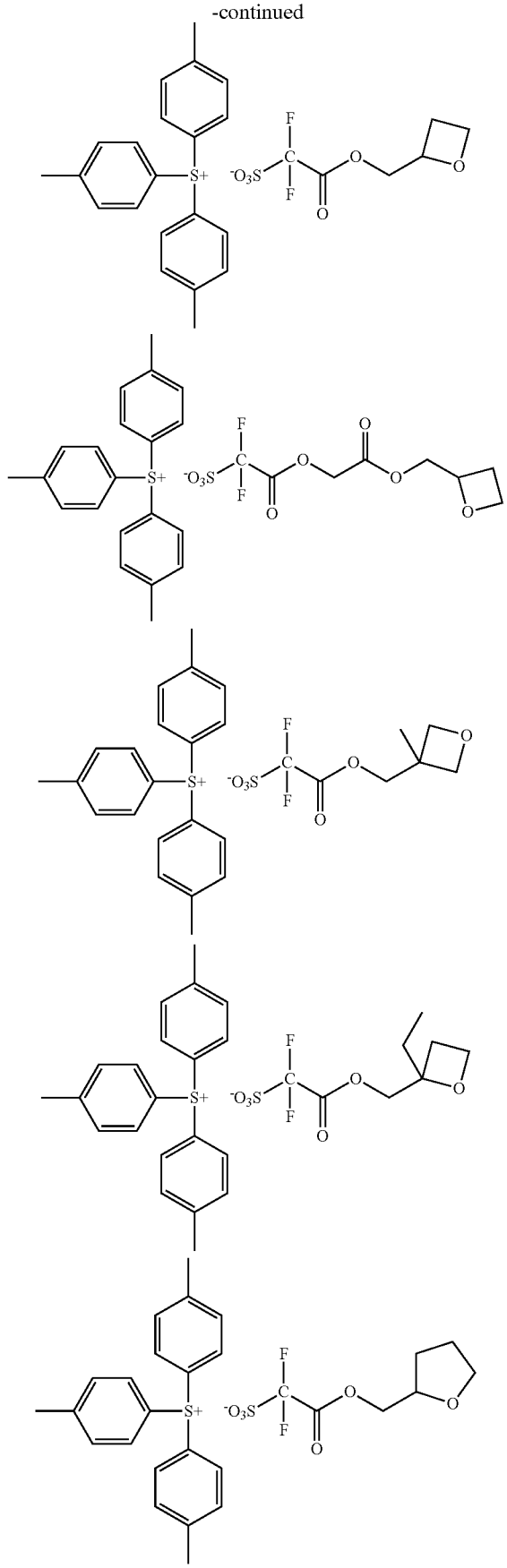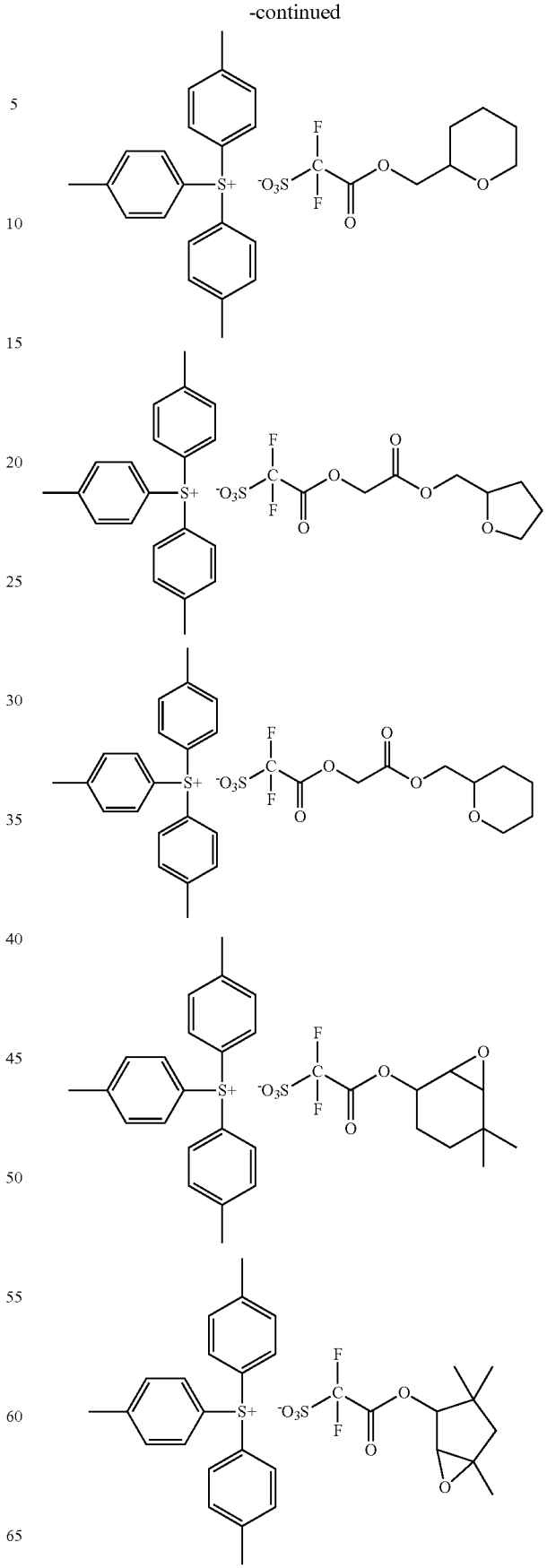

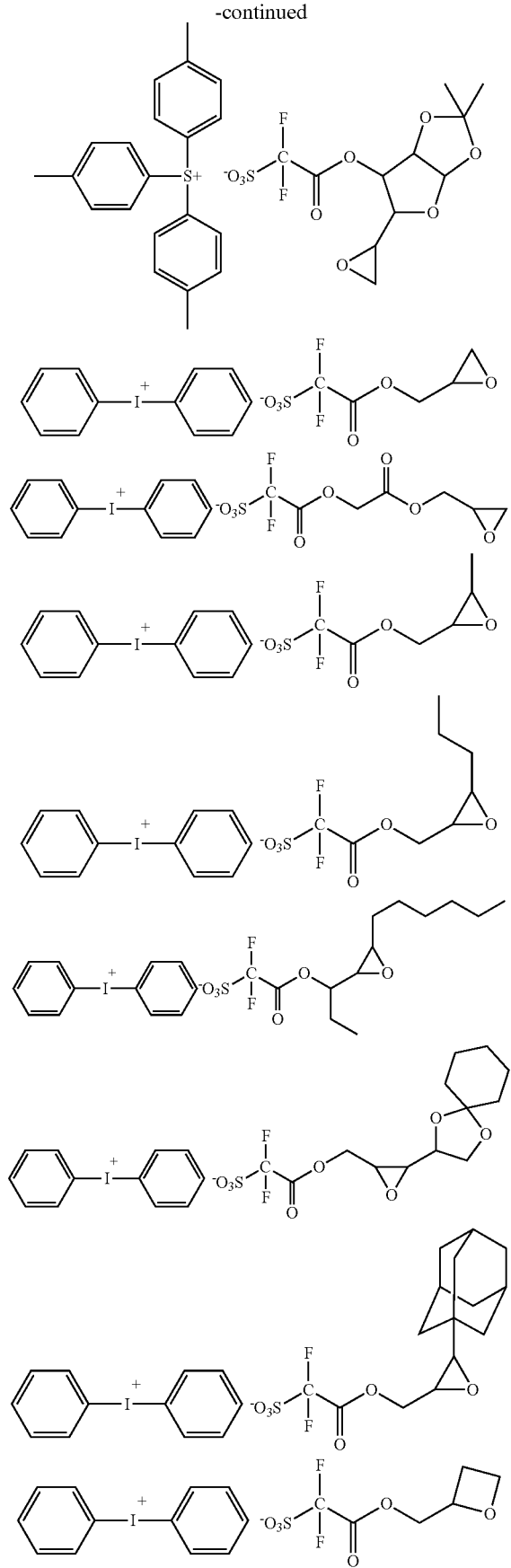
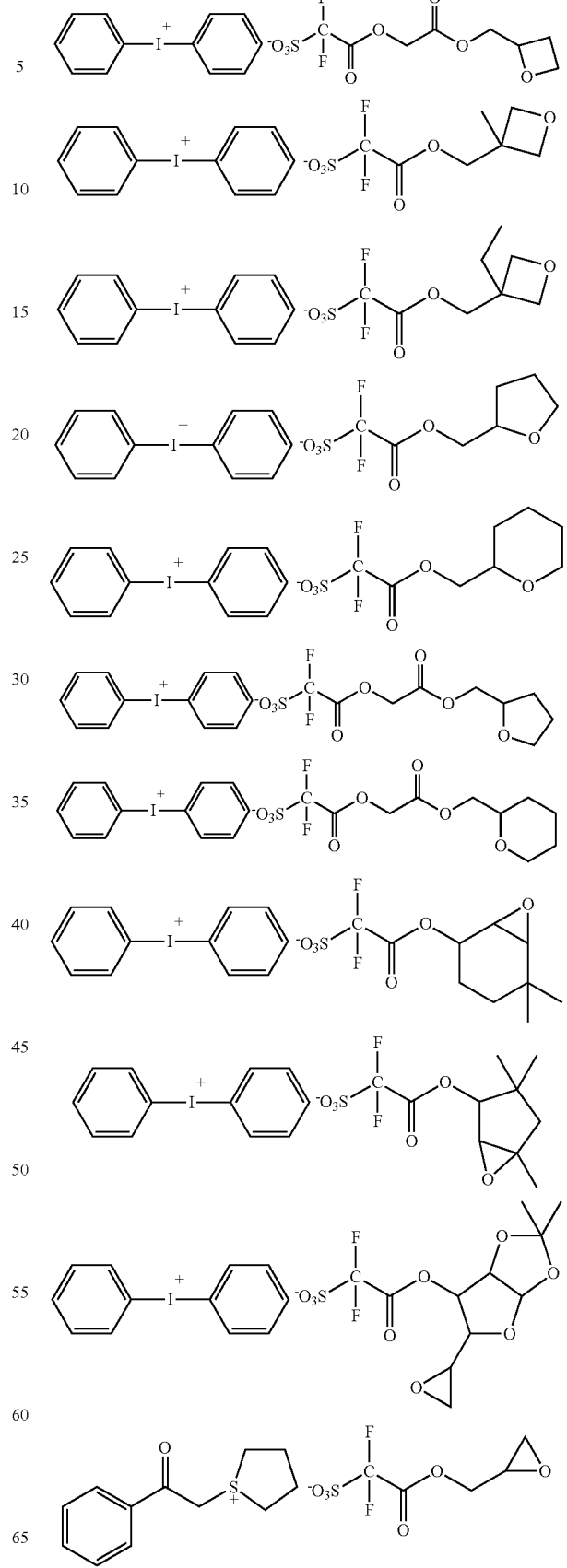

-continued
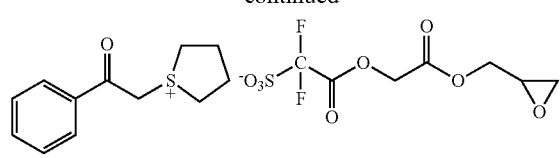
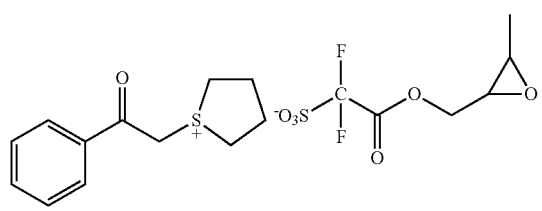
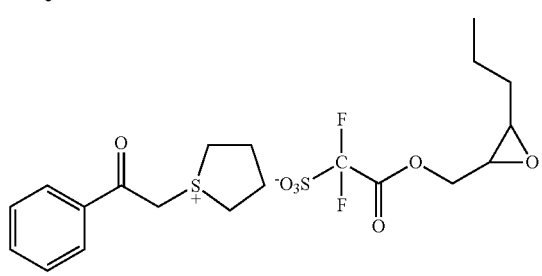
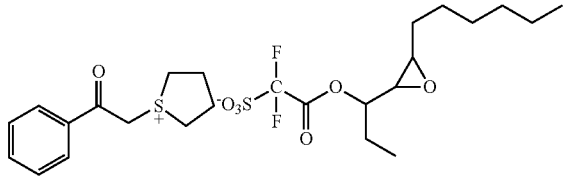
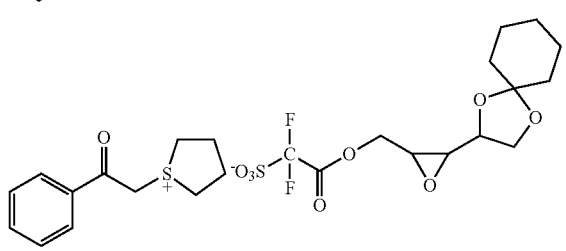
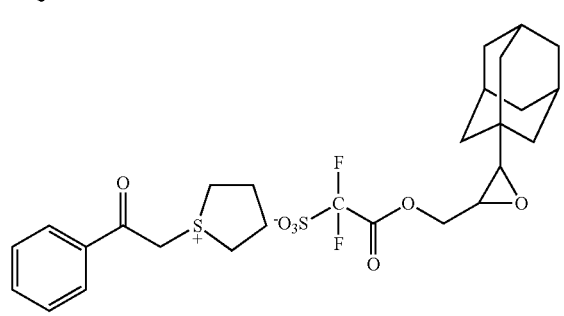
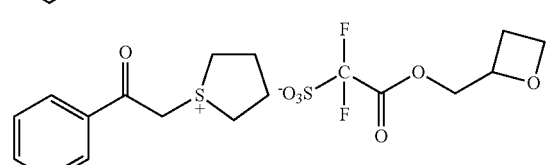
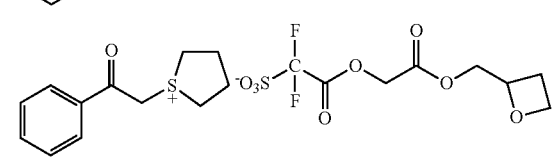
-continued
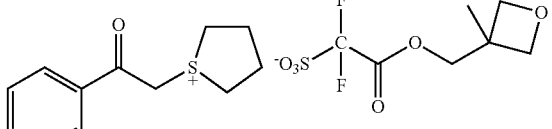
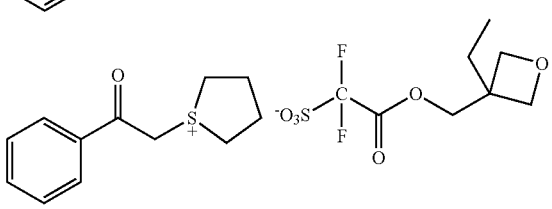
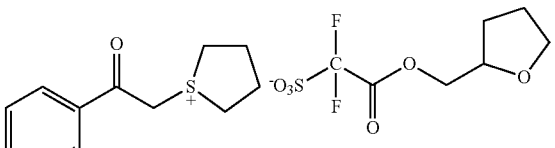
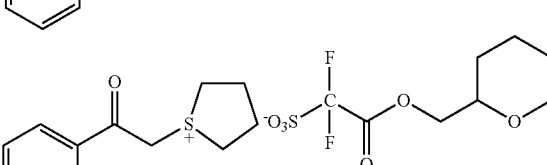
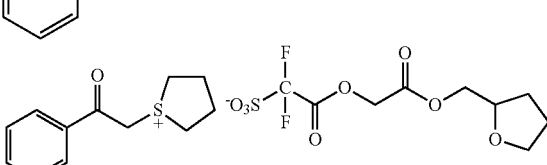
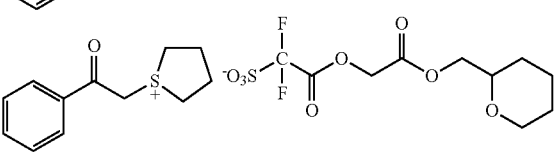
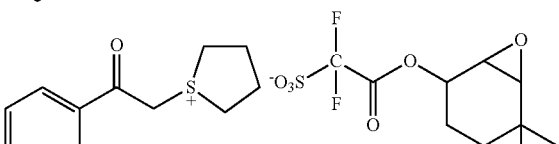
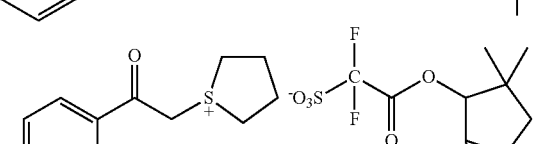
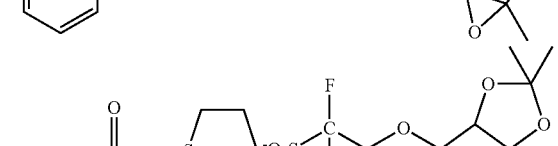
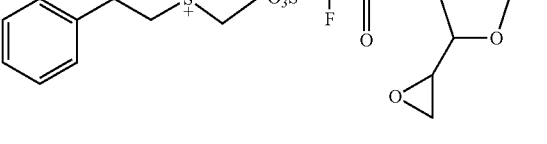
The process for producing SALT (I) will be illustrated.
For example, a salt represented by the formula (I') can be produced by reacting a compound represented by the formula (I-2) with a salt represented by the formula (I-1) in a solvent such as acetonitrile.

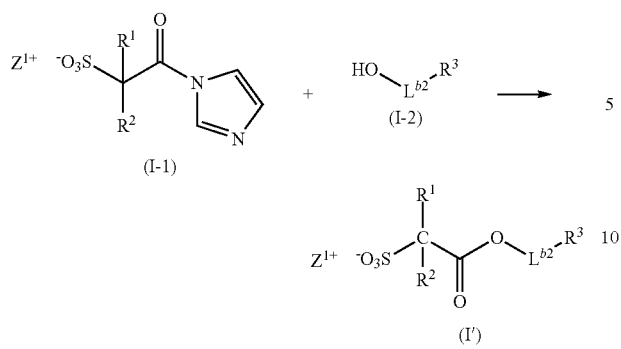

wherein $R^1$, $R^2$, $R^3$, $L^{b2}$ and $Z^{1+}$ are the same as defined above.

A salt represented by the formula (IIA) can be produced by reacting a compound represented by the formula (IIA-2) with a salt represented by the formula (IIA-1) in a solvent such as acetonitrile.

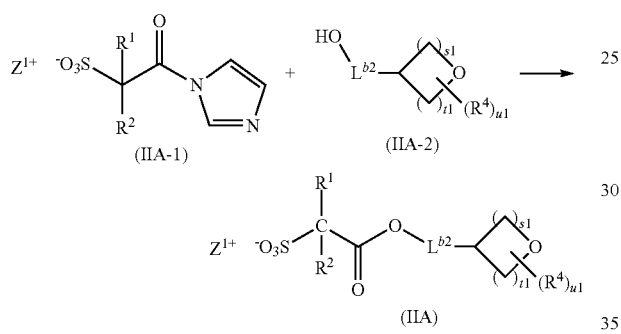

wherein $R^1$, $R^2$, $R^4$, $L^{b2}$, s1, t1, u1 and $Z^{1+}$ are the same as defined above.

Examples of the compound represented by the formula (IIA-2) include glycidol, 2-(hydroxymethyl)oxetane and (3-ethyl-3-oxetane)methanol. The salt represented by the formula (IIA-1) can be produced by reacting a salt represented by the formula (IIA-3) with carbonyldiimidazole in a solvent such as acetonitrile.

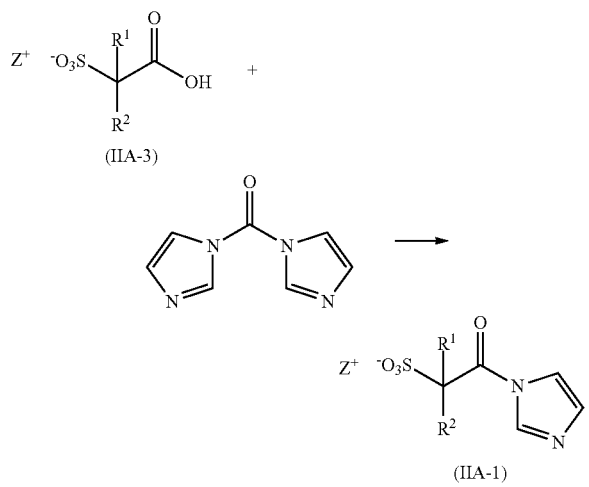

wherein $R^1$, $R^2$ and $Z^{1+}$ are the same as defined above.

The salt represented by the formula (IIA-3) can be produced according to the method described in JP 2008-127367 A.

For example, a salt represented by the formula (IIB) can be produced by reacting a compound represented by the formula (IIB-2) with a salt represented by the formula (IIB-1) in a solvent such as acetonitrile.

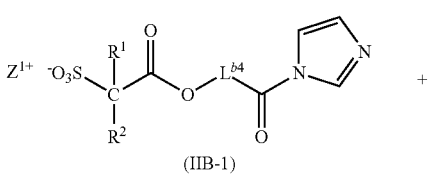

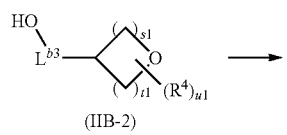

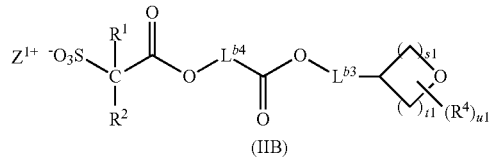

wherein $R^1$, $R^2$, $R^4$, $L^{b3}$, $L^{b4}$, s1, t1, u1 and $Z^{1+}$ are the same as defined above.

Examples of the compound represented by the formula (IIB-2) include glycidol and 2-(hydroxymethyl)oxetane. The salt represented by the formula (IIB-1) can be produced by reacting a salt represented by the formula (IIB-2) with carbonyldiimidazole in a solvent such as acetonitrile.

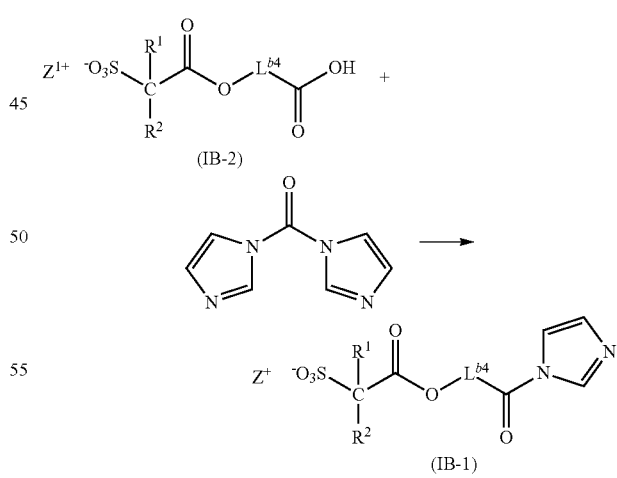

wherein $R^1$, $R^2$, $L^{b4}$ and $Z^{1+}$ are the same as defined above.

The salt represented by the formula (IB-2) can be produced by reacting a compound represented by the formula (IIB-5) with a salt represented by the formula (IIB-4) in the presence of a catalyst such as potassium iodide and potassium carbonate in a solvent such as N,N-diemthylformamide.

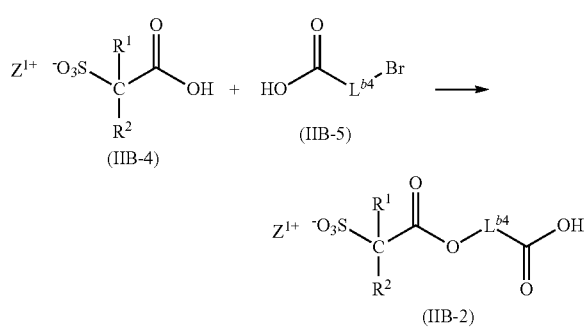

wherein $R^1$, $R^2$, $L^{b4}$ and $Z^{1+}$ are the same as defined above.

Examples of the compound represented by the formula (IIB-5) include bromoacetic acid, and examples of the salt represented by the formula (IIB-4) can be produced according to the method described in JP 2008-127367 A.

The acid generator of the present invention comprises SALT (I). The acid generator of the present invention can contain two or more kinds of SALT (I). The acid generator of the present invention can contain one or more known acid generators other than SALT (I) in addition to SALT (I). The photoresist composition preferably contains SALT (I) and one or more acid generators other than SALT (I) as the acid generator.

The photoresist composition comprises the acid generator comprising SALT (I) and a resin.

The content of SALT (I) is usually 1 part by weight or more relative to 100 parts by weight of the resin and preferably 3 part by weight or more. The content of SALT (I) is usually 30 parts by weight or less relative to 100 parts by weight of the resin and preferably 25 parts by weight or less.

The acid generators other than SALT (I) that may be used include nonionic acid generators and ionic acid generators. Examples of the nonionic acid generator include organic halides, sulfonate esters such as 2-nitrobenzyl ester, aromatic sulfonate, oxime sulfonate, N-sulfonyloxyimide, sulfonyloxyketone and DNQ 4-sulfonate, and sulfones such as disulfone, ketosulfone and sulfonyldiazomethane. Examples of the ionic acid generator include onium salts such as a diazonium salt, a phosphonium salt, a sulfonium salt and an iodonium salt, and examples of the anion of the onium salt include sulfonic acid anion, sulfonylimide anion and sulfonylmethide anion.

Other examples of the acid generator include acid generators described in JP 63-26653A, JP 55-164824 A, JP 62-69263A, JP 63-146038 A, JP 63-163452 A, JP 62-153853 A, JP 63-146029 A, U.S. Pat. No. 3,779,778, U.S. Pat. No. 3,849,137, DE Patent No. 3914407 and EP Patent No. 126,712.

A fluorine-containing acid generator is preferable.

Preferable examples of the acid generator include a salt represented by the formula (B1):

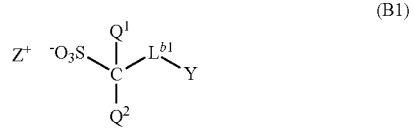

(B1)

wherein $Q^1$ and $Q^2$ each independently represent a fluorine atom or a C1-C6 perfluoroalkyl group, $L^{b1}$ represents a single bond or a C1-C17 divalent saturated hydrocarbon group in which one or more —$CH_2$— can be replaced by —O— or —CO—, Y represents a C1-C18 aliphatic hydrocarbon group which can have one or more substituents or a C3-C18 saturated cyclic hydrocarbon group which can have one or more substituents, and one or more —$CH_2$— in the aliphatic hydrocarbon group and the saturated cyclic hydrocarbon group can be replaced by —O—, —$SO_2$— or —CO—, and $Z^+$ represents an organic counter cation.

Examples of the C1-C6 perfluoroalkyl group include the same as described above, and a trifluoromethyl group is preferable. $Q^1$ and $Q^2$ independently preferably represent a fluorine atom or a trifluoromethyl group, and $Q^1$ and $Q^2$ are more preferably fluorine atoms.

Examples of the C1-C17 saturated divalent hydrocarbon group include a C1-C17 alkanediyl group and a divalent group having an alicyclic divalent hydrocarbon group. Examples of the alkanediyl group include the same as described above.

One or more —$CH_2$— in the C1-C6 alkanediyl group can be replaced by —O— or —CO—.

Examples of the C1-C17 saturated hydrocarbon group in which one or more —$CH_2$— are replaced by —O— or —CO— include the same as described above. Among them, preferred are *—CO—O-$L^{b2}$-, *—CO—O-$L^{b4}$-CO—O-$L^{b3}$-, *-$L^{b5}$-O—CO— and *-$L^{b7}$-O-$L^{b6}$-, and more preferred are *—CO-$L^{b2}$- and *—CO—O-$L^{b4}$-CO—O-$L^{b3}$-, and much more preferred is *—CO—O-$L^{b2}$-, and especially preferred is *—CO—O-$L^{b2}$- in which $L^{b2}$ is a single bond or —$CH_2$—.

Examples of the substituent in Y include a halogen atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —$(CH_2)_{j2}$—O—CO—$R^{b1}$— in which $R^{b1}$ represents a C1-C16 aliphatic hydrocarbon group, a C3-C16 saturated cyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above. Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C36 aliphatic hydrocarbon group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C36 saturated cyclic hydrocarbon group represented by Y include the groups represented by the formulae (Y1) to (Y26):
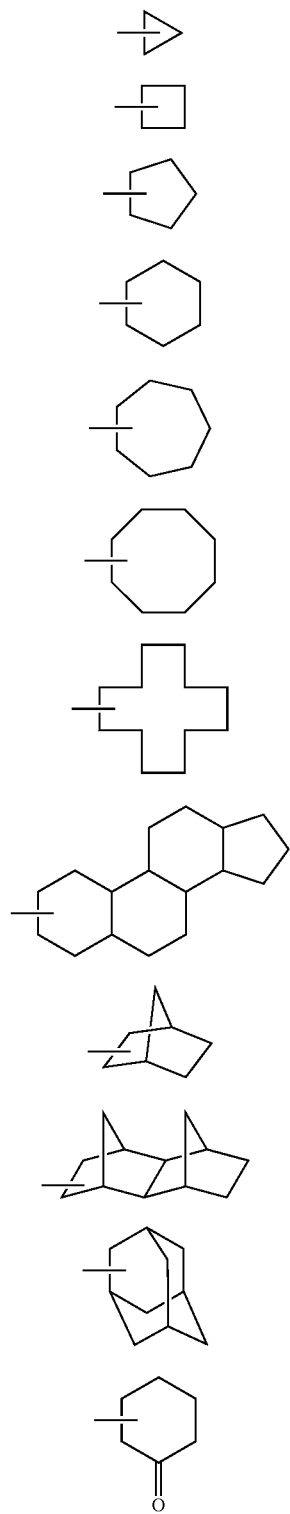
(Y1)
(Y2)
(Y3)
(Y4)
(Y5)
(Y6)
(Y7)
(Y8)
(Y9)
(Y10)
(Y11)
(Y12)
-continued
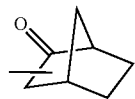
(Y13)
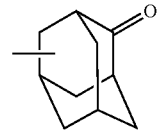
(Y14)
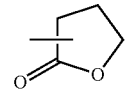
(Y15)
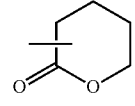
(Y16)
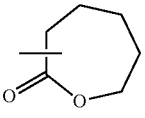
(Y17)
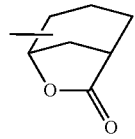
(Y18)
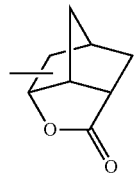
(Y19)
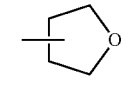
(Y20)
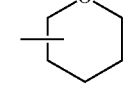
(Y21)
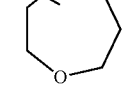
(Y22)
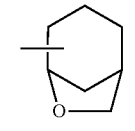
(Y23)
(Y24)

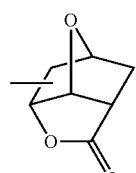
(Y25)

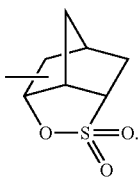
(Y26)

Among them, preferred are the groups represented by the formulae (Y1) to (Y19), and more preferred are the groups represented by the formulae (Y11), (Y14), (Y15) and (Y19). The groups represented by the formulae (Y11) and (Y14) are especially preferable.

Examples of Y having one or more substituents include the followings:

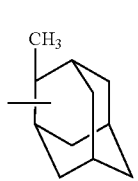 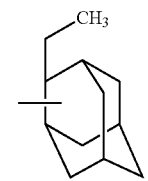 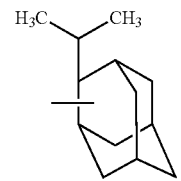

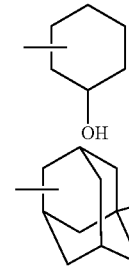 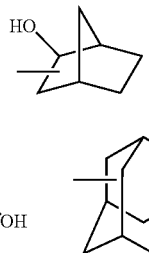 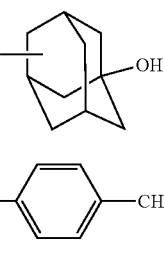

 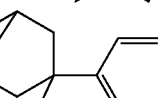 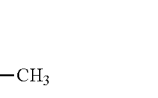

  

 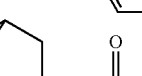 

 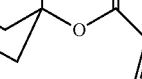 

Y is preferably an adamantyl group which can have one or more substituents, and is more preferably an adamantyl group or an oxoadamantyl group.

Among the sulfonic acid anions of the salt represented by the formula (B1), preferred is a sulfonic acid anion in which $L^{b1}$ is *—CO—O—$L^{b2}$-, and more preferred are anions represented by the formulae (b1-1-1) to (b1-1-9).

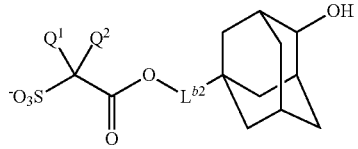 (b1-1-1)

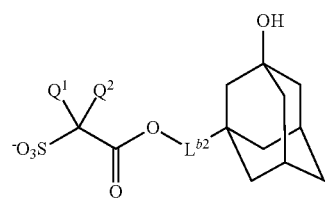 (b1-1-2)

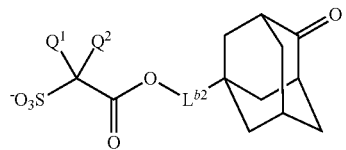 (b1-1-3)

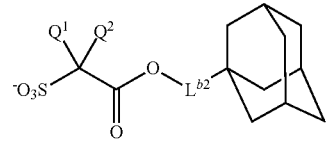 (b1-1-4)

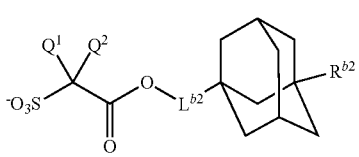 (b1-1-5)

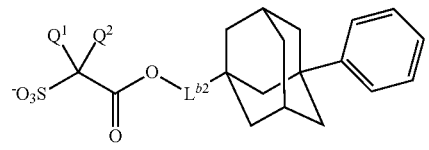 (b1-1-6)

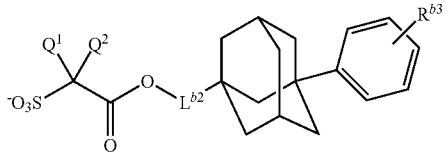 (b1-1-7)

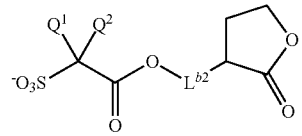 (b1-1-8)

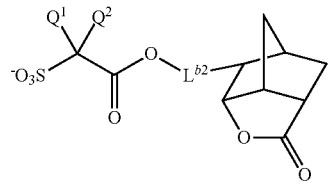 (b1-1-9)

wherein $Q^1$, $Q^2$ and $L^{b2}$ are the same as defined above, and $R^{b2}$ and $R^{b3}$ each independently represent a C1-C4 aliphatic hydrocarbon group, preferably a methyl group.

Examples of the anion of the acid generator other than SALT (I) include the following anions:

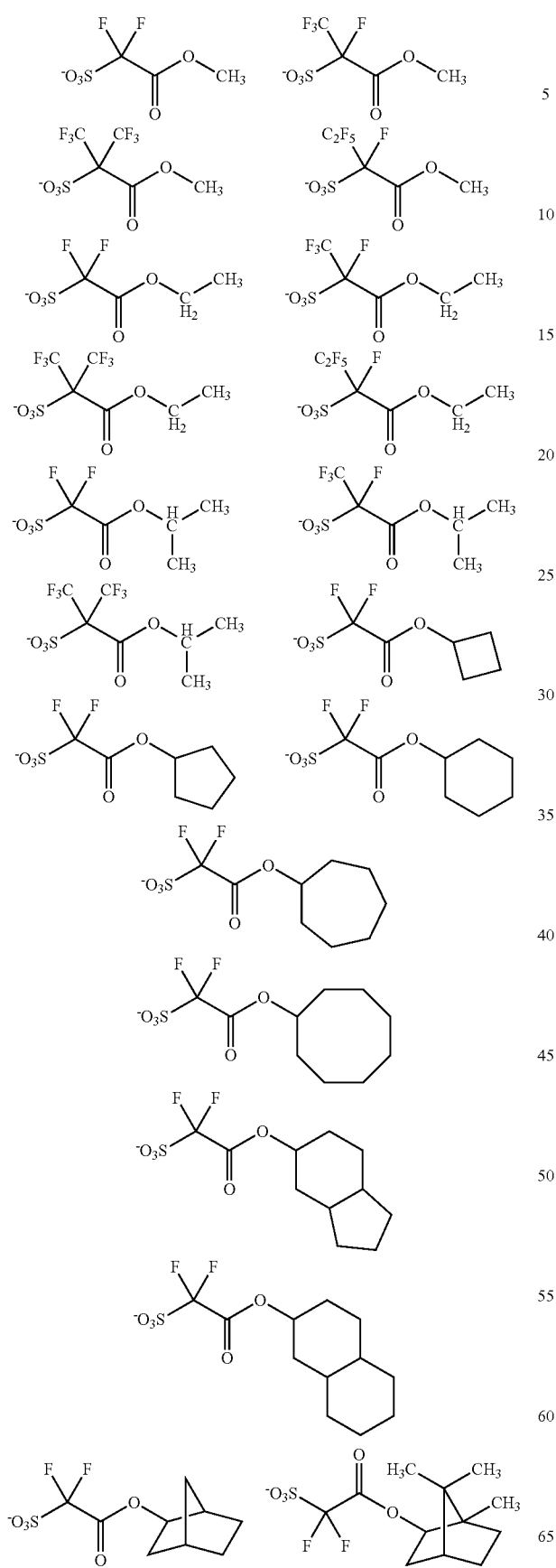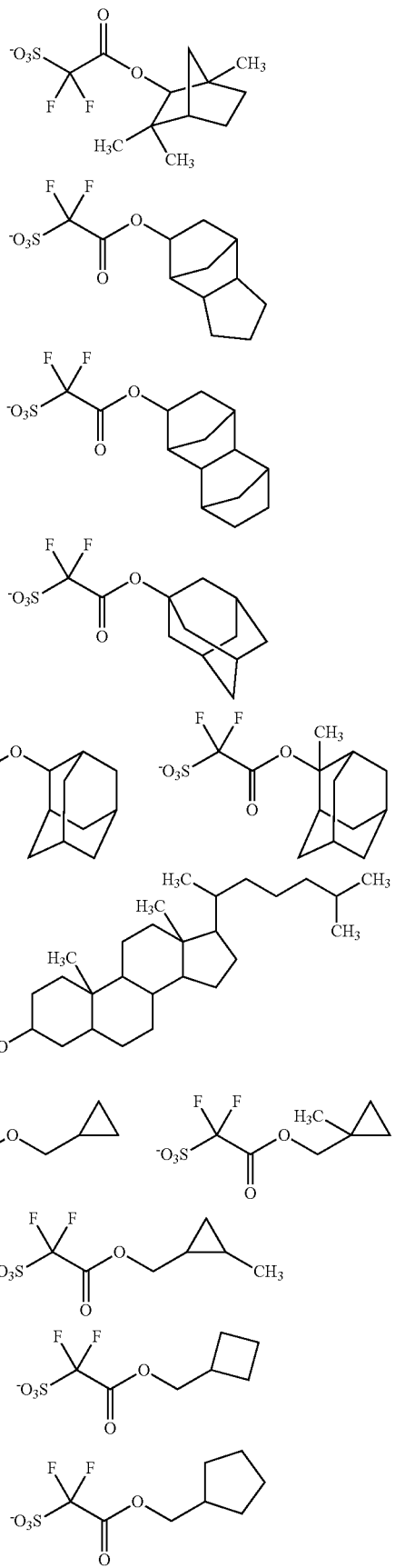

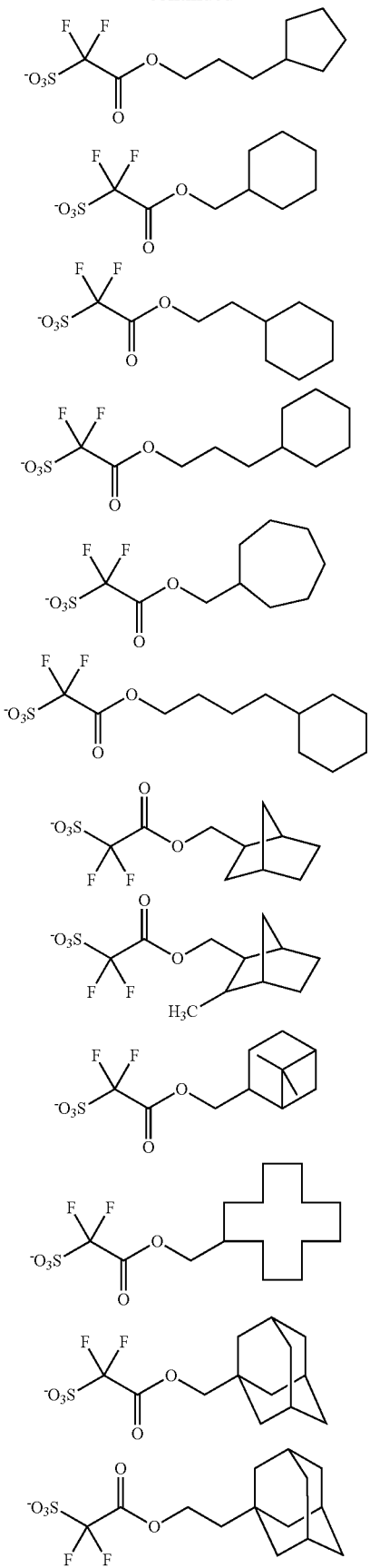
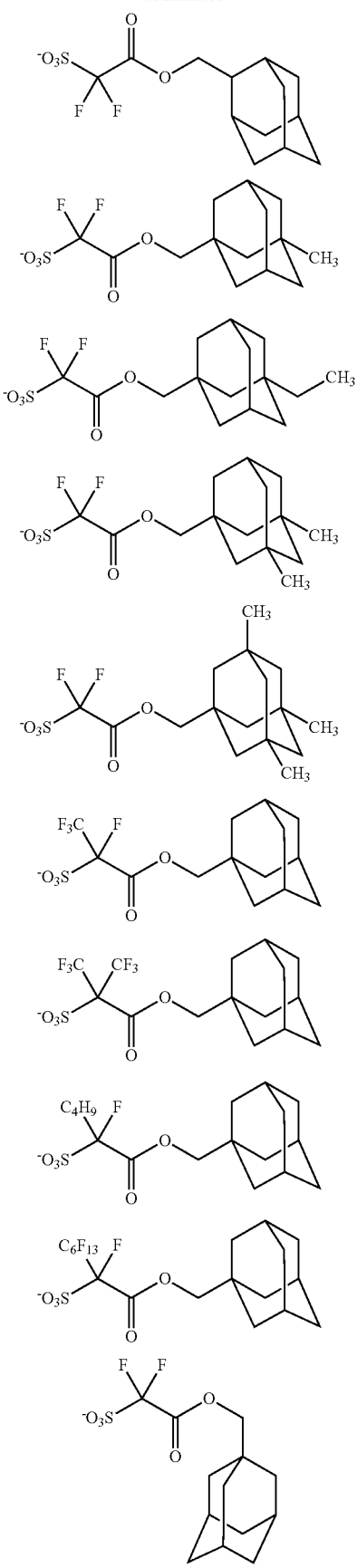

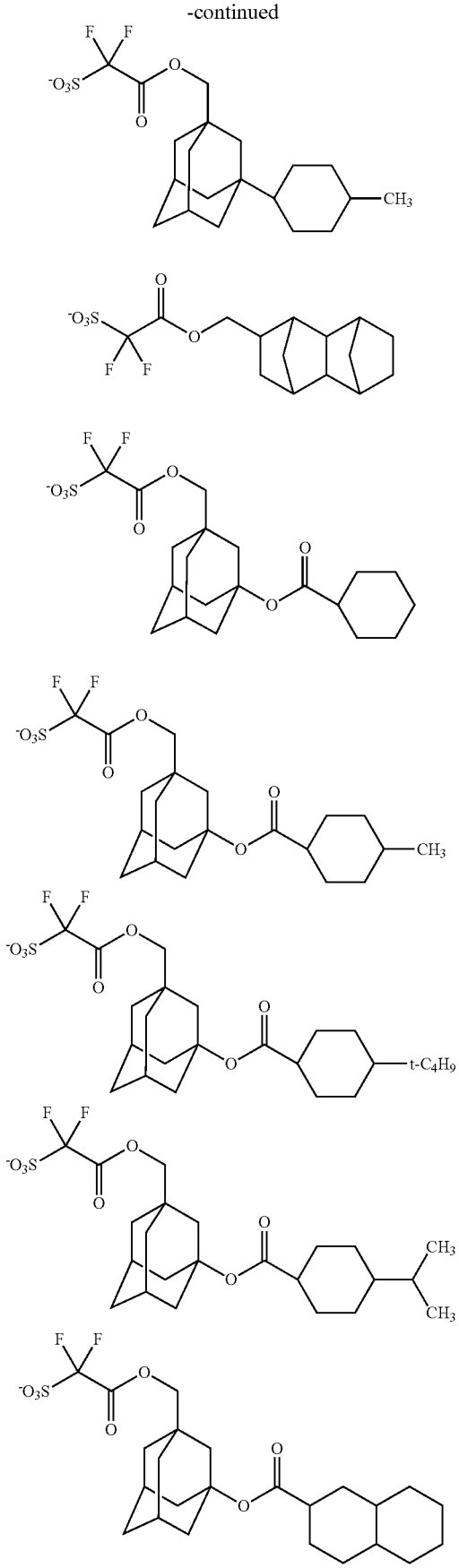
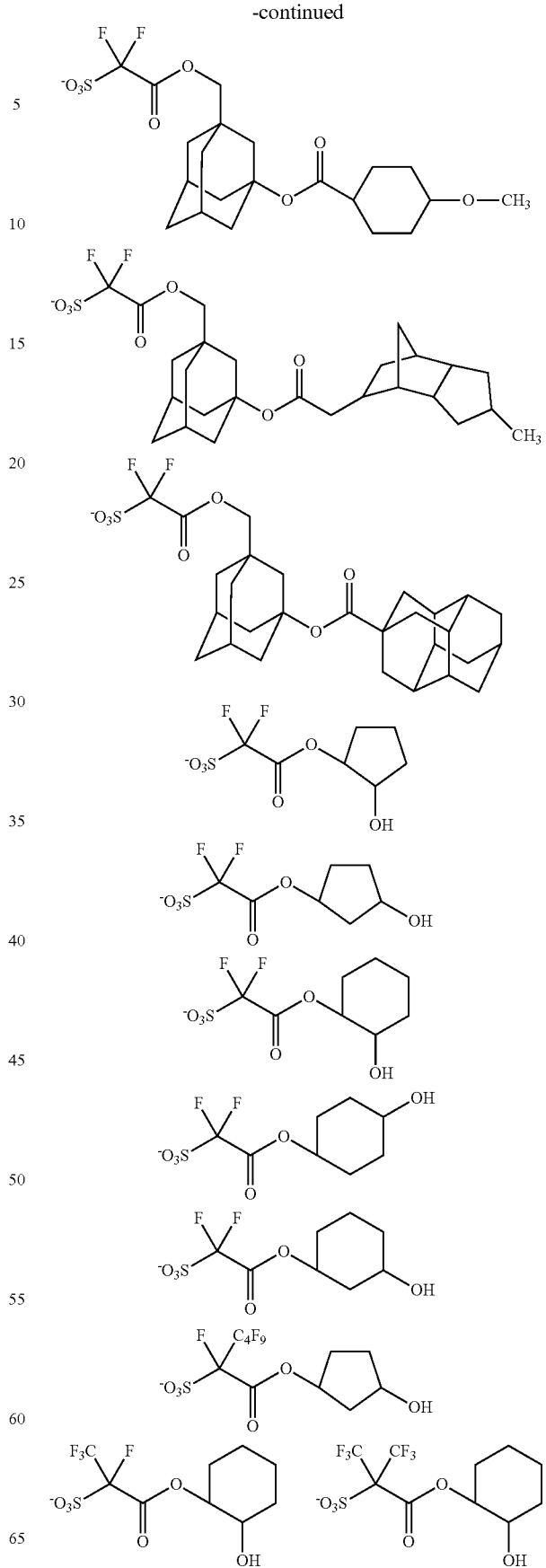

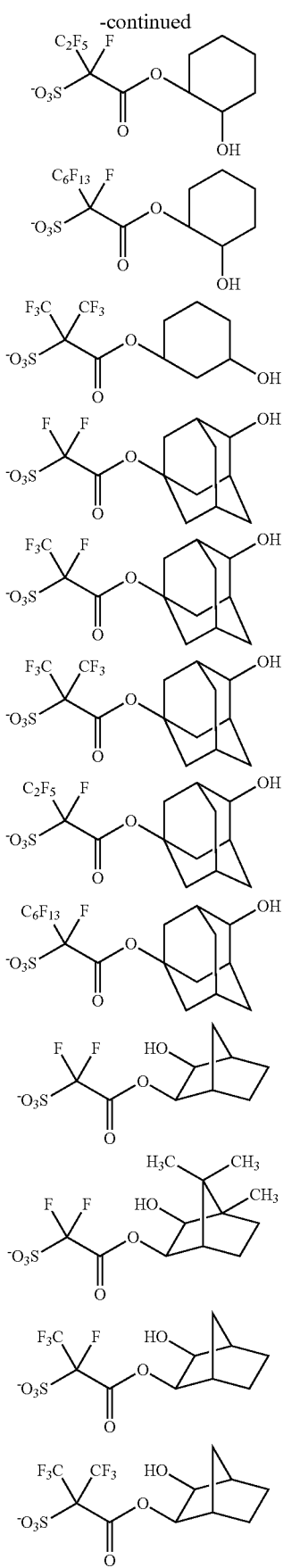
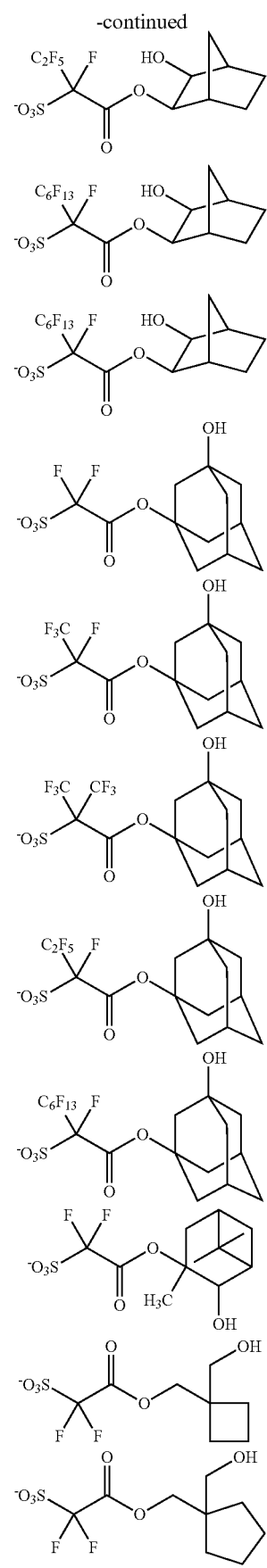

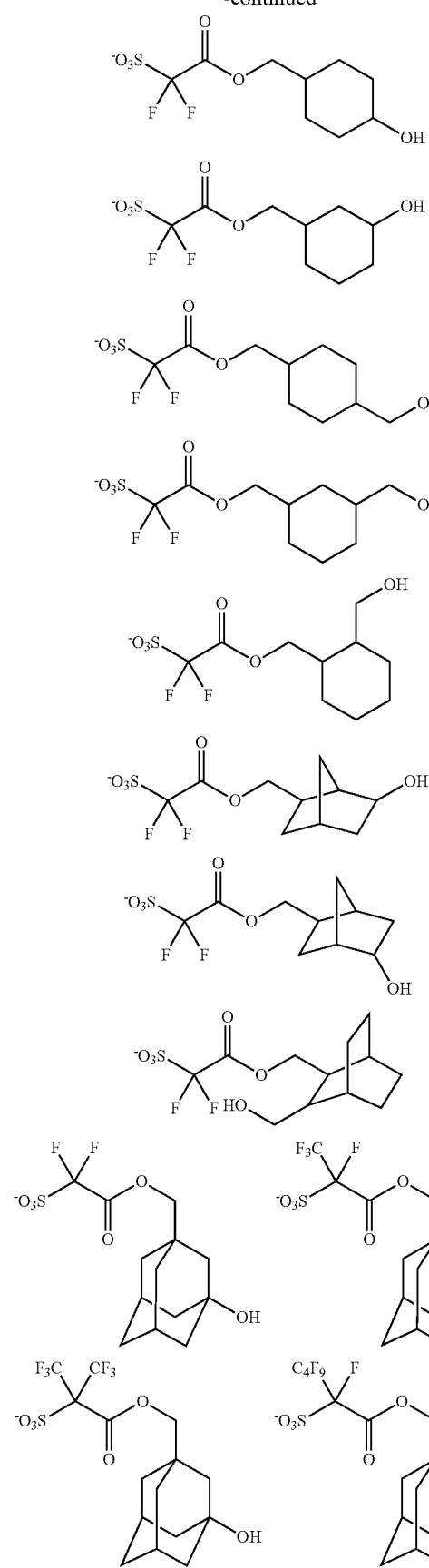
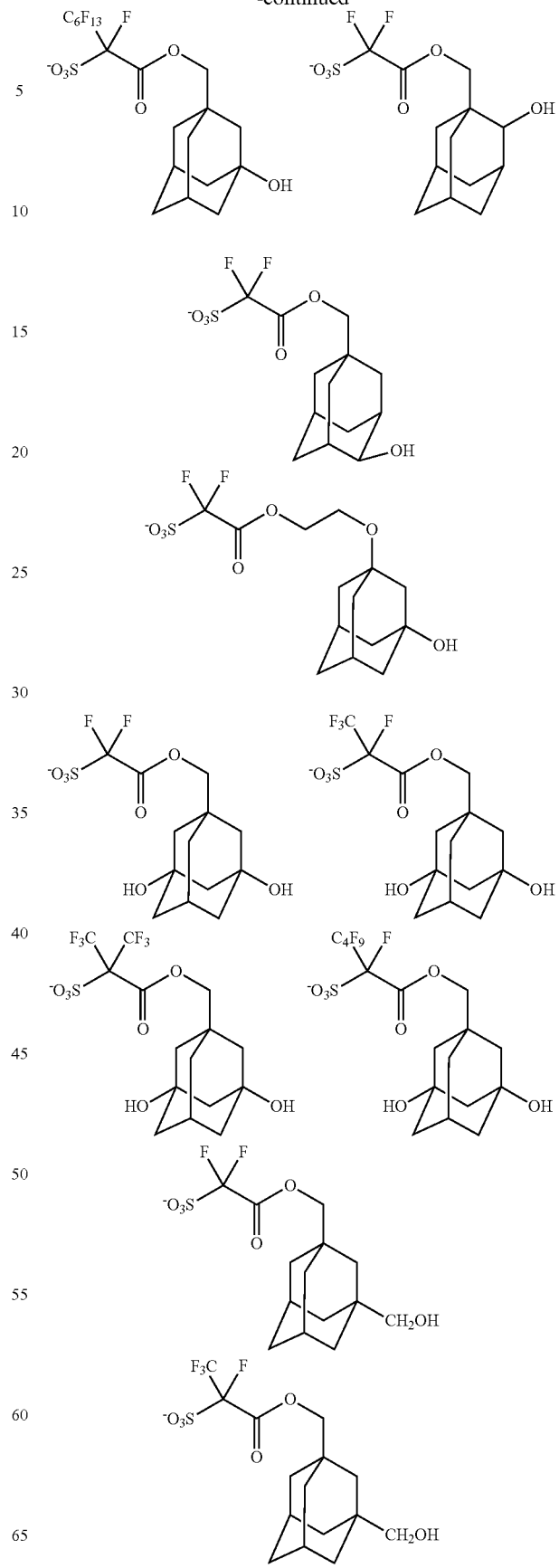

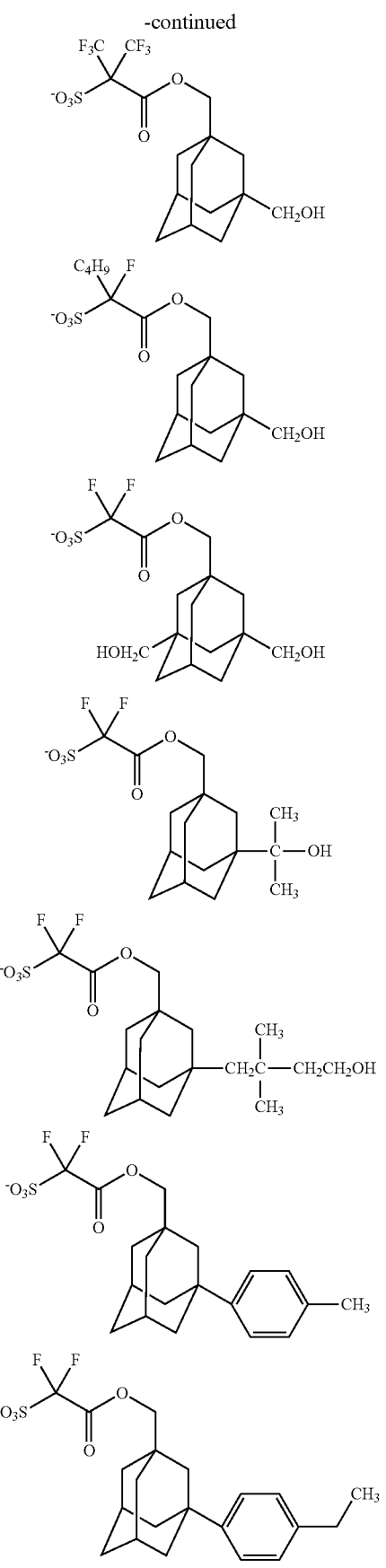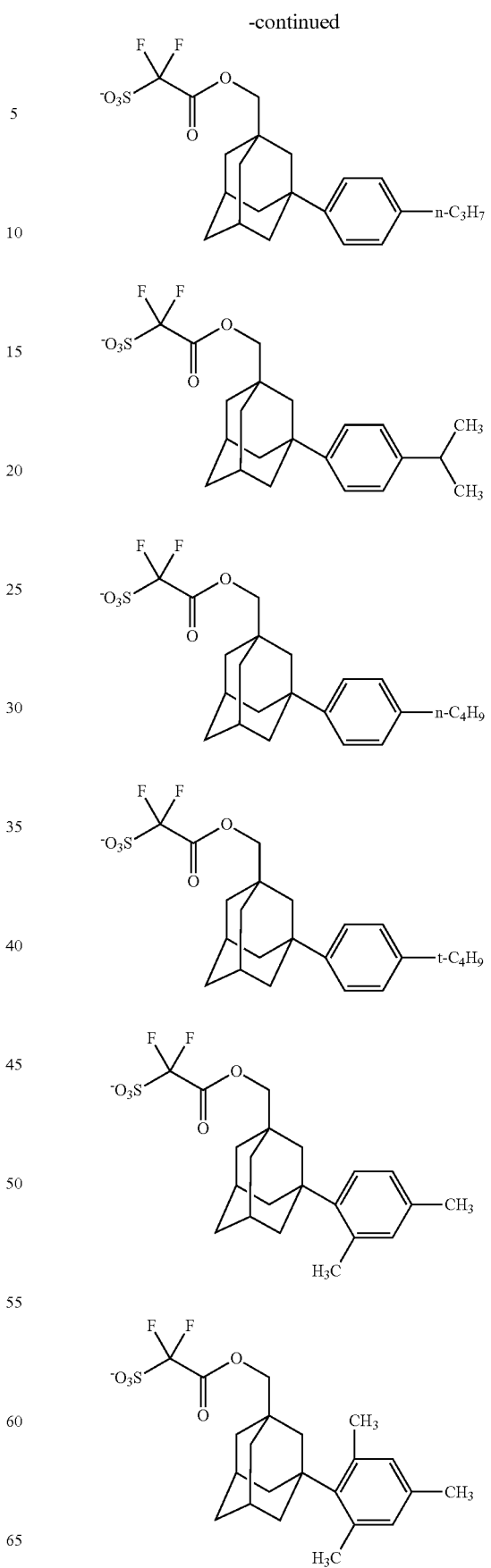

57
-continued
58
-continued
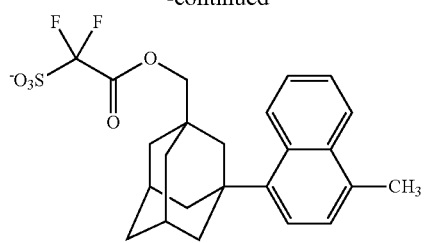
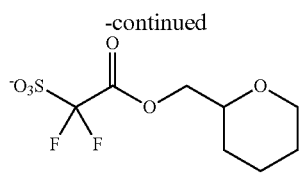
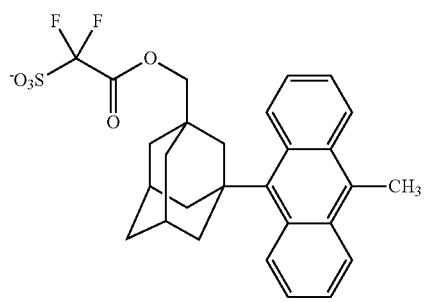
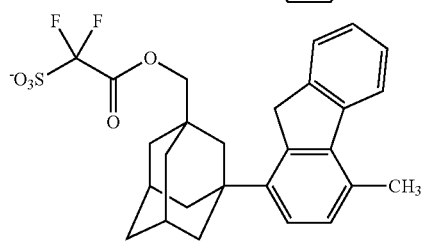
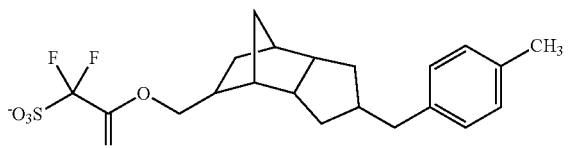
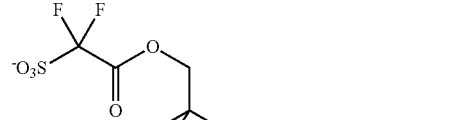
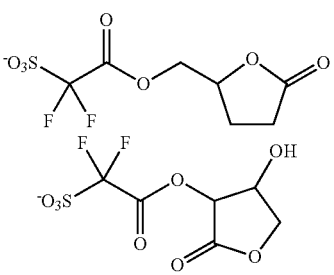
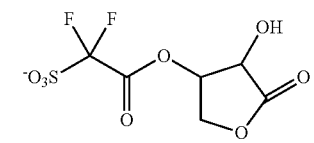
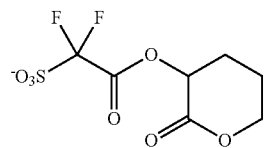
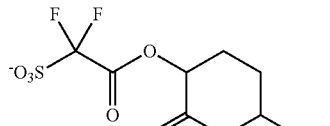
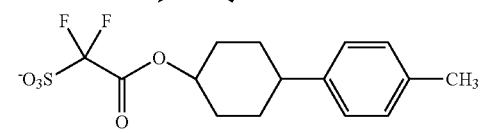
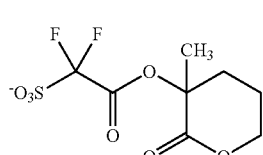
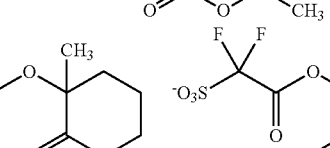
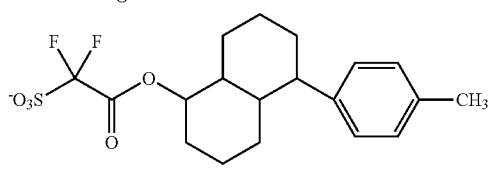
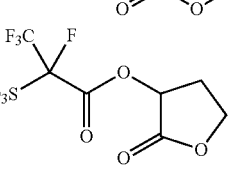

-continued
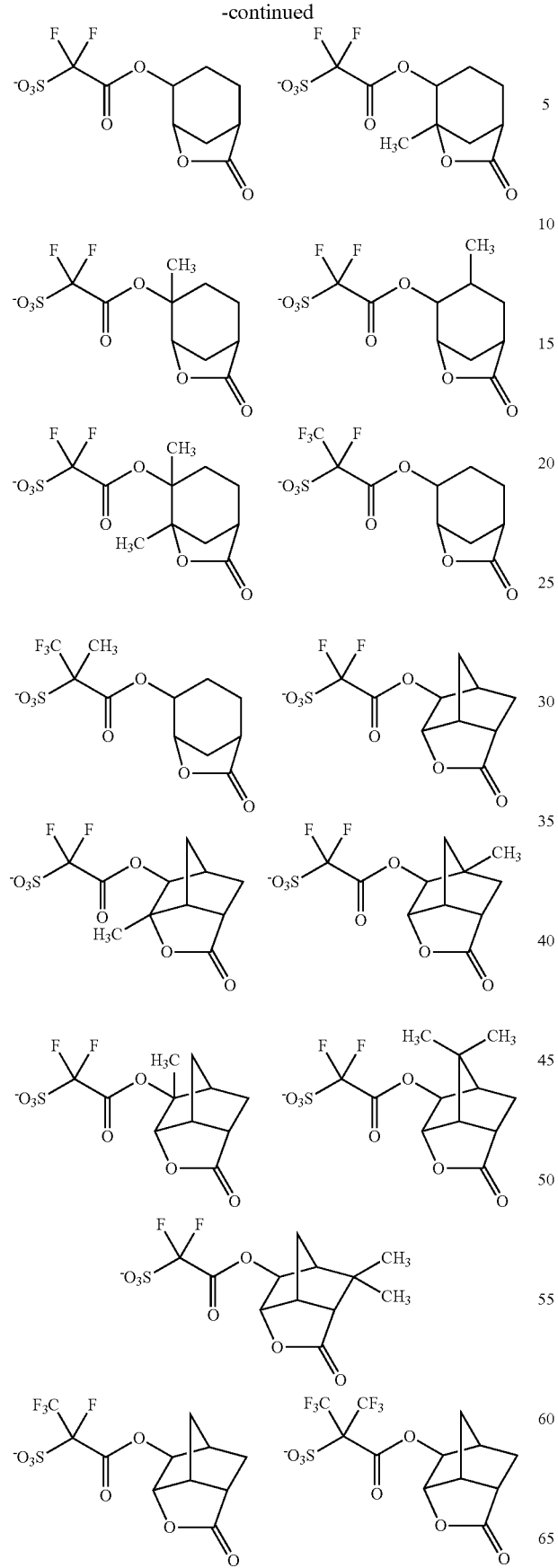
-continued
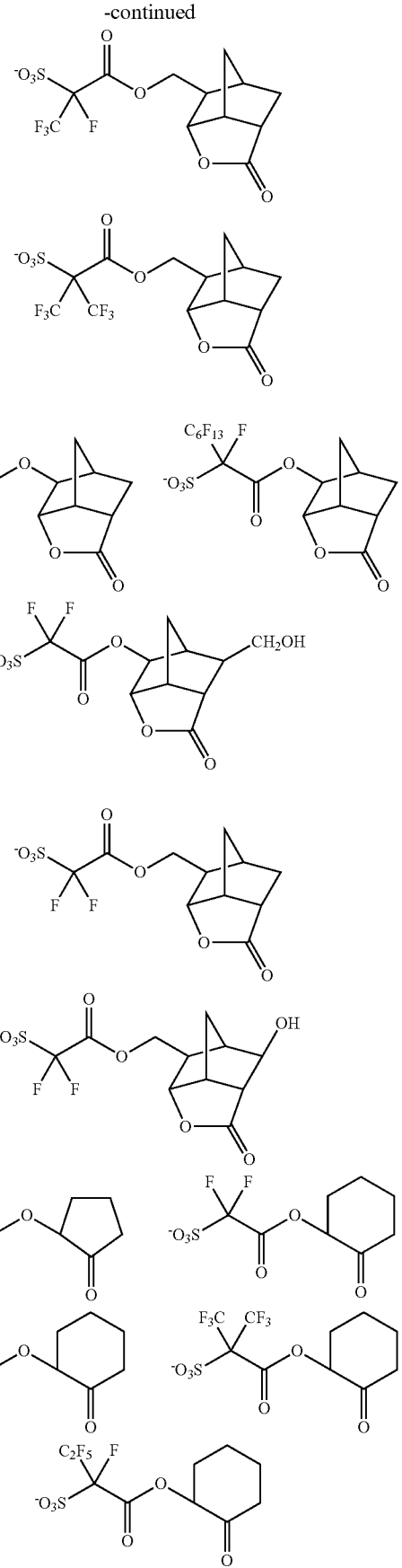

61
-continued
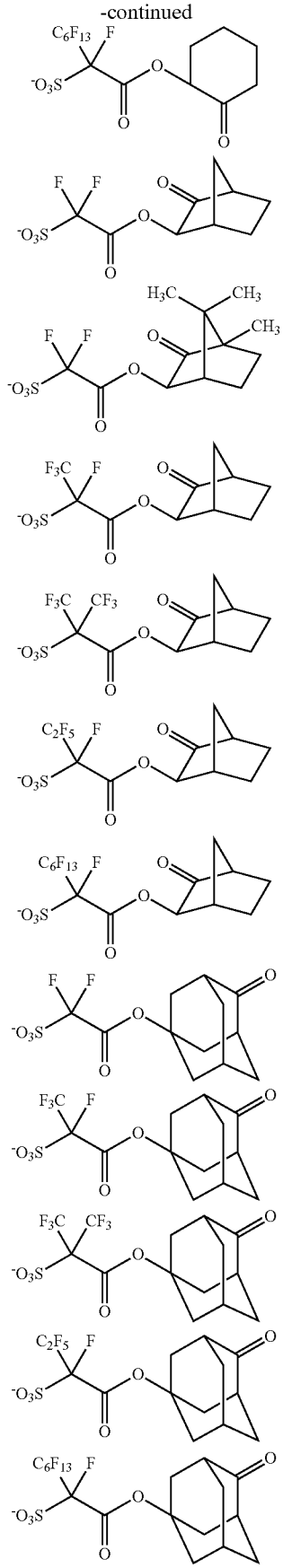
62
-continued
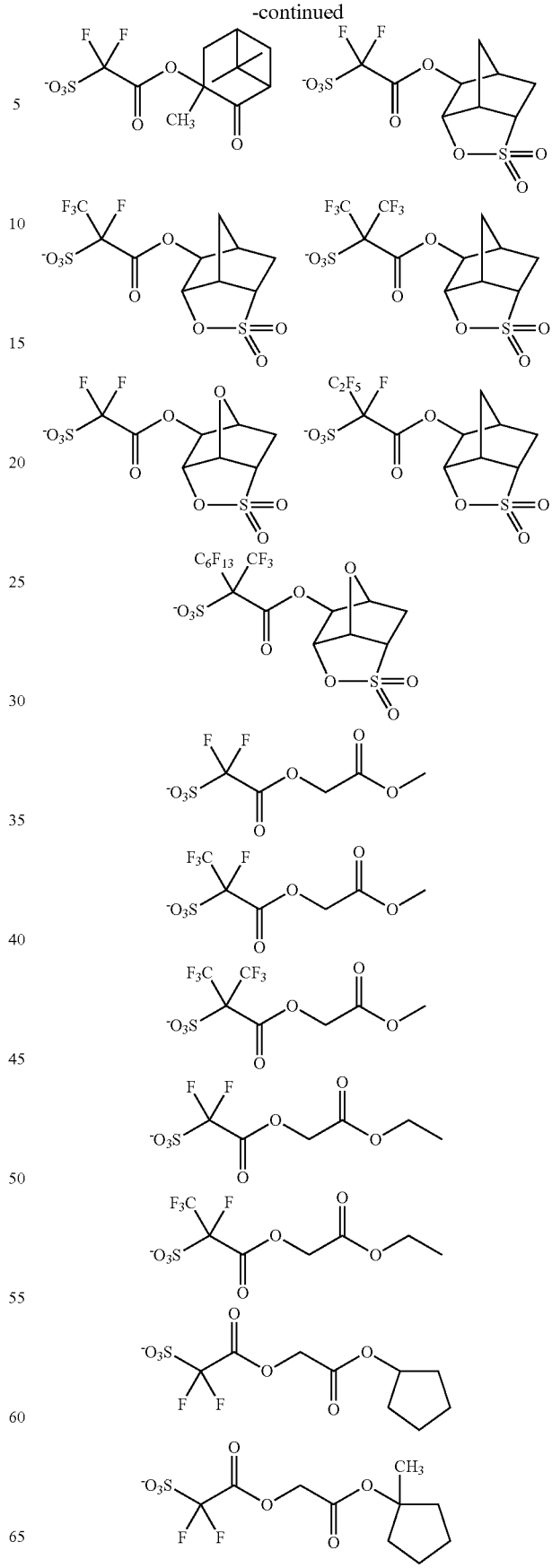

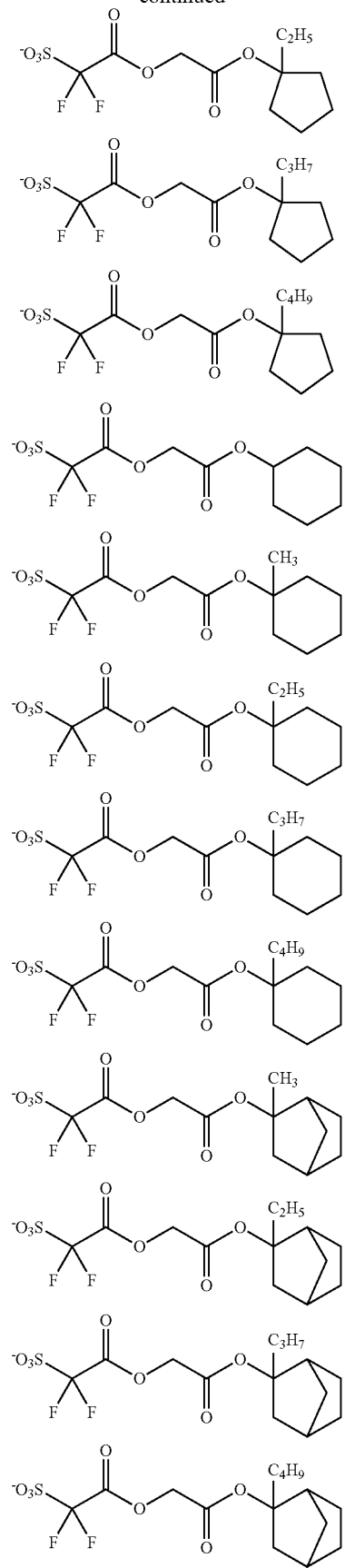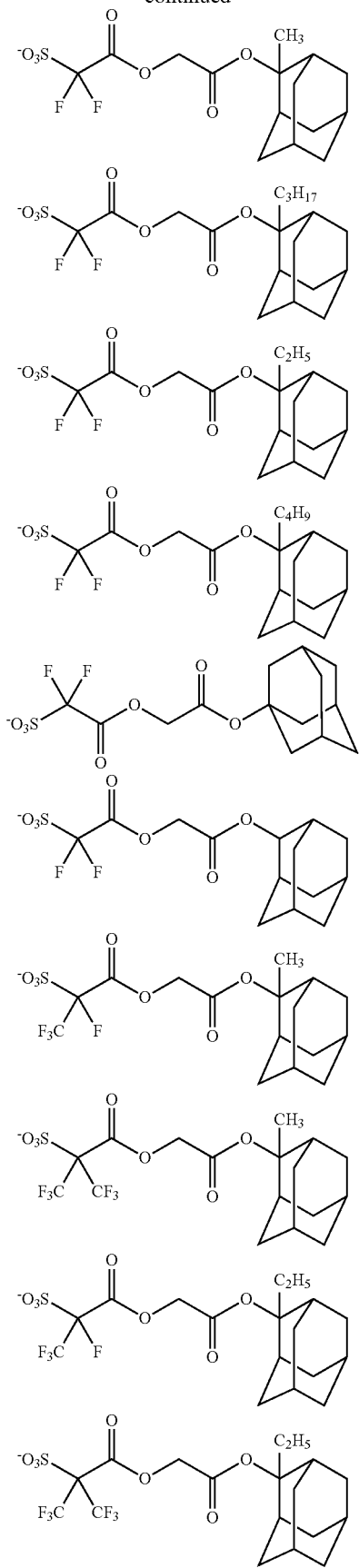

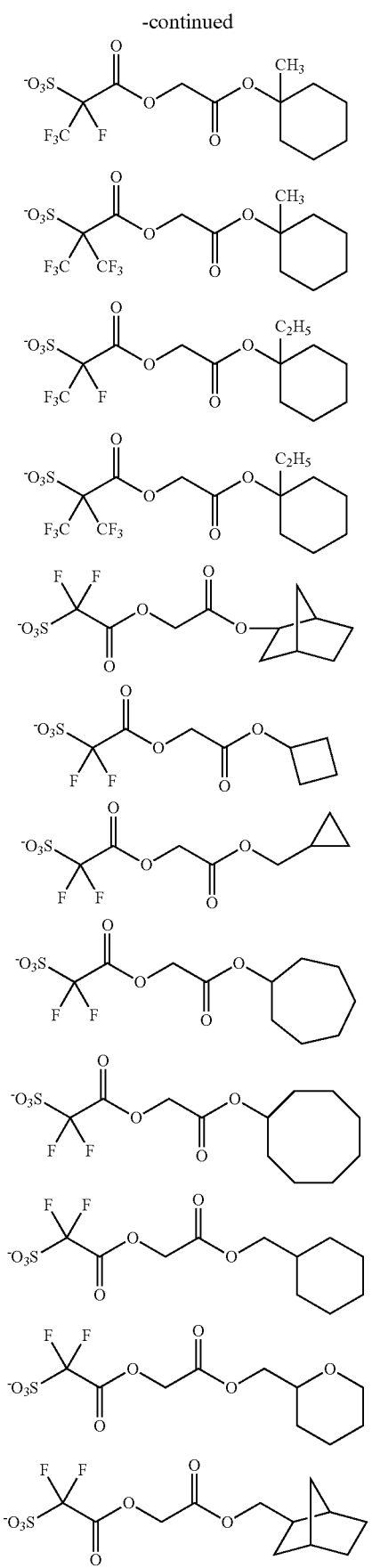
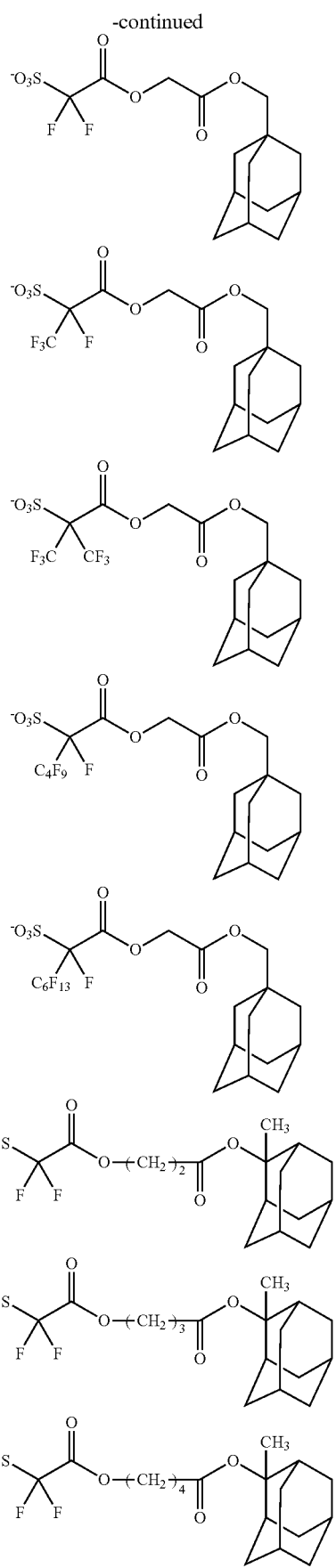

67
-continued
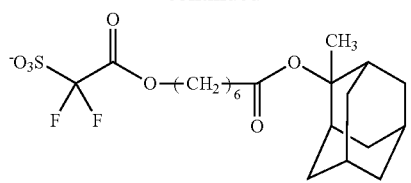
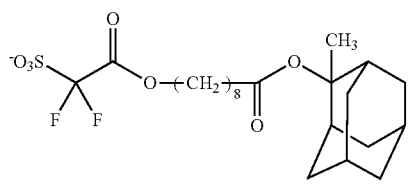
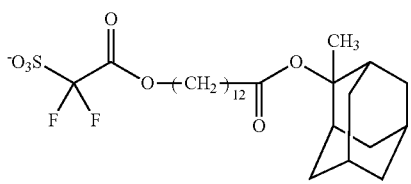
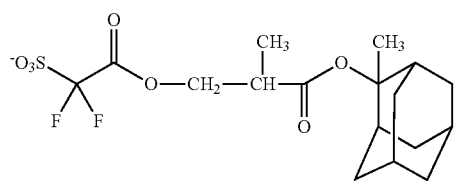
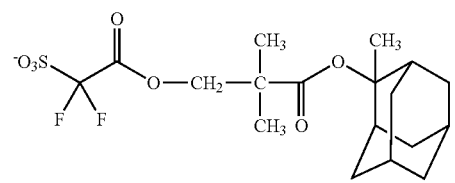
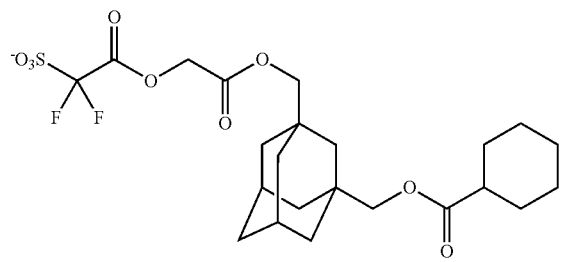
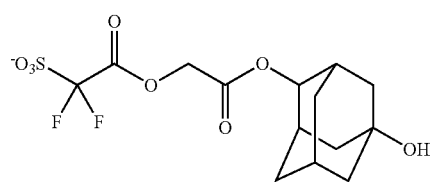
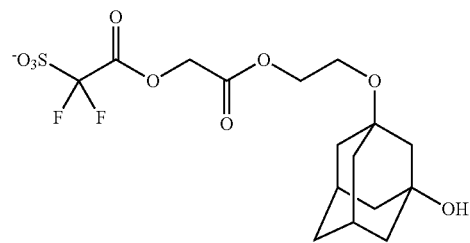
68
-continued
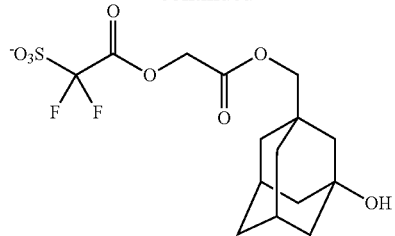
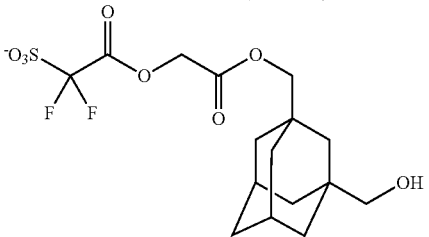
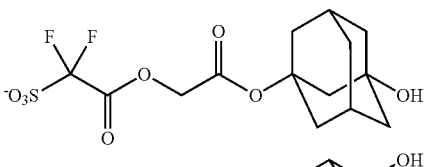
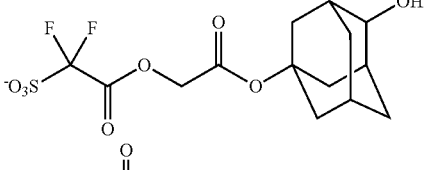
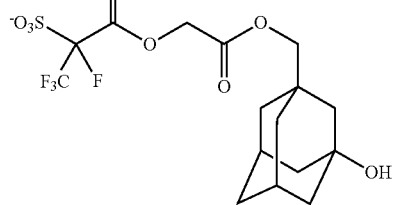
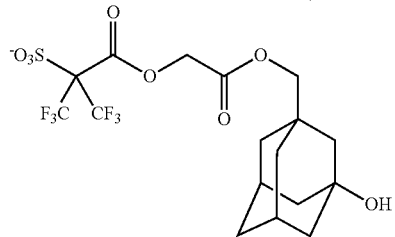
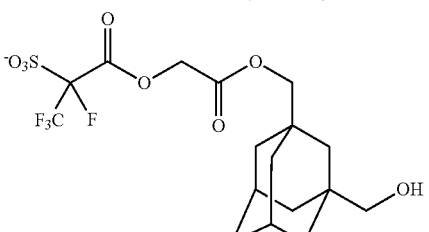
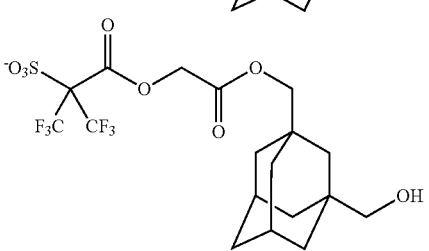

69
-continued
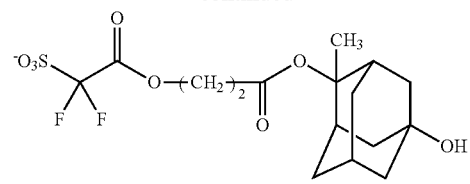
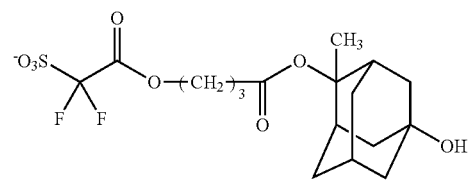
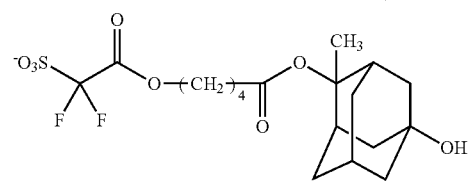
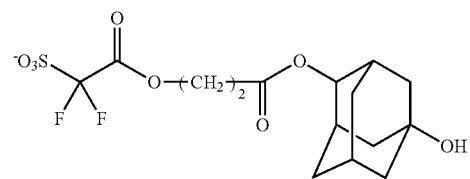
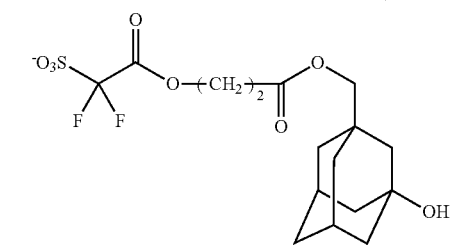
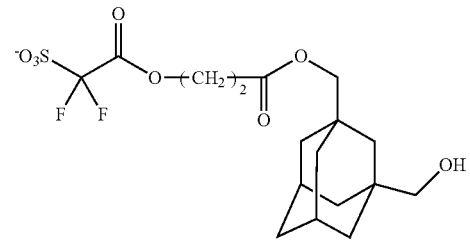
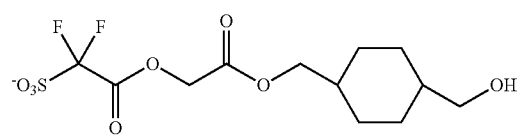
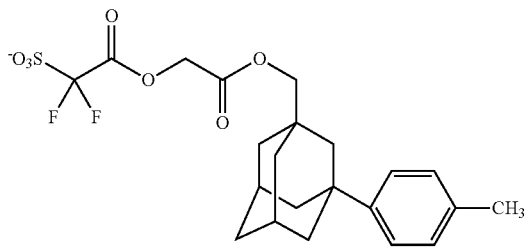
70
-continued
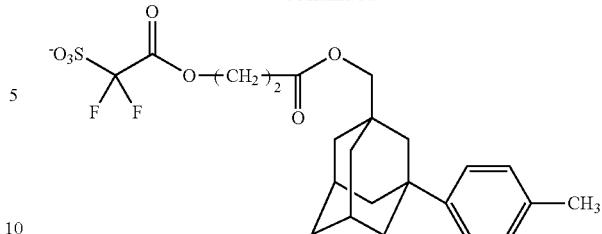
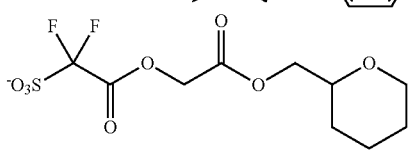
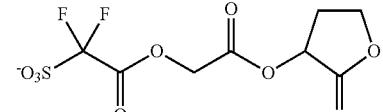
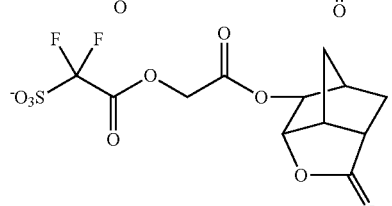
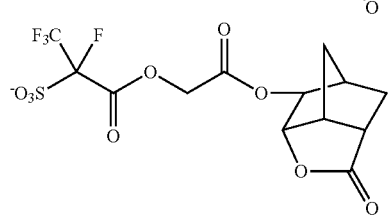
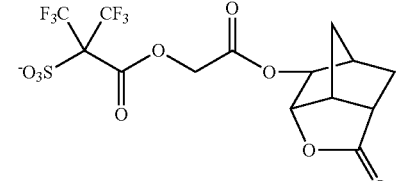
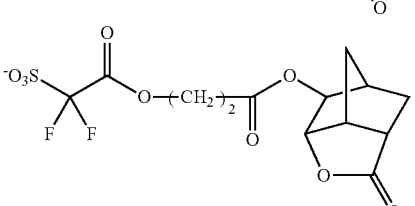
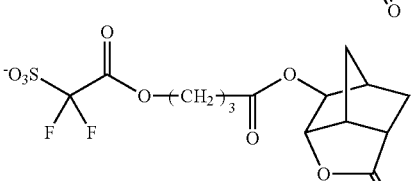
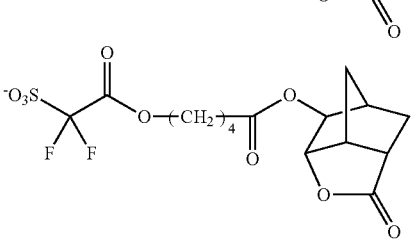

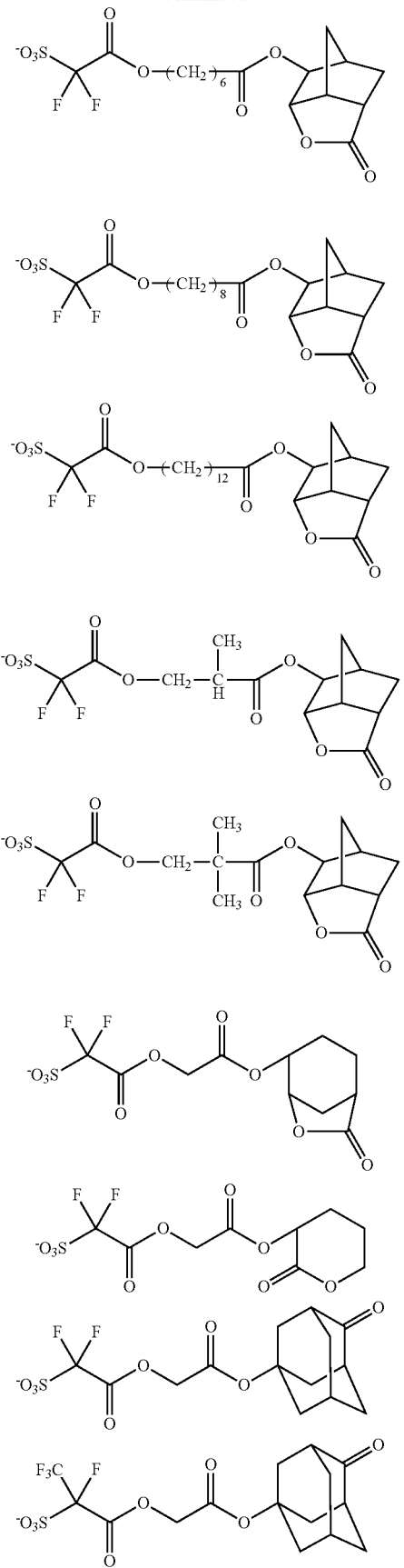
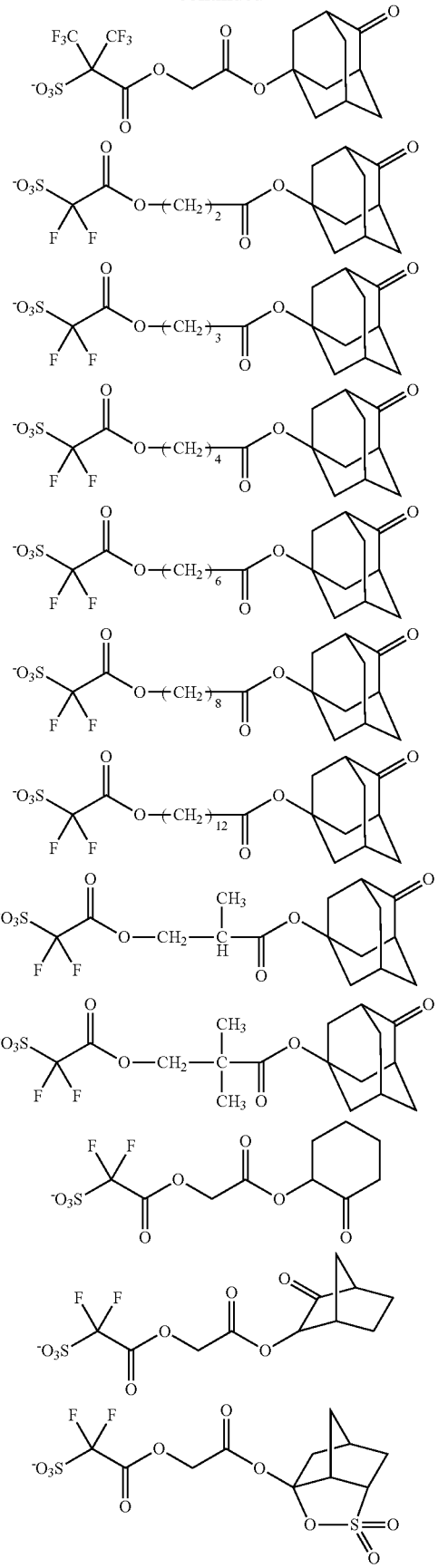

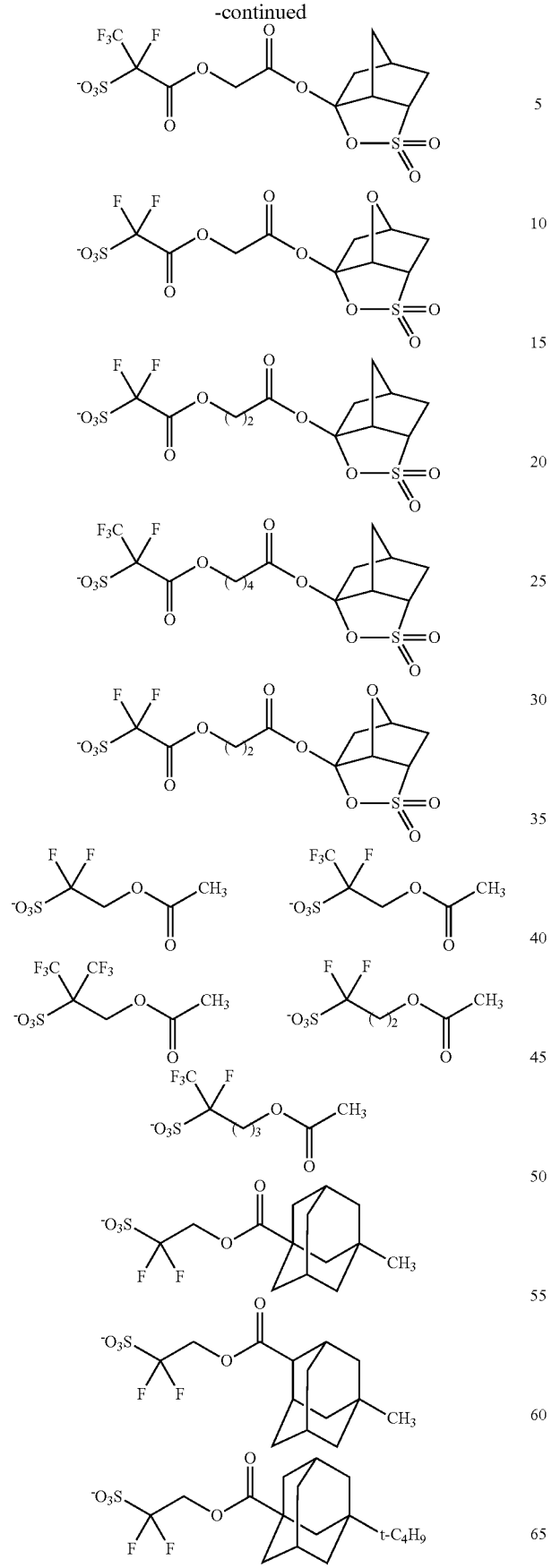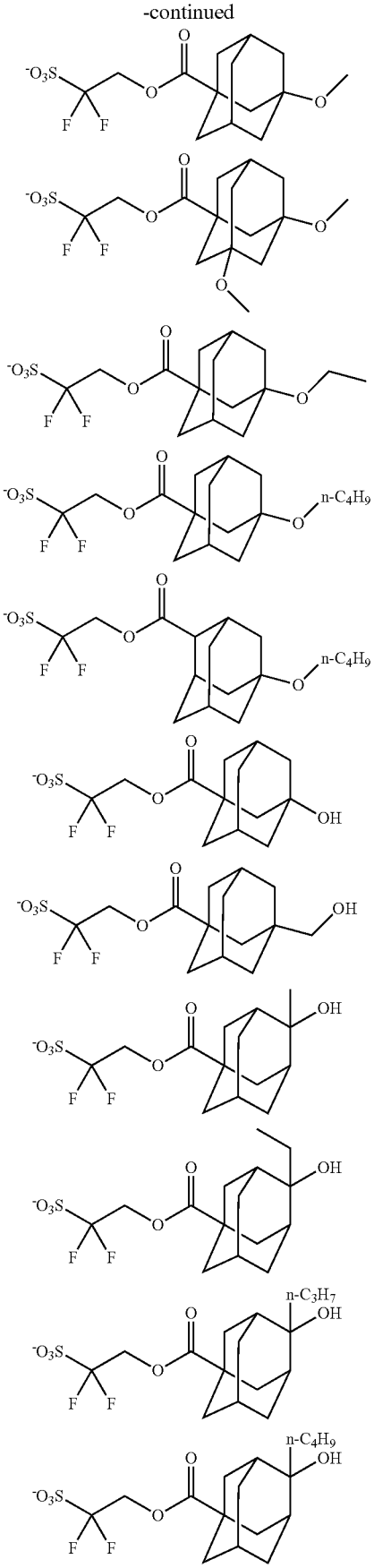

75
-continued
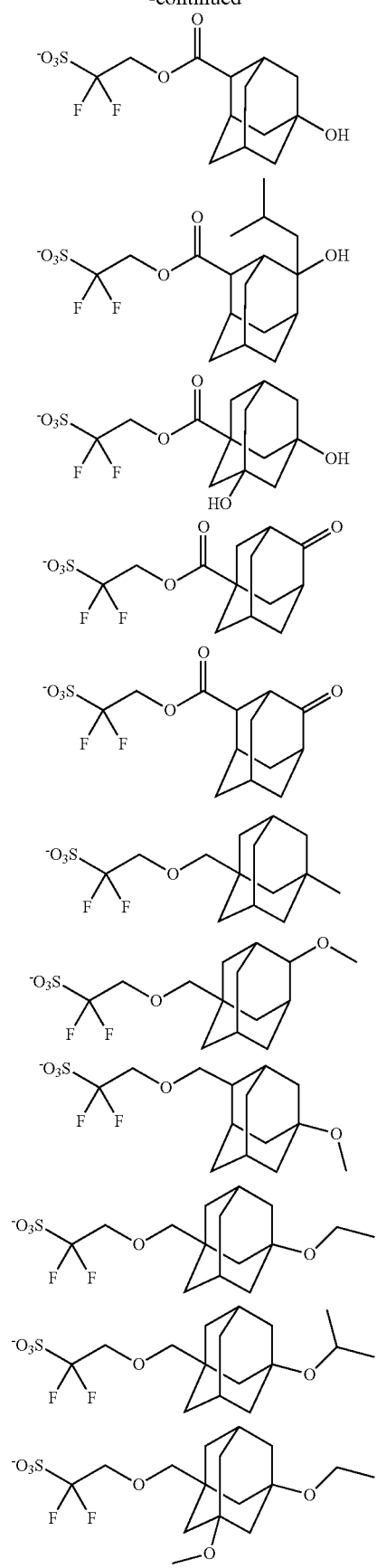
76
-continued
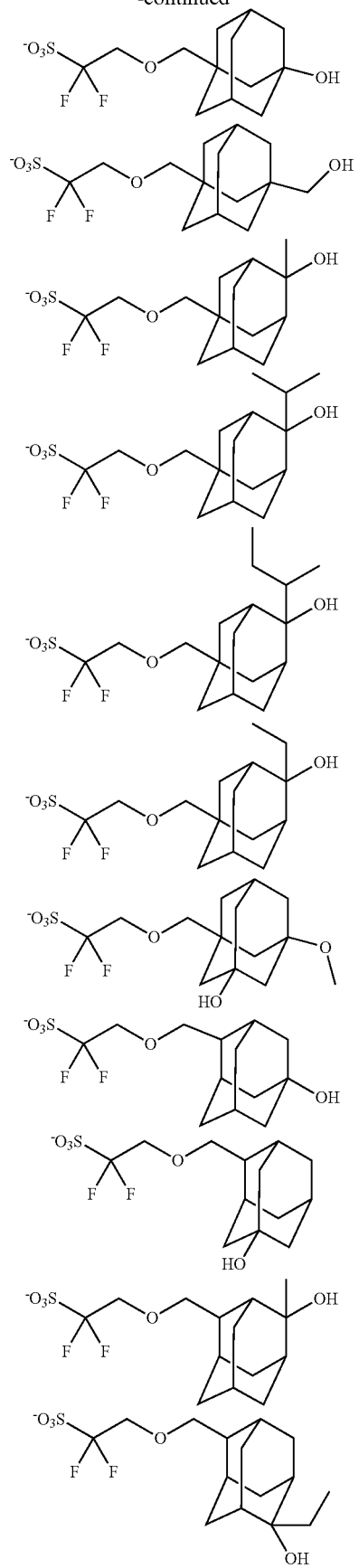

-continued

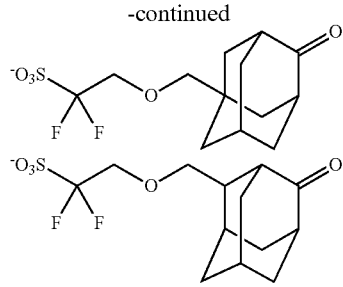

Among them, preferred are the following sulfonic anions.

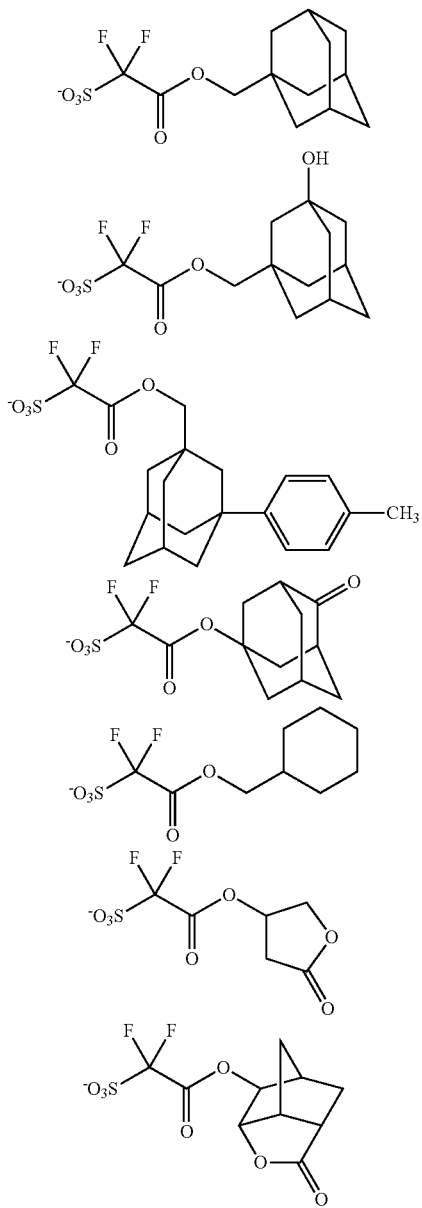

Examples of the organic cation represented by $Z^+$ in the salt represented by the formula (B1) include the same as those of SALT (I), and a sulfonium cation and an iodonium cation are preferable, and an arylsulfonium cation is more preferable. A triphenylsulfonium cation is especially preferable.

Examples of the salt represented by the formula (B1) include a salt wherein the anion is any one of the above-mentioned anions and the cation is any one of the above-mentioned cations. Preferable examples thereof include a salt formed by combining any one of anions represented by the formulae (b1-1-1) to (b-1-9) with the cation represented by the formula (b2-1-1), and a salt formed by combining any one of anions represented by the formulae (b1-1-3) to (b1-1-5) with the cation represented by the formula (b2-3).

Preferred are the salts represented by the formulae (B1-1) to (B1-17), and more preferred are the salts represented by the formulae (B1-1), (B1-2), (B1-6), (B1-11), (B1-12), (B1-13) and (B1-14).

(B1-1)

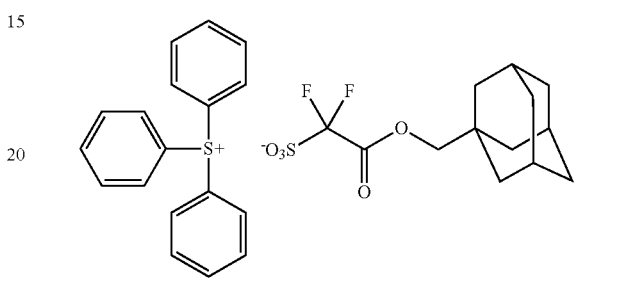

(B1-2)

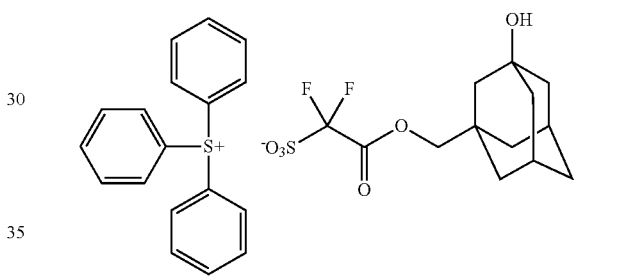

(B1-3)

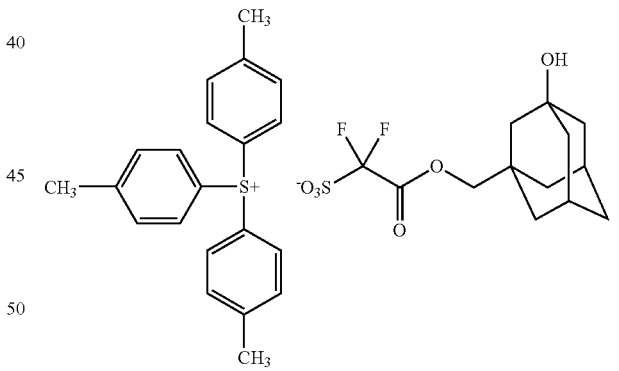

(B1-4)

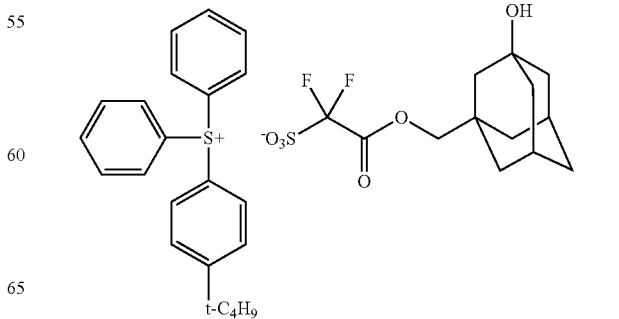

(B1-5)
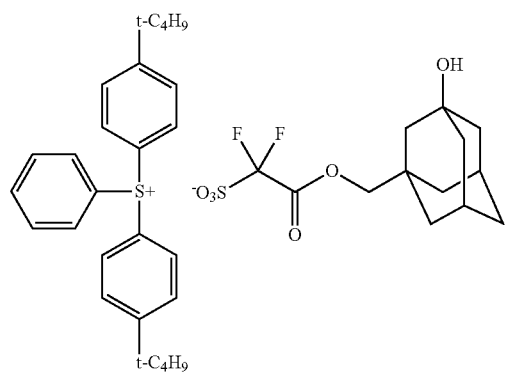
(B1-6)
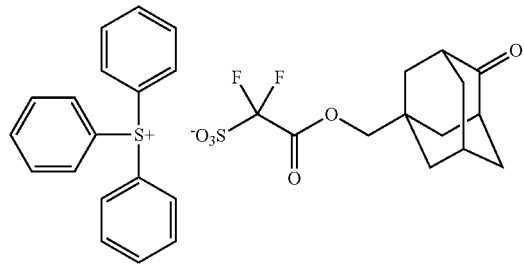
(B1-7)
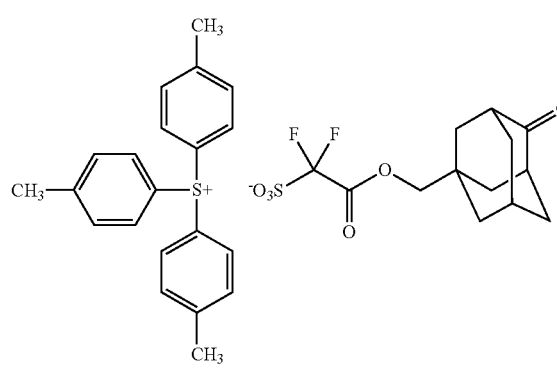
(B1-8)
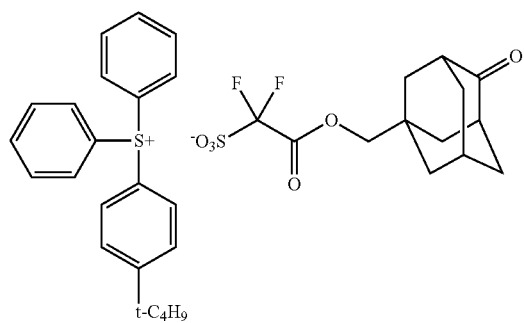
(B1-9)
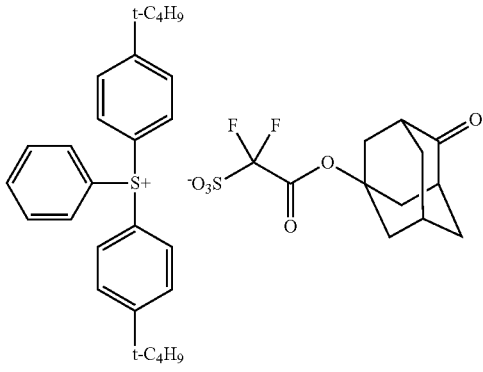
(B1-10)
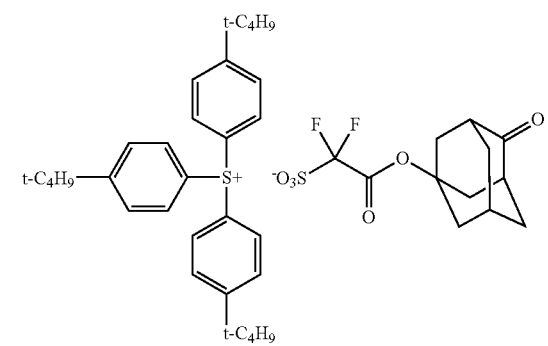
(B1-11)
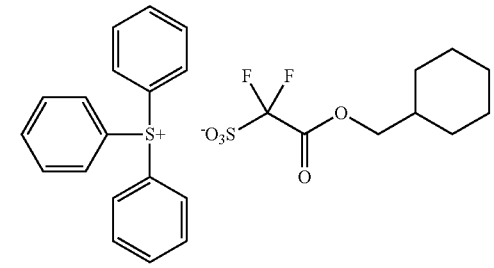
(B1-12)
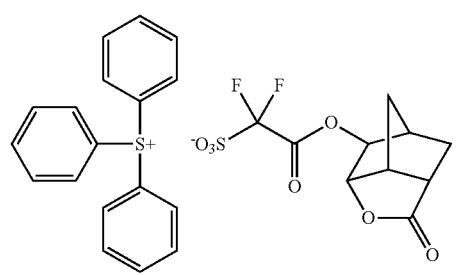
(B1-13)

(B1-14)

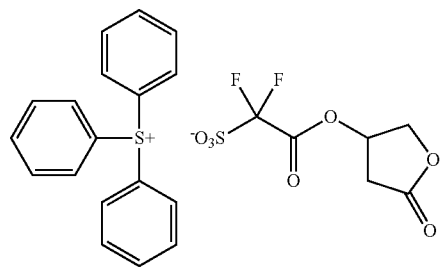

(B1-15)

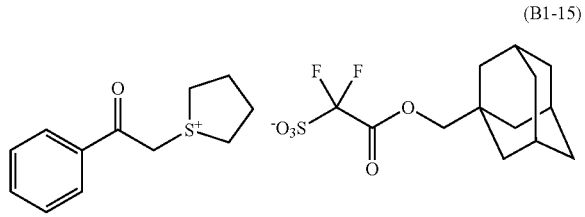

(B1-16)

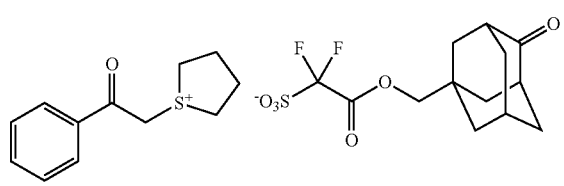

(B1-17)

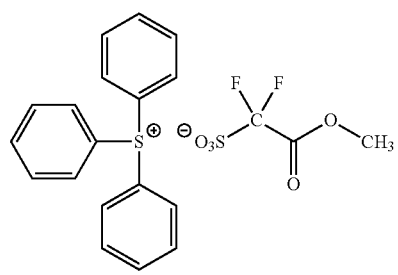

The amount of the acid generator other than SALT (I) in the photoresist composition of the present invention is usually 1 part by weight or more, and preferably 3 parts by weight or more per 100 parts by weight of the resin. The amount of the acid generator other than SALT (I) in the photoresist composition of the present invention is usually 30 parts by weight or less, and preferably 25 parts by weight or less per 100 parts by weight of the resin.

The resin will be illustrated below.

The resin has an acid-labile group and is insoluble or poorly soluble in an alkali aqueous solution but becomes soluble in an alkali aqueous solution by the action of an acid. The resin has a structural unit derived from a compound having an acid-labile group, and can be produced by polymerizing one or more compounds having an acid-labile group.

In this specification, "an acid-labile group" means a group capable of being eliminated by the action of an acid.

Examples of the acid-labile group include a group represented by the formula (I):

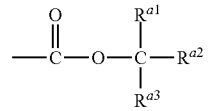

(1)

wherein $R^{a1}$, $R^{a2}$ and $R^{a1}$ independently each represent an aliphatic hydrocarbon group or a saturated cyclic hydrocarbon group, or $R^{a1}$ and $R^{a2}$ are bonded each other to form a ring together with a carbon atom to which $R^{a1}$ and $R^{a2}$ are bonded.

Examples of the aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The saturated cyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

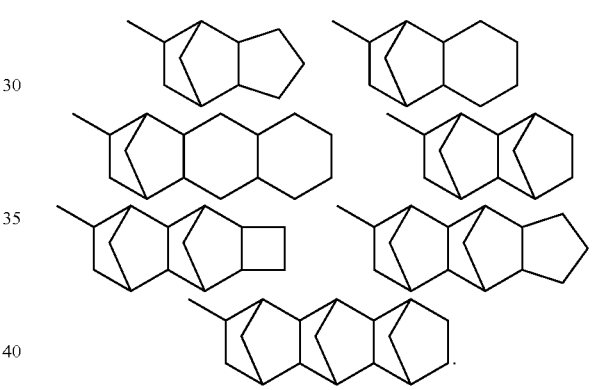

The saturated cyclic hydrocarbon group preferably has 3 to 20 carbon atoms.

Examples of the ring formed by bonding $R^{a1}$ and $R^{a2}$ each other include the following groups and the ring preferably has 3 to 20 carbon atoms, and the more preferably has 3 to 12 carbon atoms.

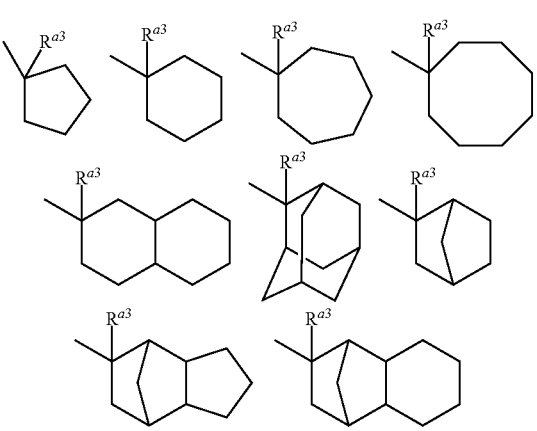

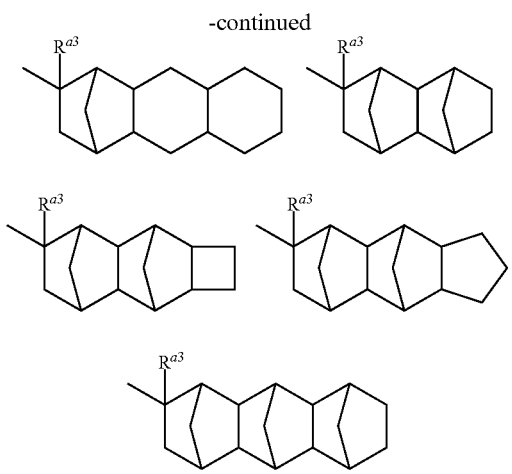

wherein $R^{a3}$ is the same as defined above.

The group represented by the formula (I) wherein $R^{a1}$, $R^{a2}$ and $R^{a3}$ independently each represent a C1-C8 alkyl group such as a tert-butyl group, the group represented by the formula (I) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (I) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The compound having an acid-labile group is preferably an acrylate monomer having an acid-labile group in its side chain or a methacryalte monomer having an acid-labile group in its side chain.

Preferable examples thereof include (meth)acrylate monomers having C5-C20 saturated cyclic hydrocarbon group. As (meth)acrylate monomers having C5-C20 saturated cyclic hydrocarbon group, preferred are monomers represented by the formulae (a1-1) and (a1-2):

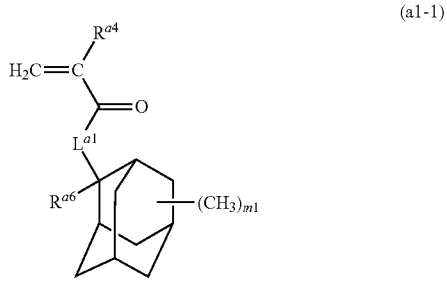

(a1-1)

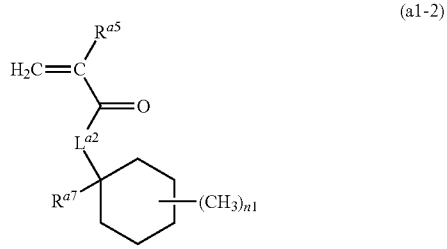

(a1-2)

wherein $R^{a4}$ and $R^{a5}$ independently represent a hydrogen atom or a methyl group, $R^{a6}$ and $R^{a7}$ independently represents a C1-C8 aliphatic hydrocarbon group or a C3-C10 saturated cyclic hydrocarbon group, $L^{a1}$ and $L^{a2}$ independently represents *—O— or *—O—$(CH_2)_{k1}$—CO—O— in which * represents a binding position to —CO—, and k1 represents an integer of 1 to 7, m1 represents an integer of 0 to 14 and n1 represents an integer of 0 to 10.

The aliphatic hydrocarbon group preferably has 1 to 6 carbon atoms, and the saturated cyclic hydrocarbon group preferably has 3 to 8 carbon atoms and more preferably 3 to 6 carbon atoms.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include the followings.

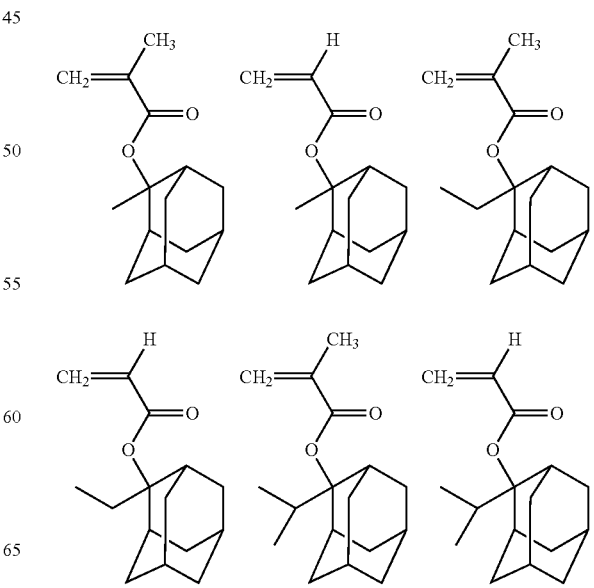

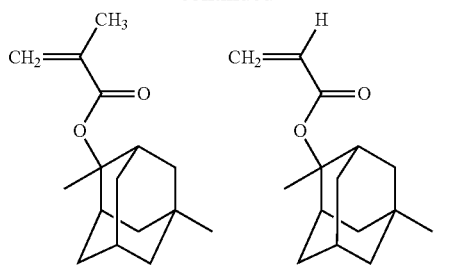
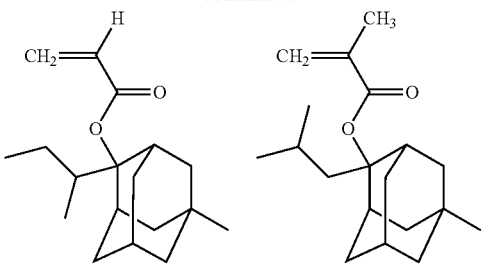
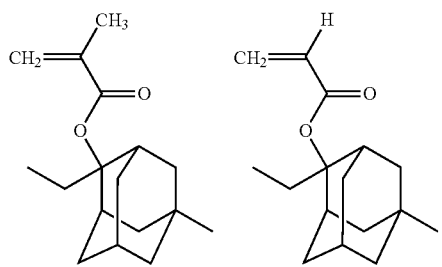
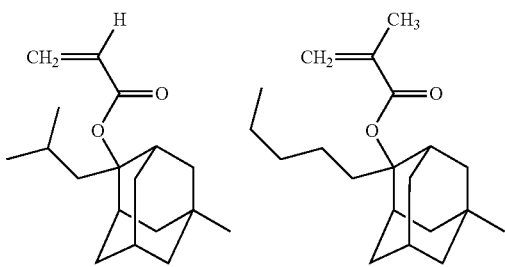
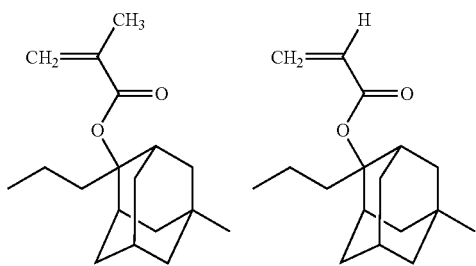
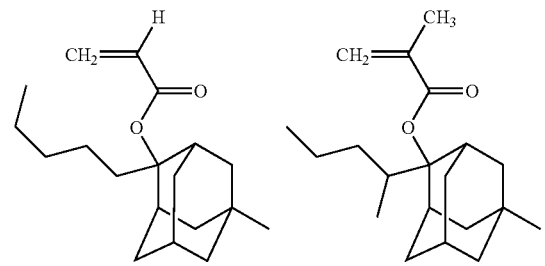
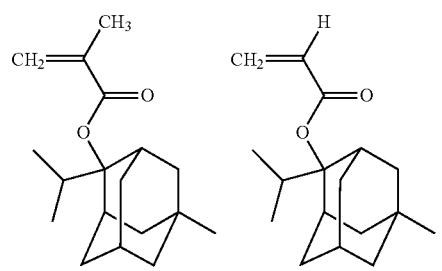
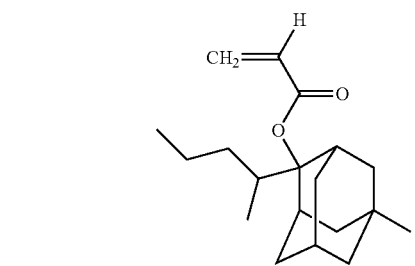
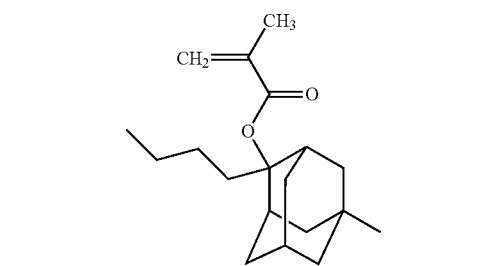
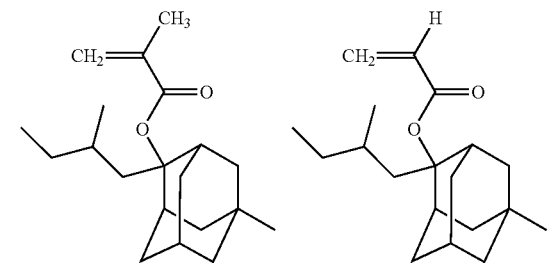
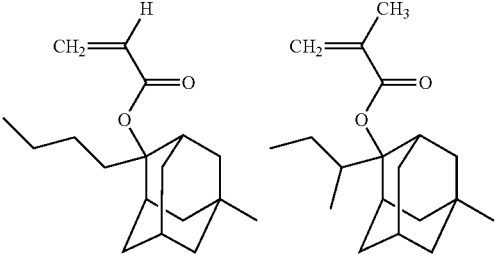
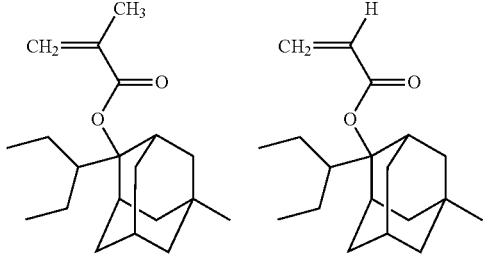

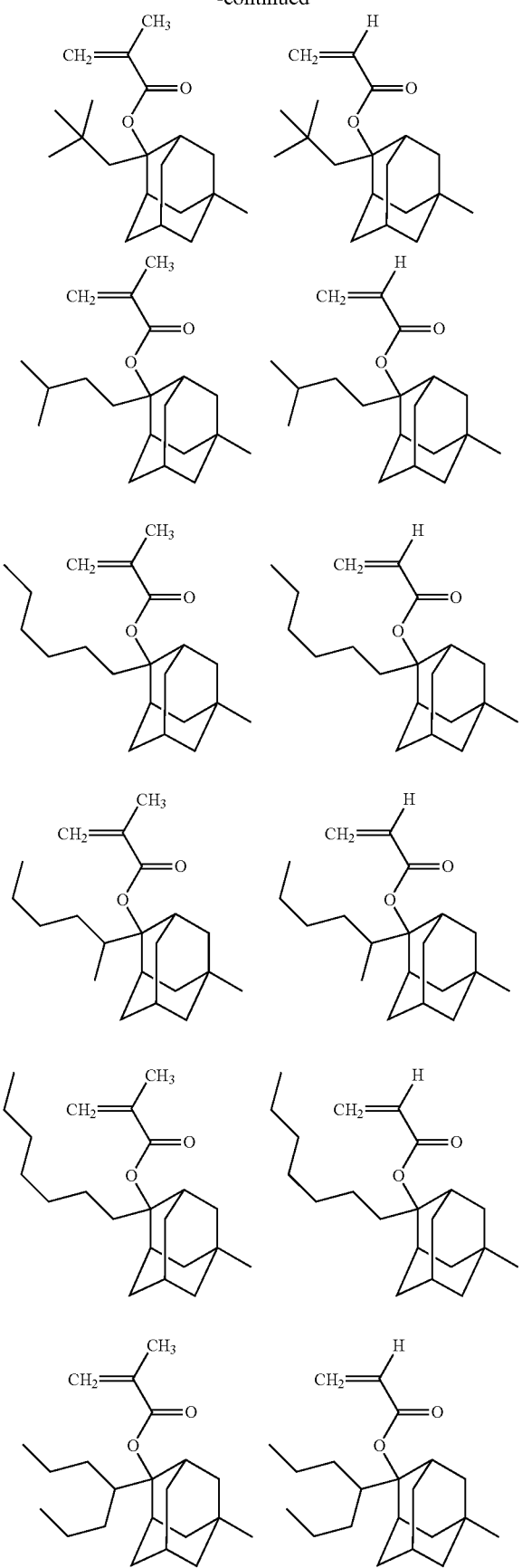
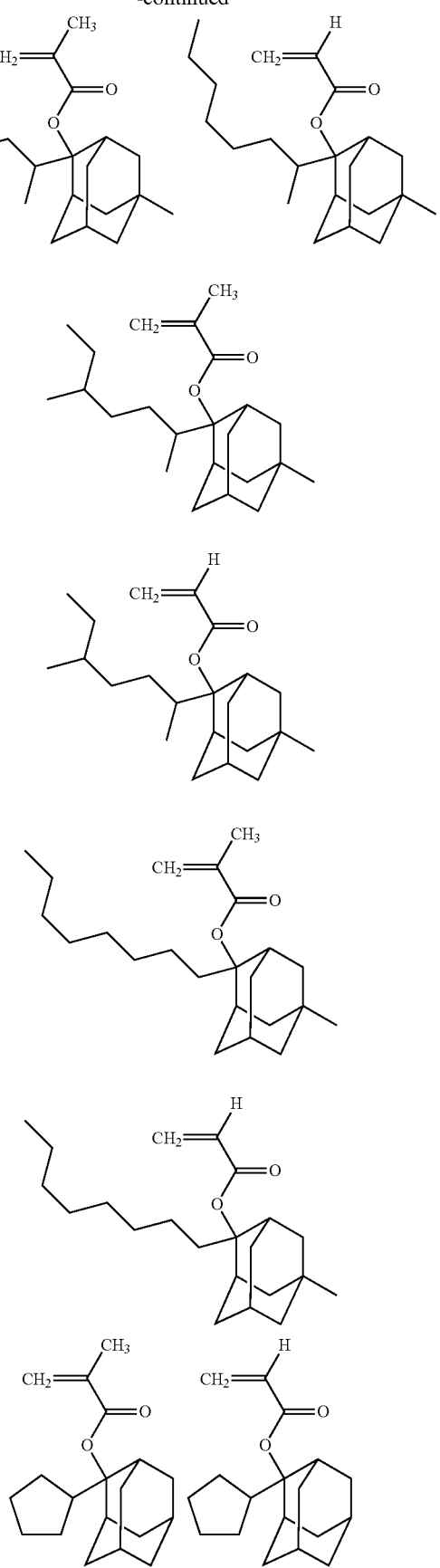

-continued
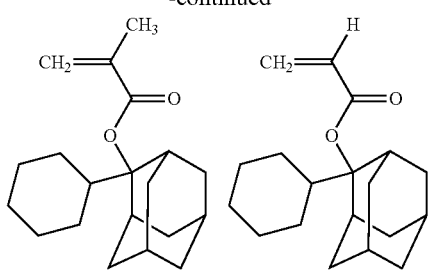
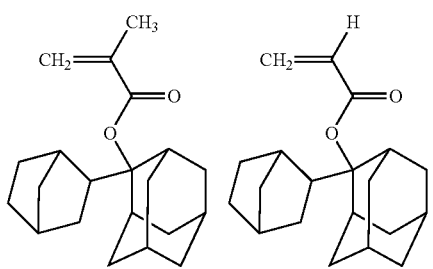
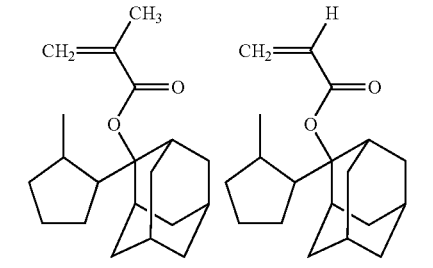
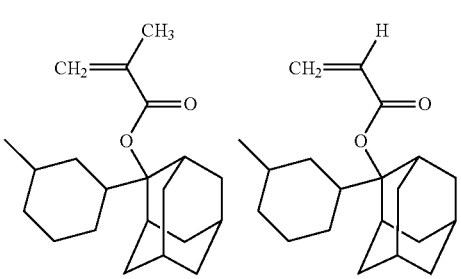
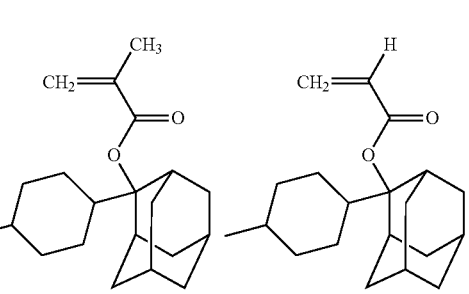
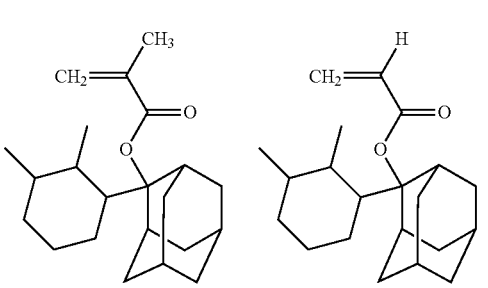
-continued
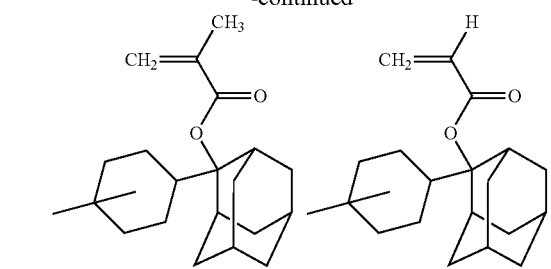
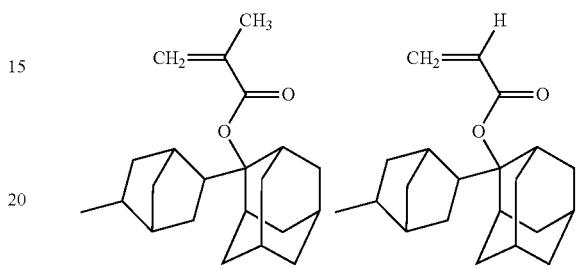
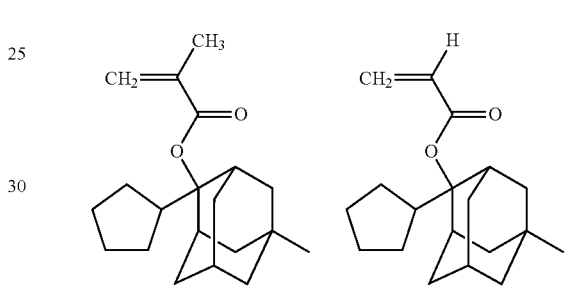
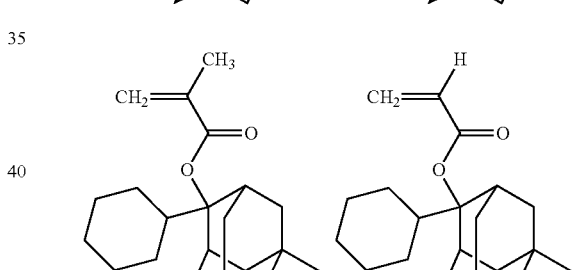
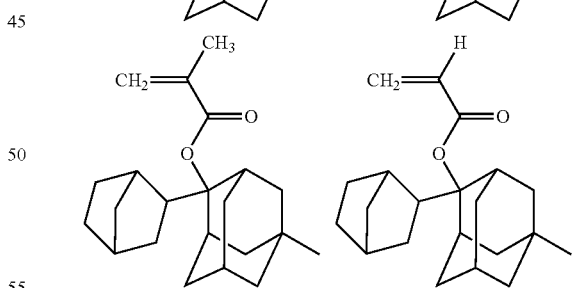
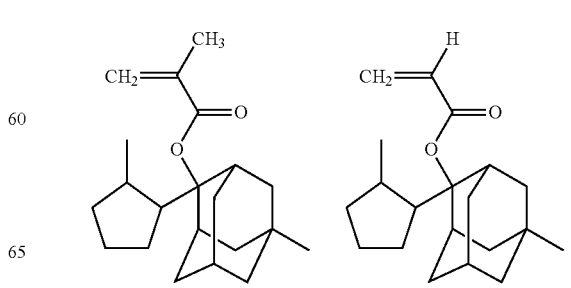

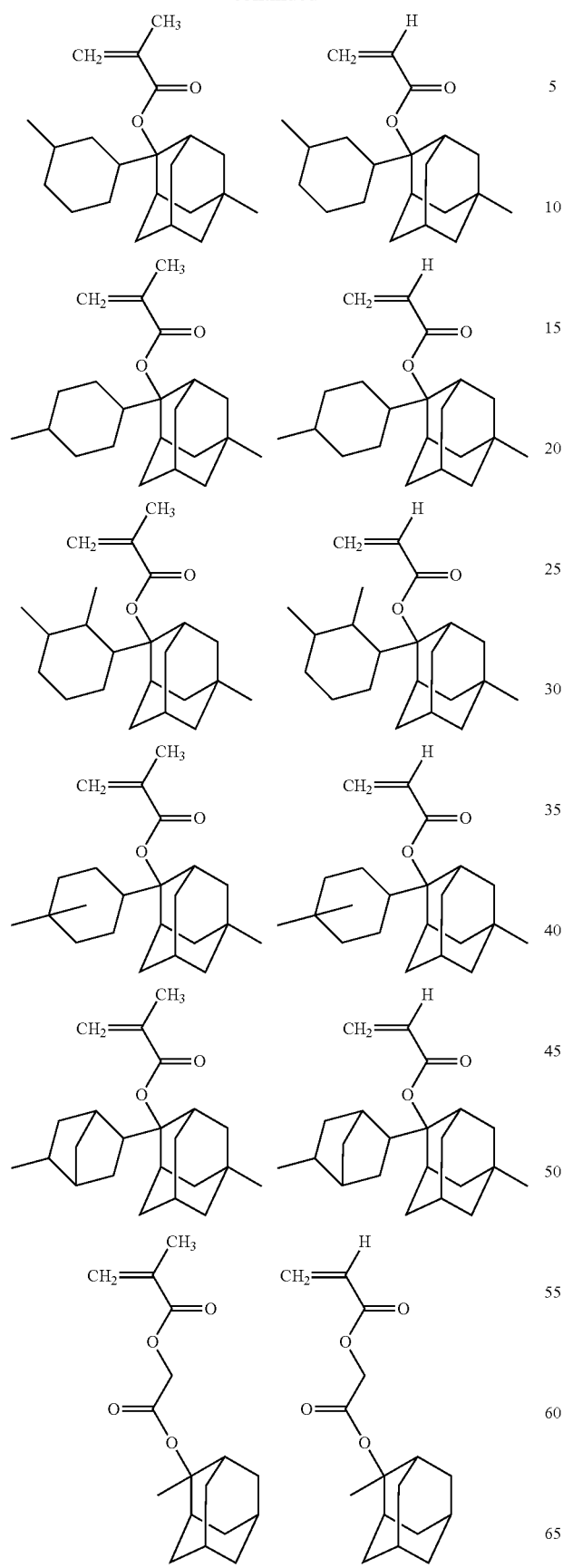
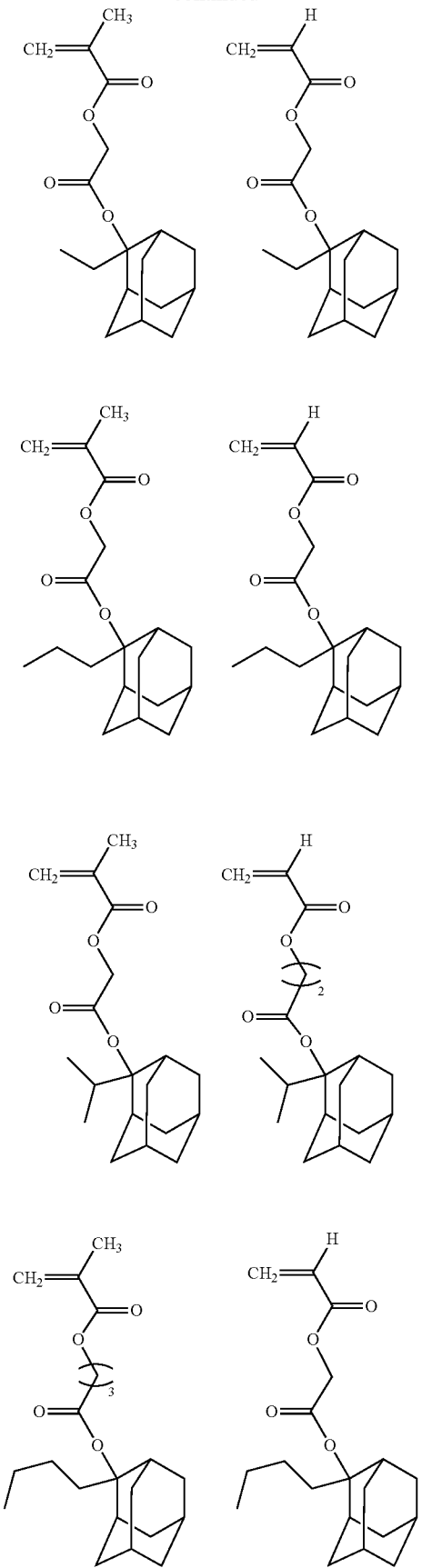

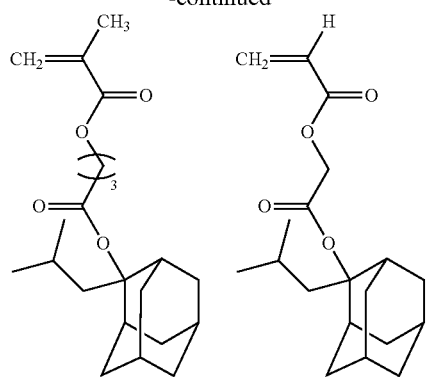
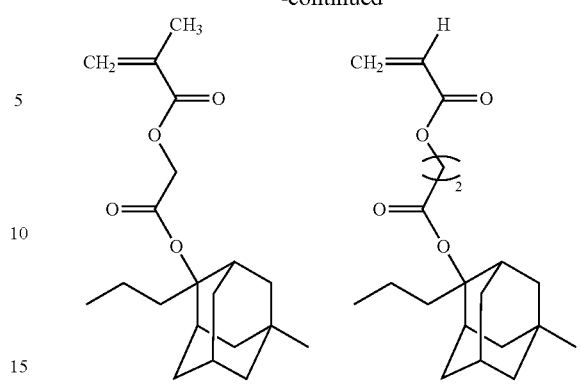
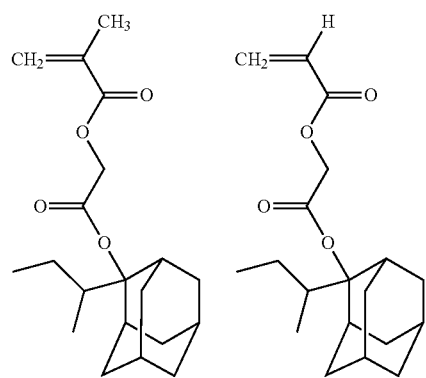
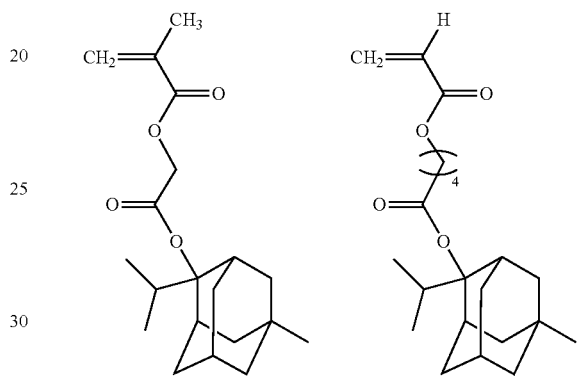
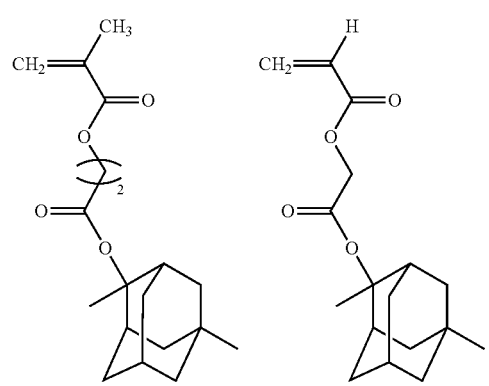
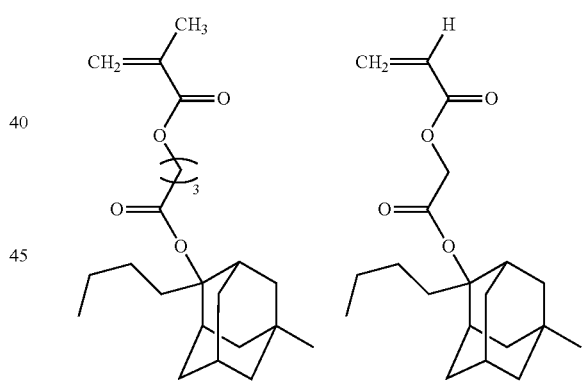
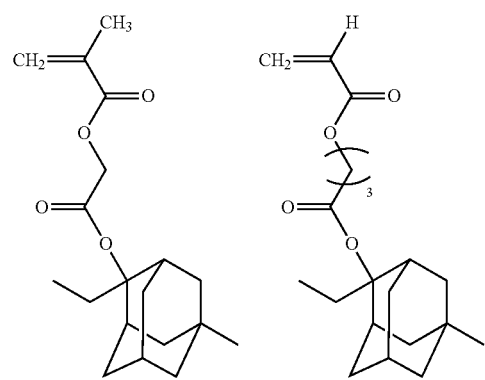
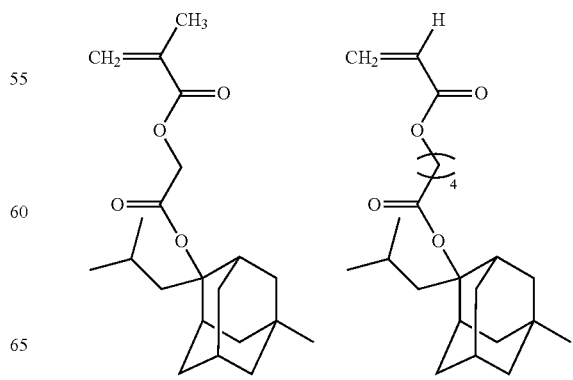

95
-continued
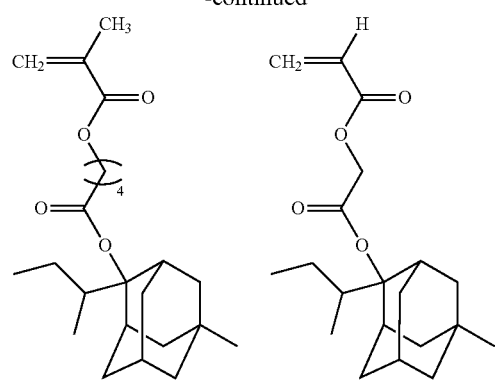
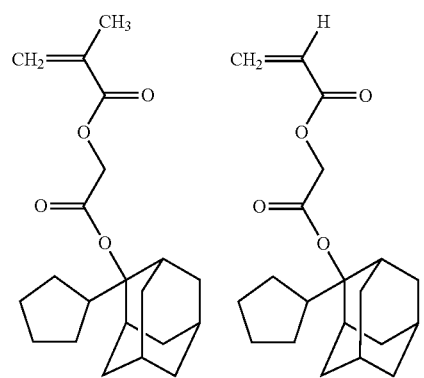
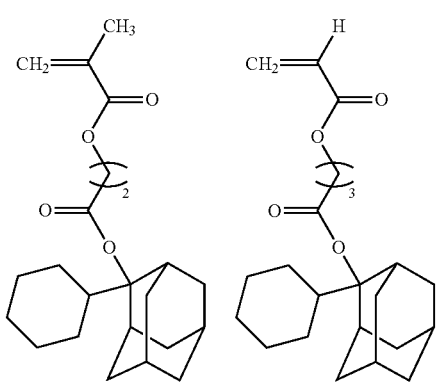
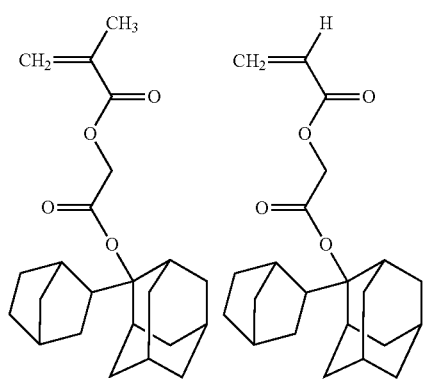
96
-continued
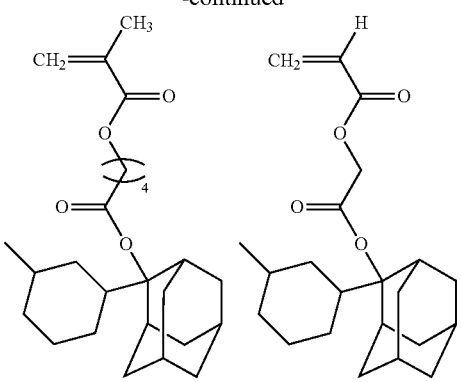
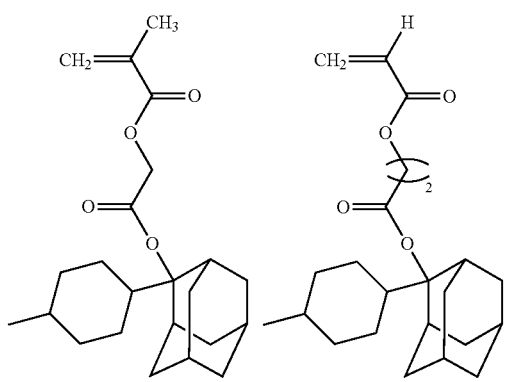
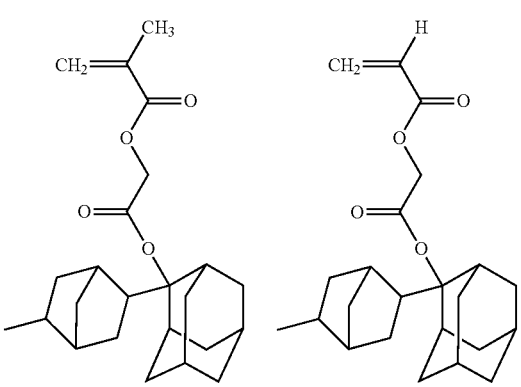
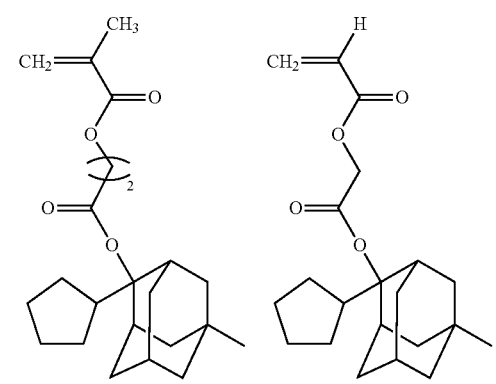

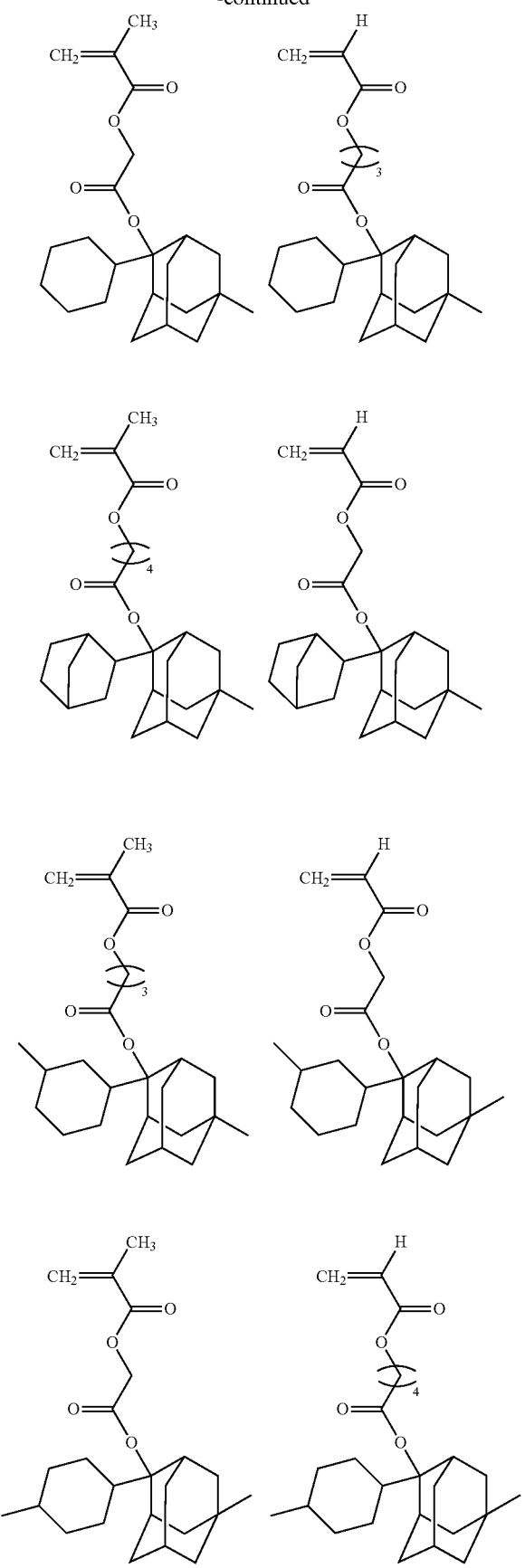

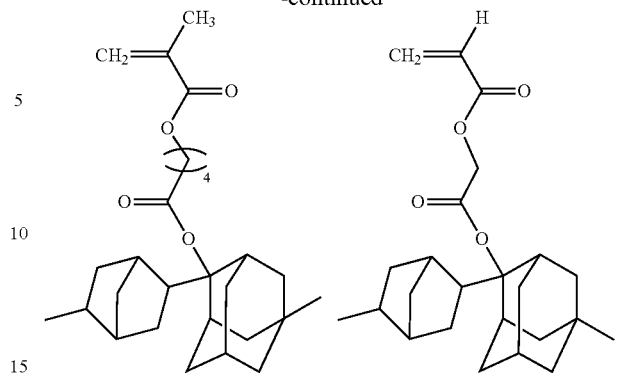

Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a1-2) include the followings.

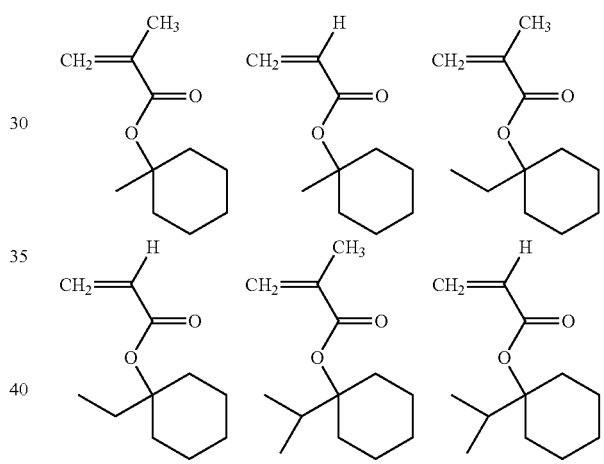

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from a compound having an acid-labile group in the resin is usually 10 to 95% by mole, preferably 15 to 90% by mole and more preferably 20 to 85% by mole based on 100% by mole of all the structural units of the resin.

Other examples of the compound having an acid-labile group include a monomer represented by the formula (a1-3):

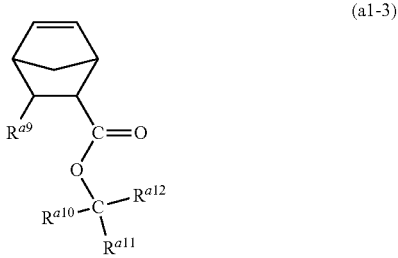

(a1-3)

wherein $R^{a9}$ represents a hydrogen atom, a C1-C3 aliphatic hydrocarbon group which can have one or more substituents, a carboxyl group, a cyano group or a —COOR$^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ independently represent a C1-C12 aliphatic hydrocarbon group or a C3-C12 saturated cyclic hydrocarbon group, or $R^{a10}$ and $R^{a11}$ are bonded each other to form a ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the substituent include a hydroxyl group. Examples of the C1-C3 aliphatic hydrocarbon group which can have one or more substituents include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When the resin has a structural unit derived from the monomer represented by the formula (a1-3), the photoresist composition having excellent resolution and higher dry-etching resistance tends to be obtained.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-4):

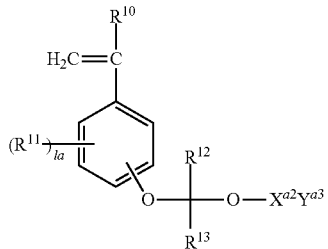

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, la represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N($R^c$)— wherein $R^c$ represents a hydrogen atom or a C1-C6 alkyl group, and $Y^{a3}$ represents a C1-C12 aliphatic hydrocarbon group, a C3-C18 saturated cyclic hydrocarbon group or a C6-C18 aromatic hydrocarbon group, and the C1-C12 aliphatic hydrocarbon group, the C2-C18 saturated cyclic hydrocarbon group and the C6-C18 aromatic hydrocarbon group can have one or more substituents.

Examples of the halogen atom include a fluorine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, and a C3-C12 saturated cyclic hydrocarbon group such as a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group.

Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

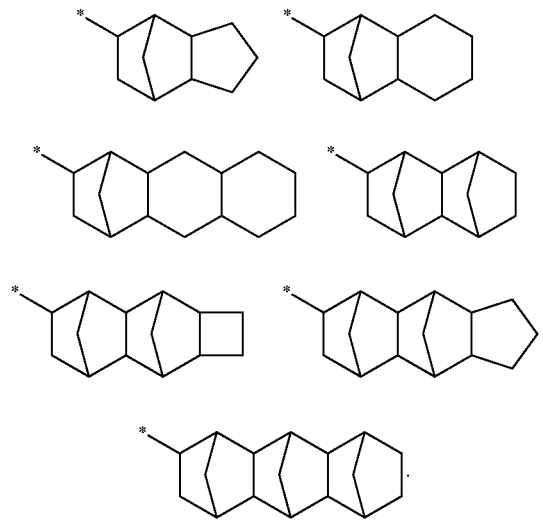

Examples of the C6-C18 aromatic hydrocarbon group include a phenyl group, a naphthyl group, an anthryl group, a p-methylphenyl group, a p-tert-butylphenyl group and a p-adamantylphenyl group.

Examples of the monomer represented by the formula (a1-4) include the followings.

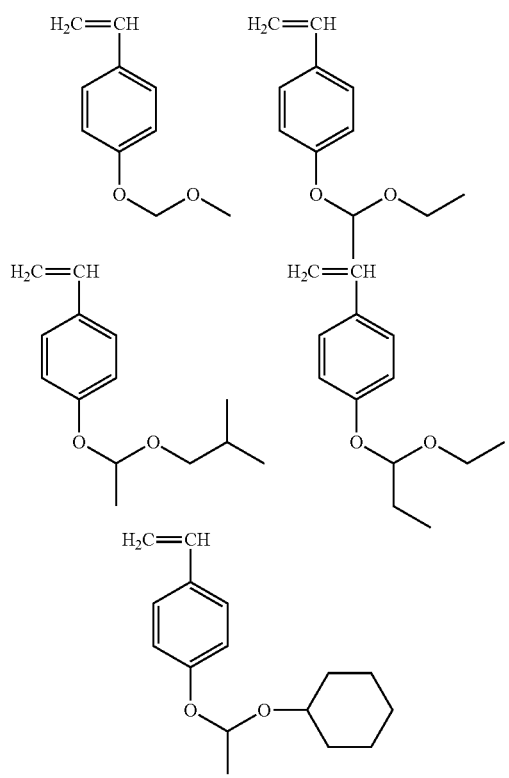
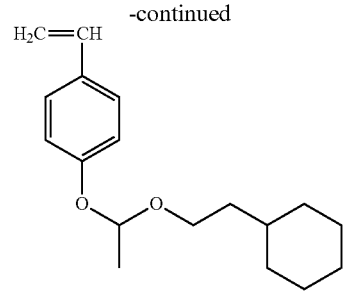
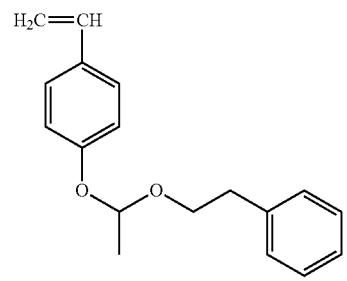
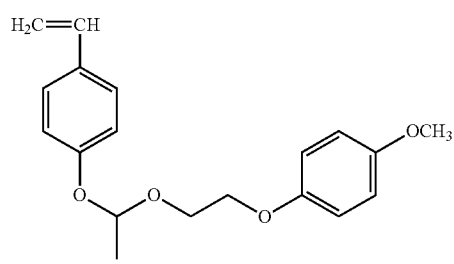
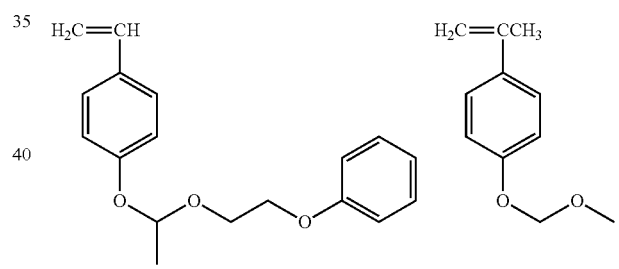
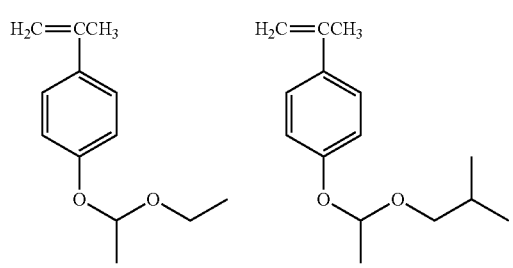
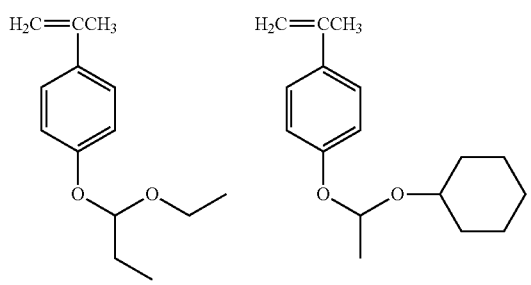

103
-continued
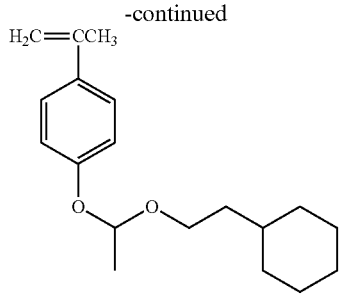
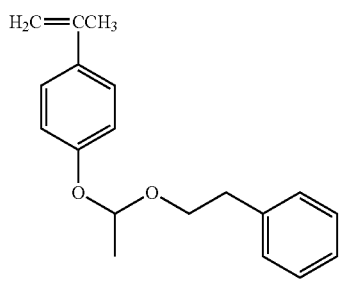
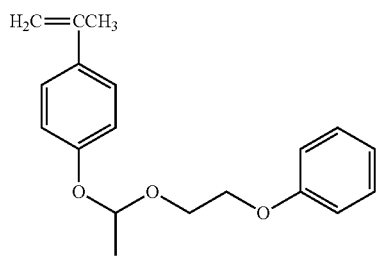
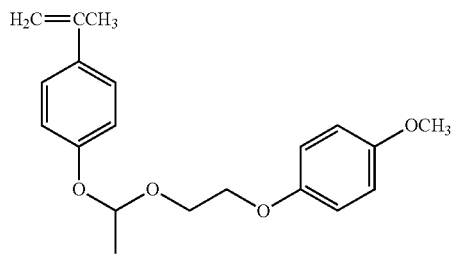
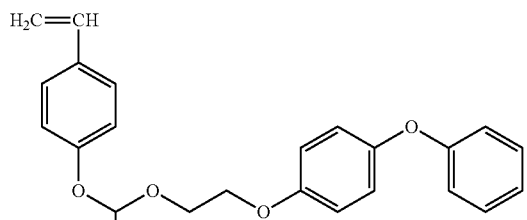
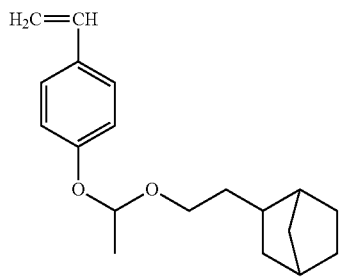
104
-continued
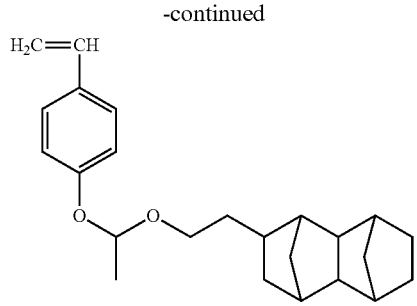
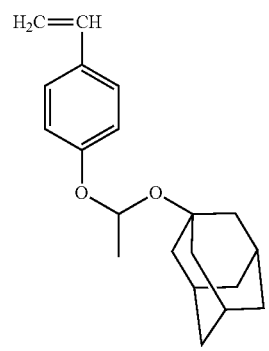
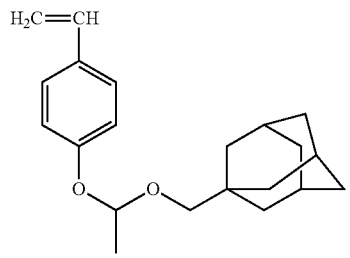
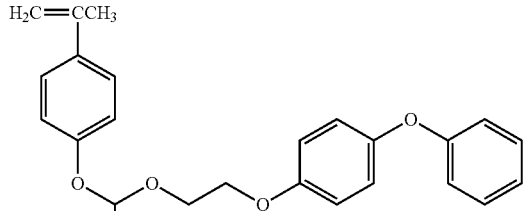
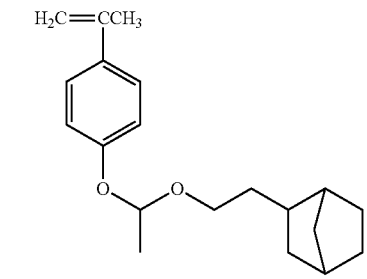
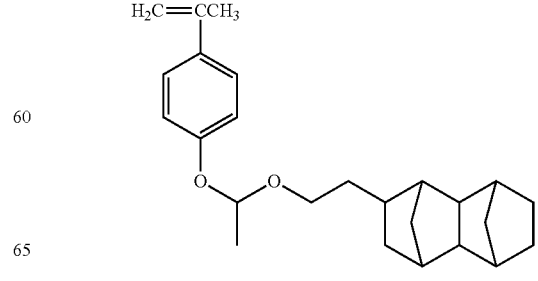

105
-continued
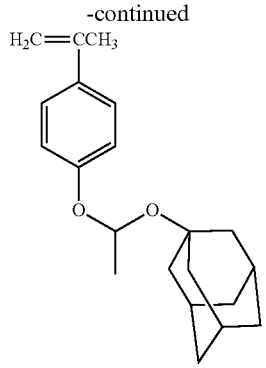
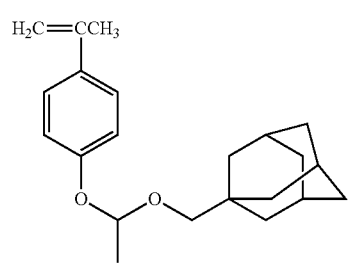
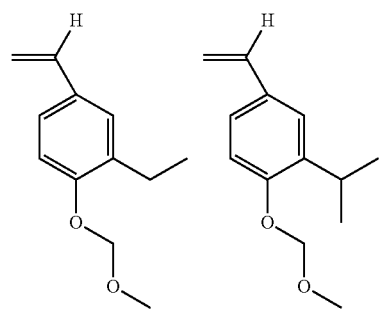
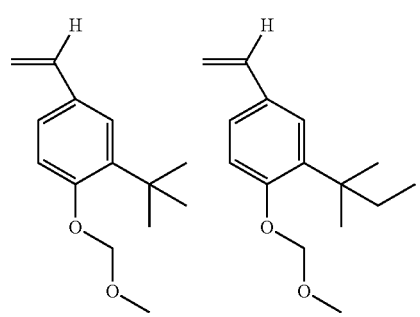
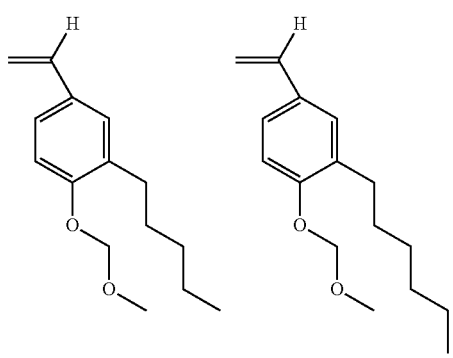
106
-continued
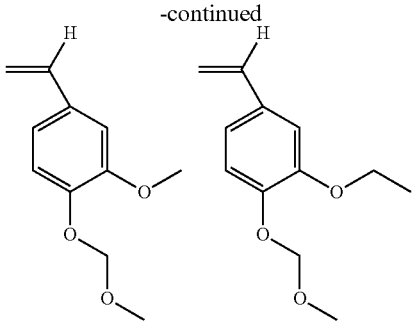
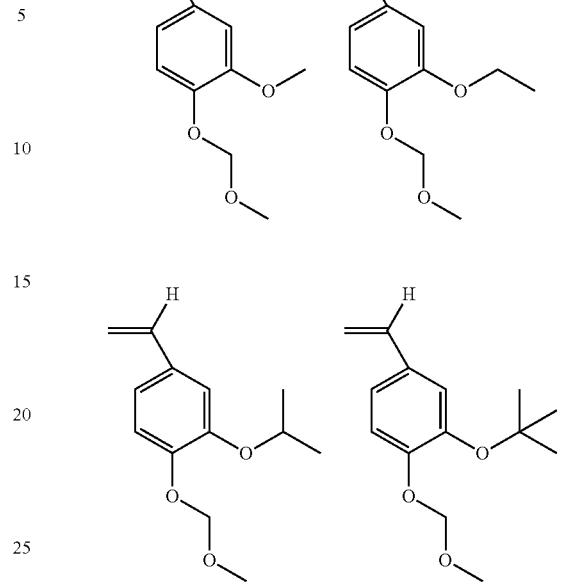
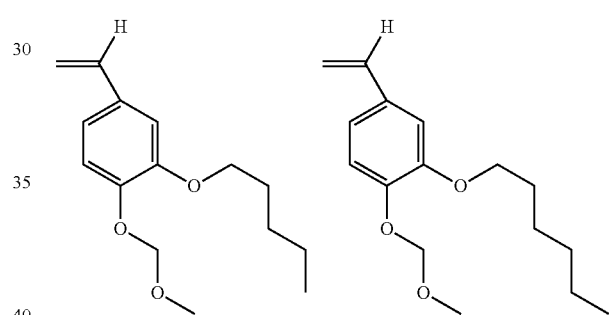
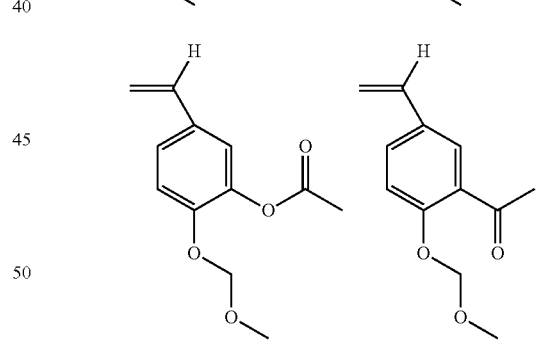
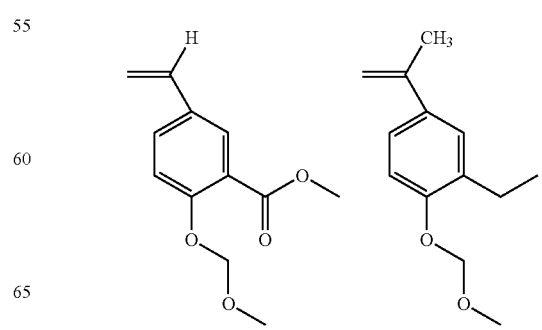

107
-continued
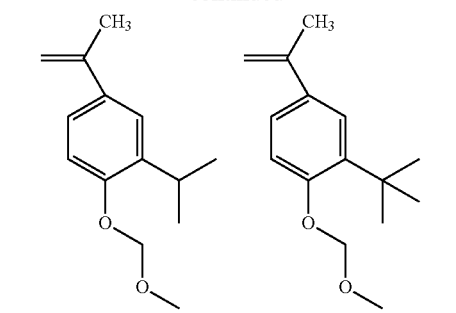
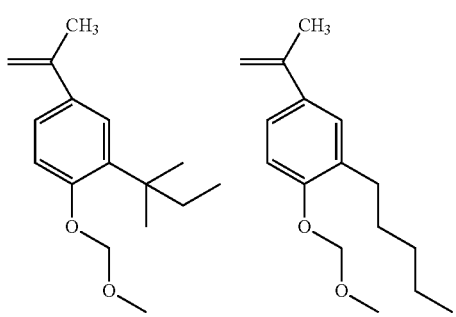
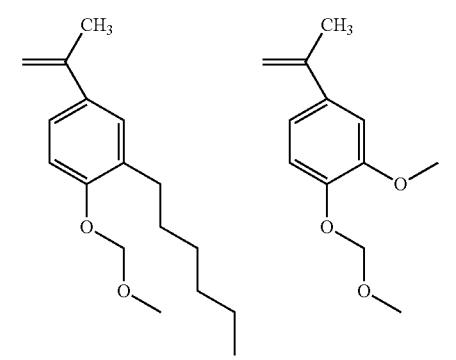
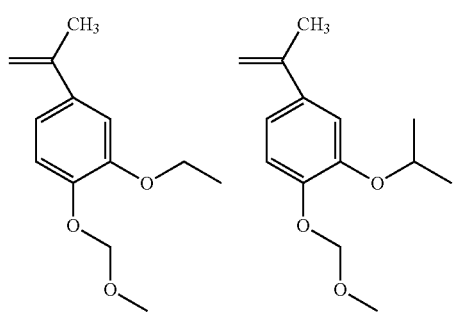
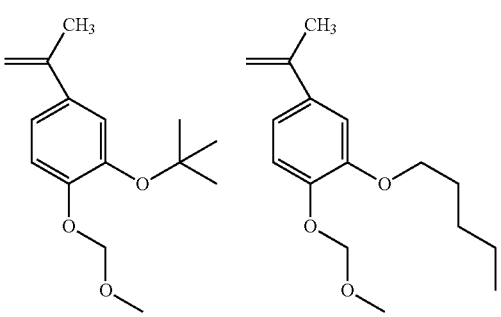
108
-continued
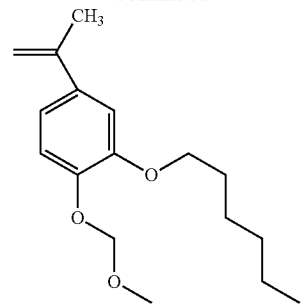
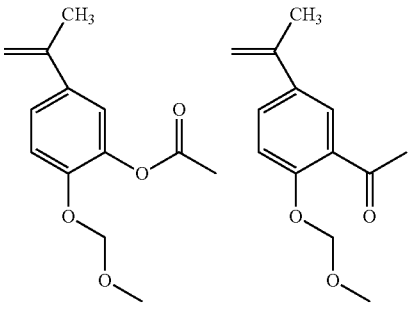
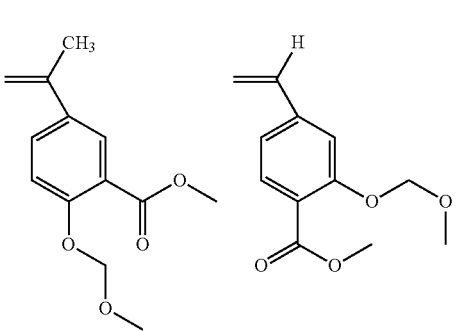
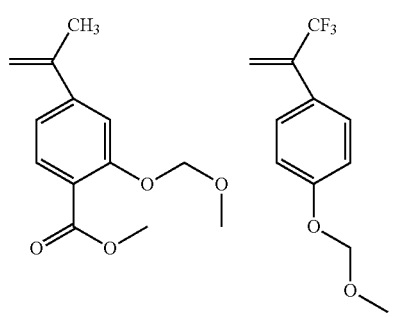
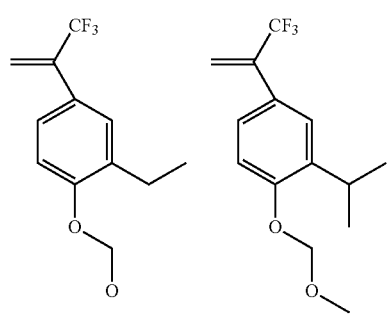

-continued

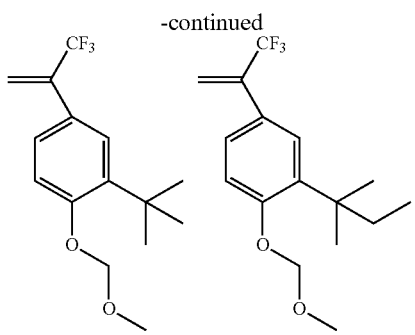

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

The resin can have two or more kinds of structural units derived from the compounds having an acid-labile group.

The resin preferably contains the structural unit derived from the compound having an acid-labile group and a structural unit derived from the compound having no acid-labile group. The resin can have two or more kinds of structural units derived from the compounds having no acid-labile group. When the resin contains the structural unit derived from the compound having an acid-labile group and the structural unit derived from the compound having no acid-labile group, the content of the structural unit derived from the compound having an acid-labile group is usually 10 to 80% by mole and preferably 20 to 60% by mole based on total molar of all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The compound having no acid-labile group preferably contains one or more hydroxyl groups or a lactone ring. When the resin contains the structural unit derived from the compound having no acid-labile group and having one or more hydroxyl groups or a lactone ring, a photoresist composition having good resolution and adhesiveness of photoresist to a substrate tends to be obtained.

Examples of the compound having no acid-labile group and having one or more hydroxyl groups include a monomer represented by the formula (a2-0):

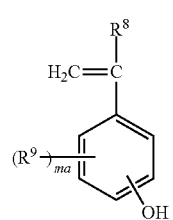

(a2-0)

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents
an integer of 0 to 4, and
a monomer represented by the formula (a2-1):

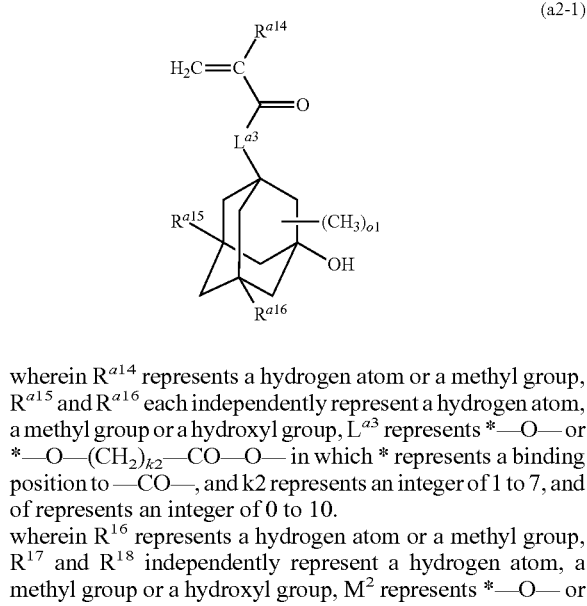

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.
wherein $R^{16}$ represents a hydrogen atom or a methyl group, $R^{17}$ and $R^{18}$ independently represent a hydrogen atom, a methyl group or a hydroxyl group, $M^2$ represents *—O— or *—O—$(CH_2)_{k2}$—CO—O— in which * represents a binding position to —CO—, and k2 represents an integer of 1 to 7, and c represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) and the structural unit derived from the compound having an acid generator can be produced, for example, by polymerizing the compound having an acid generator and a monomer obtained by protecting a hydroxyl group of the monomer represented by the formula (a2-0) with an acetyl group followed by conducting deacetylation of the obtained polymer with a base.

Examples of the monomer represented by the formula (a2-0) include the followings.

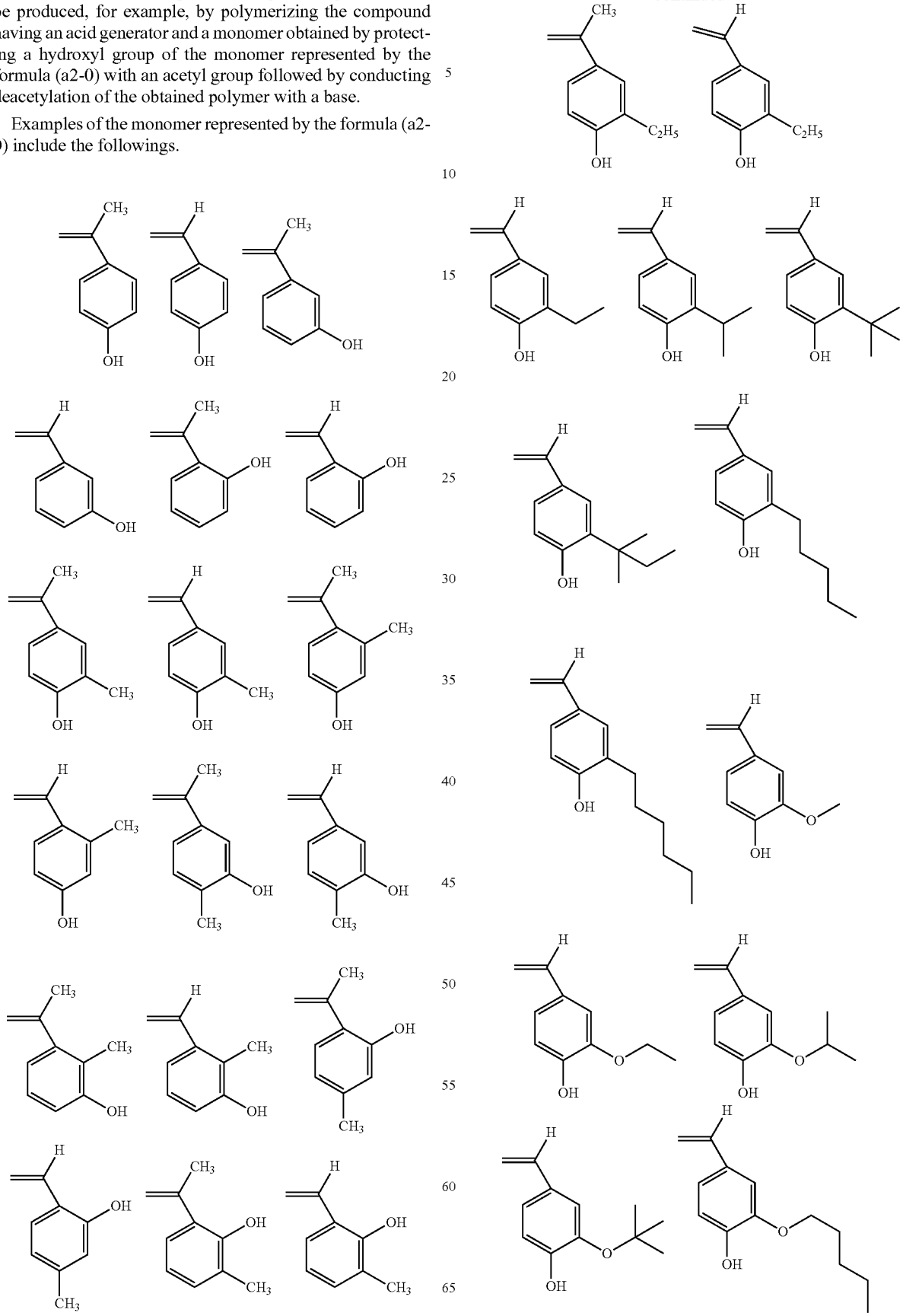

-continued

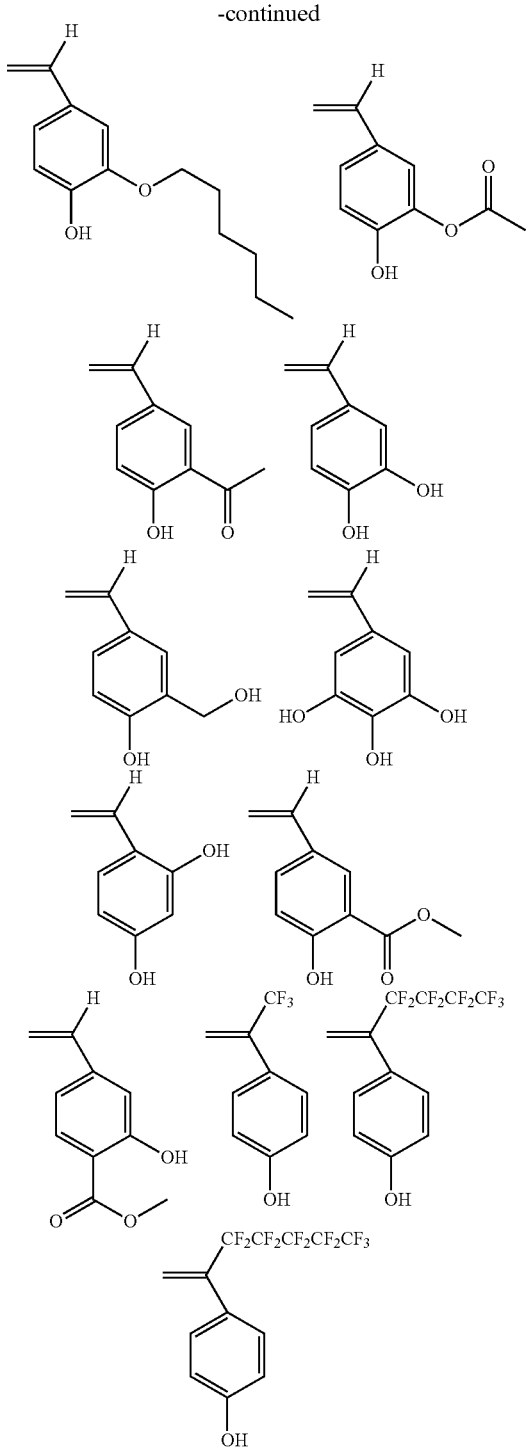

Among them, preferred are 4-hydroxystyrene and 4-hydroxy-α-methylstyrene.

When the resin contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a1}$ is preferably *—O— or *—O—$(CH_2)_{f2}$—CO—O— in which * represents a binding position to —CO—, and f2 represents an integer of 1 to 4, and is more preferably *—O—, and o1 is preferably 0, 1, 2 or 3 and is more preferably 0 or 1.

Examples of the monomer represented by the formula (a2-1) include the followings, and 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate and 1-(3,5-dihydroxy-1-adamantyloxycarbonyl)methyl methacrylate are preferable, and 3-hydroxy-1-adamantyl methacrylate and 3,5-dihydroxy-1-adamantyl methacrylate are more preferable.

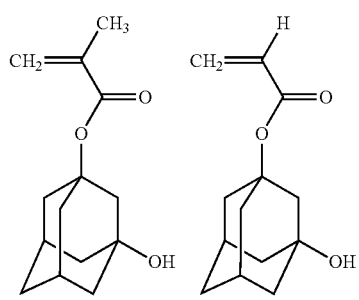

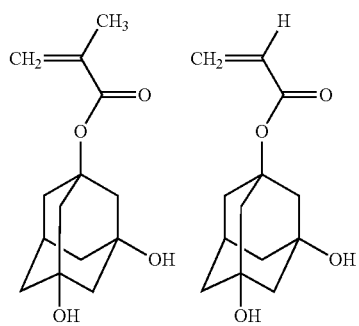

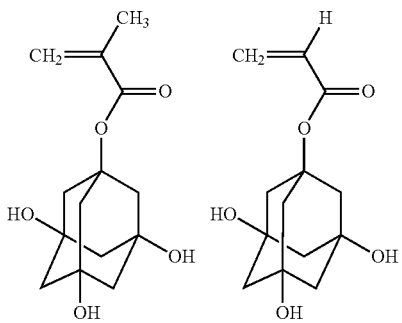

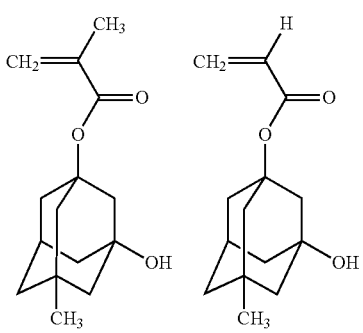

115
-continued
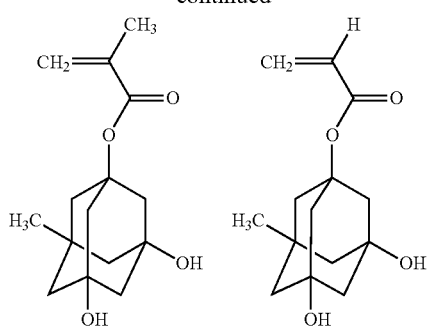
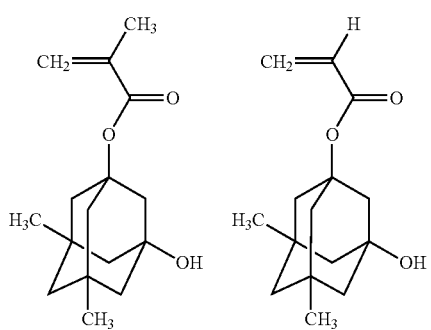
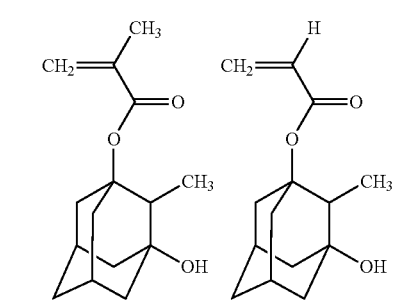
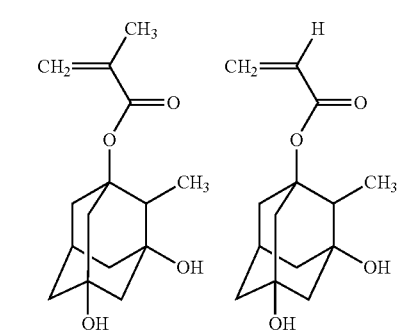
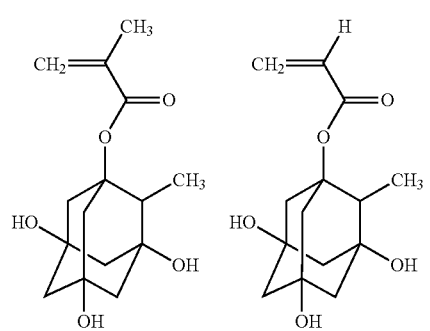
116
-continued
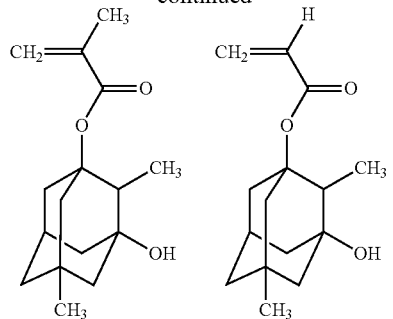
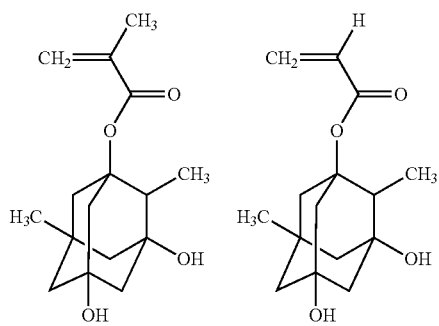
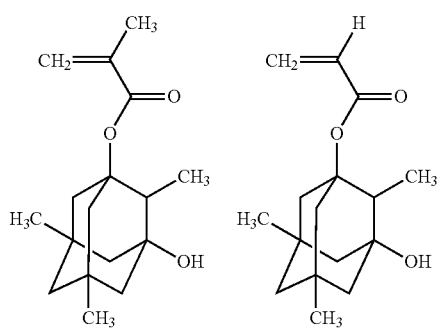
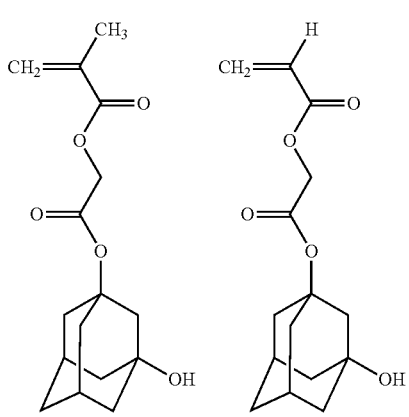

117
-continued
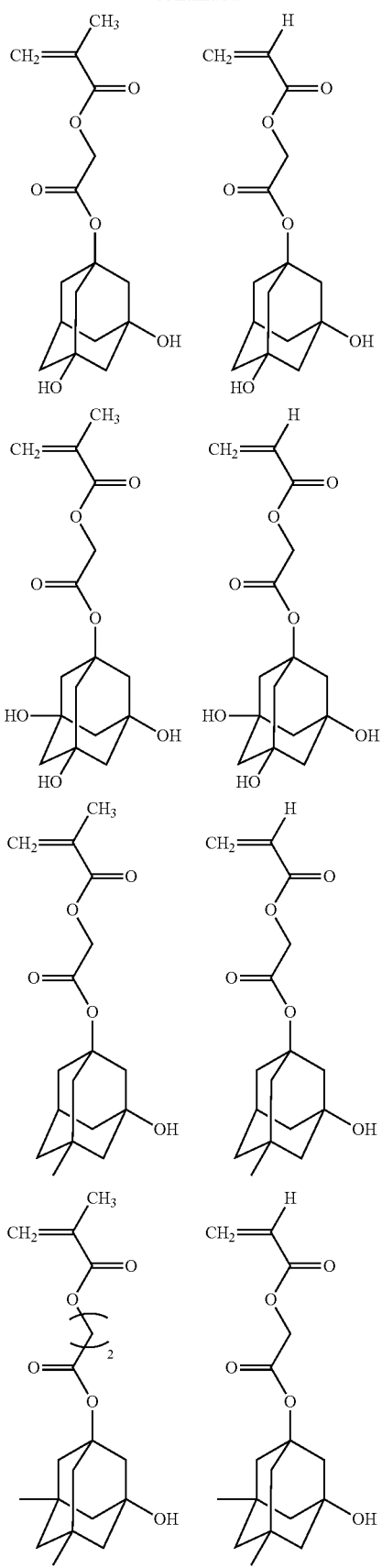
118
-continued
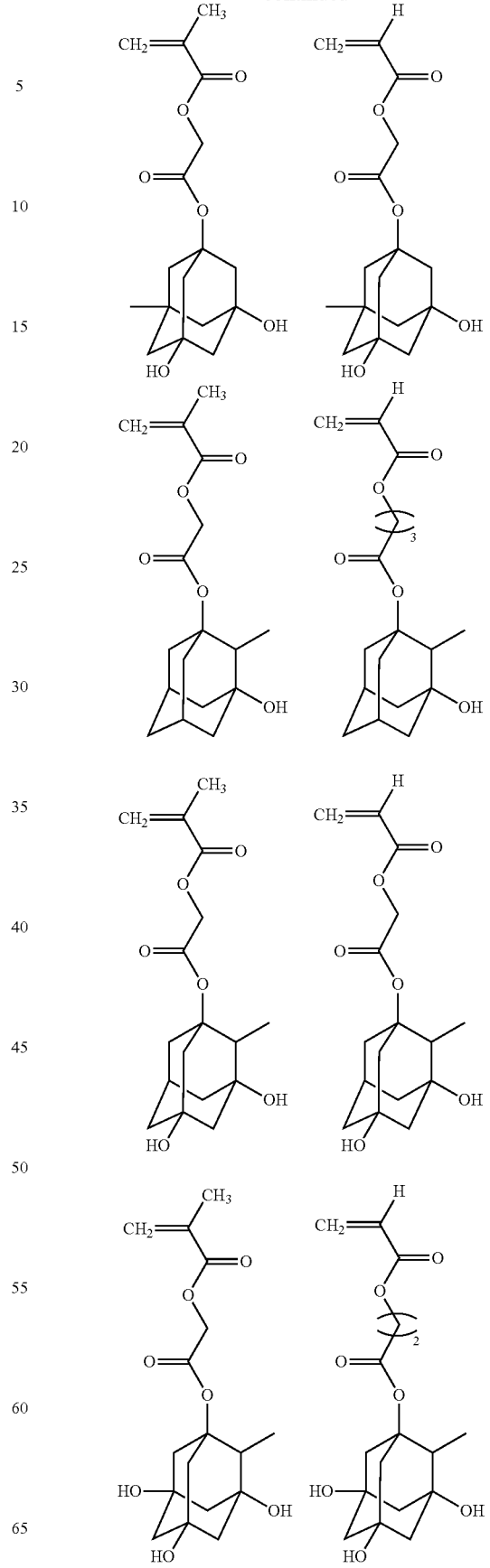

When the resin contains the structural unit derived from the monomer represented by the formula (a2-1), the content of the structural unit derived from the monomer represented by the formula (a2-1) is usually 3 to 95% by mole and preferably 5 to 40% by mole and more preferably 5 to 35% by mole based on total molar of all the structural units of the resin.

Examples of the lactone ring of the compound having no acid-labile group and having a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

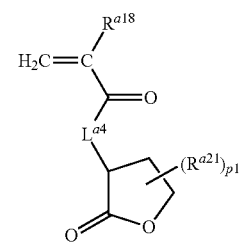
(a3-1)

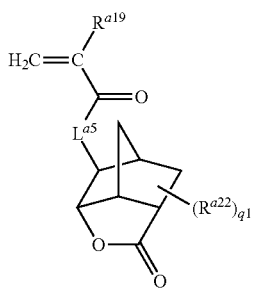
(a3-2)

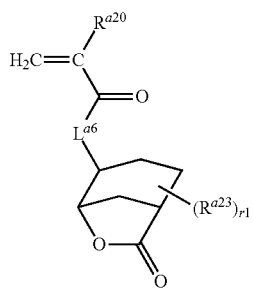
(a3-3)

wherein $L^{a4}$, $L^{a5}$ and $R^{a6}$ independently represent *—O— or *—O—$(CH_2)_{k3}$—CO—O— in which * represents a binding position to —CO— and 3 represents an integer of 1 to 7, $R^{a18}$, $R^{a19}$ and $R^{a20}$ independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the followings.

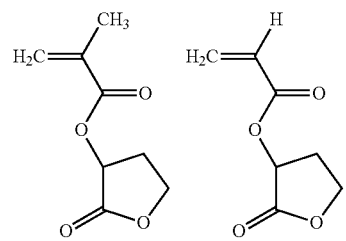

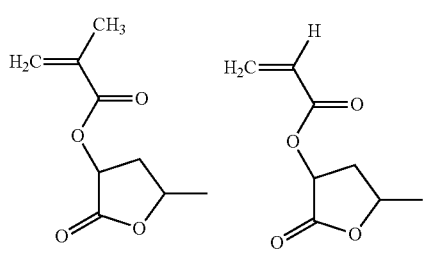

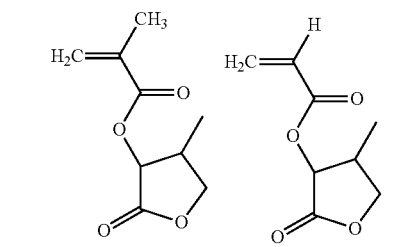

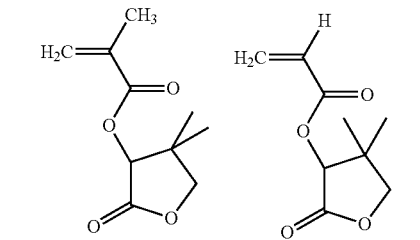

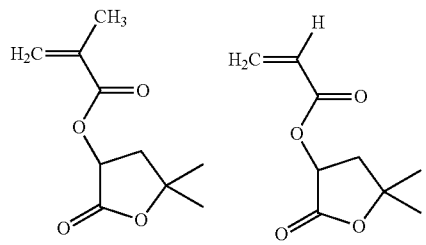

121
-continued
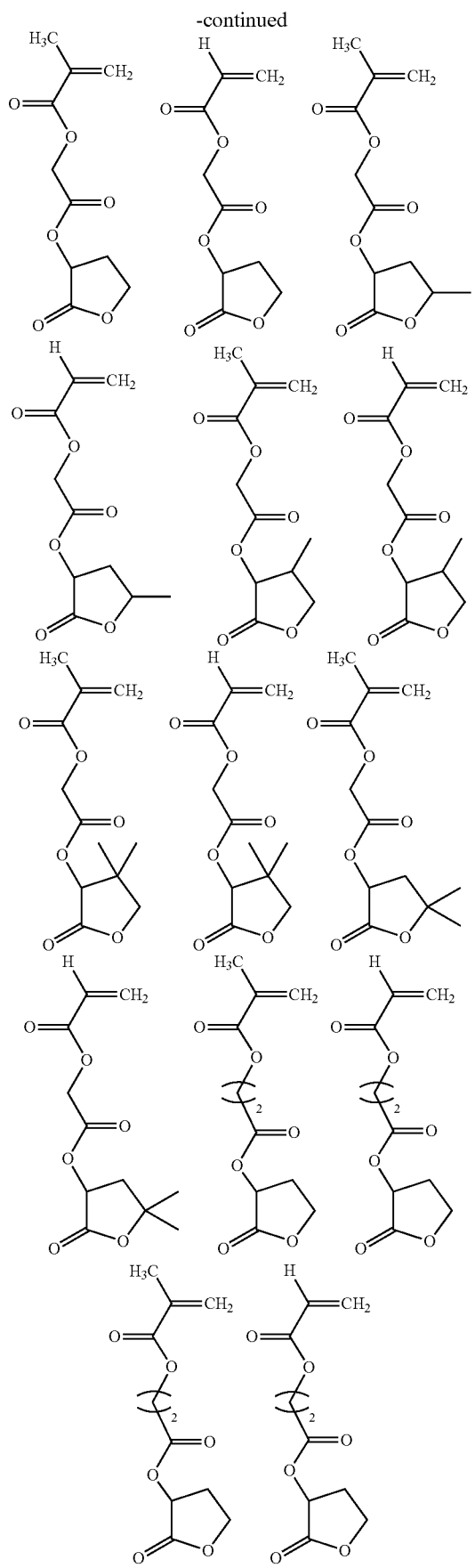
122
-continued
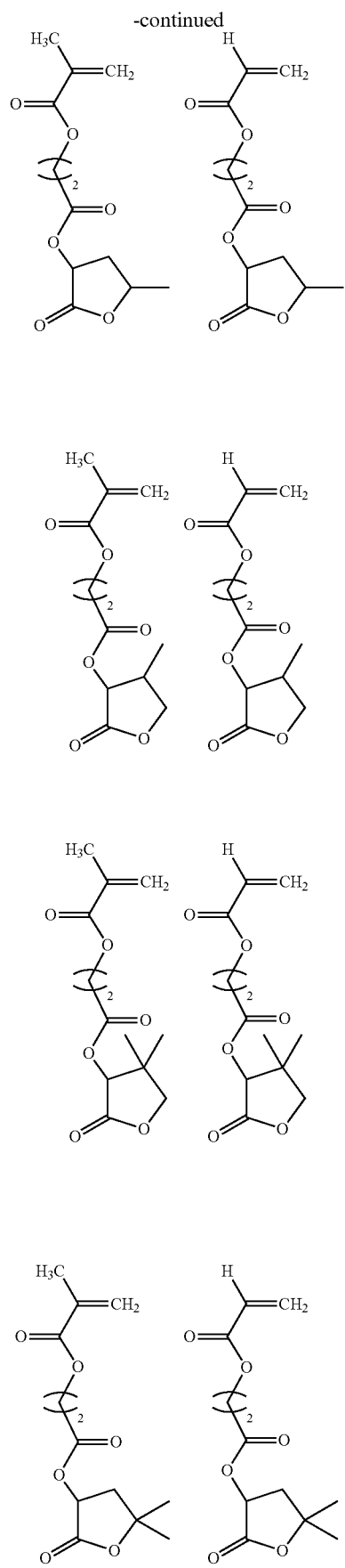

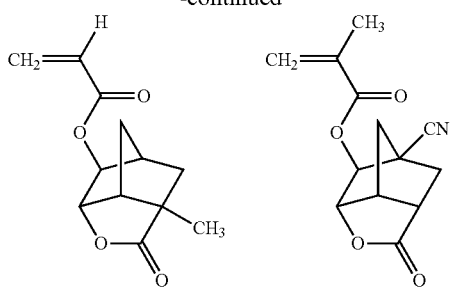
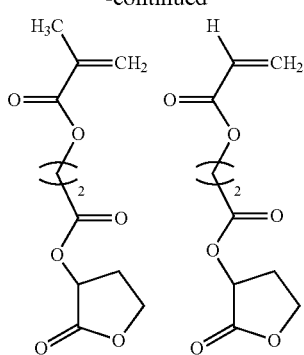
Examples of the monomer represented by the formula (a3-2) include the followings.
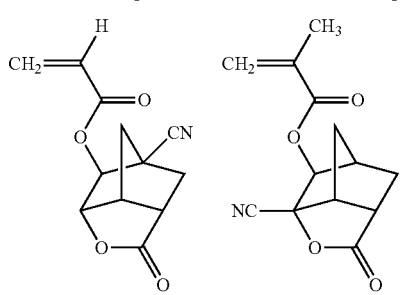
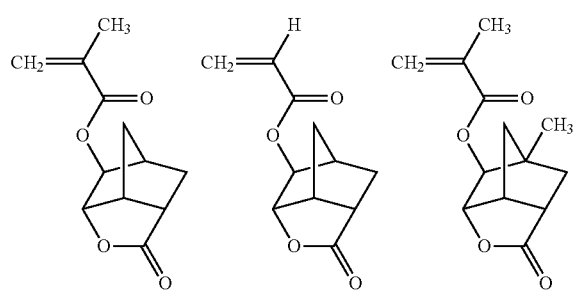
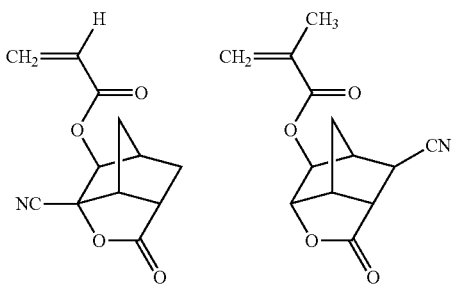
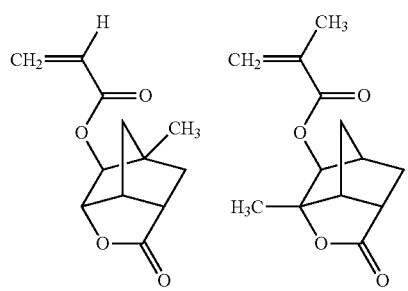
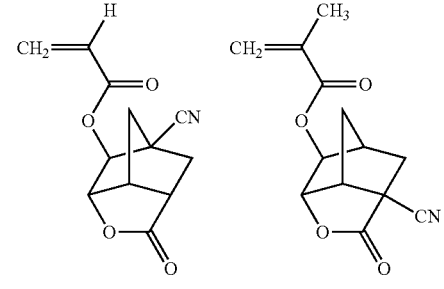
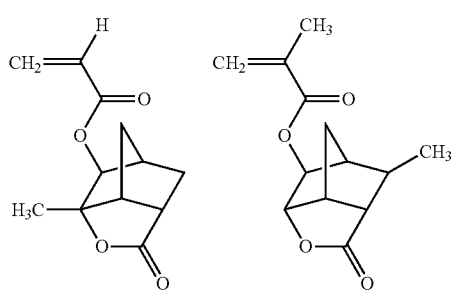
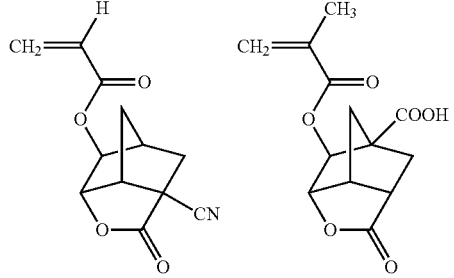
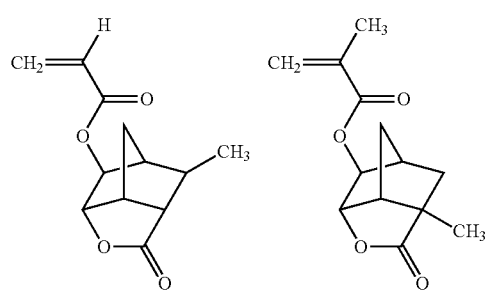
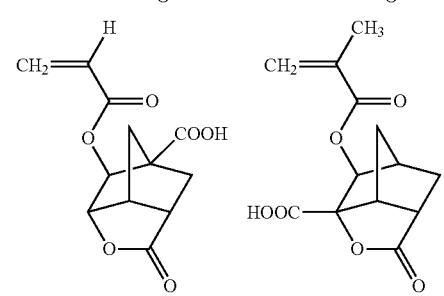

-continued
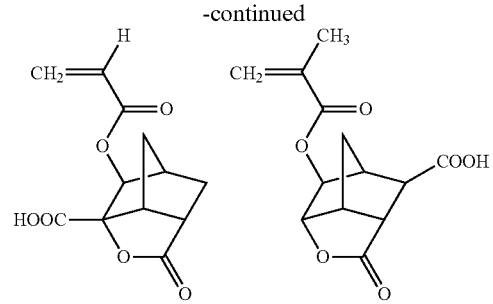
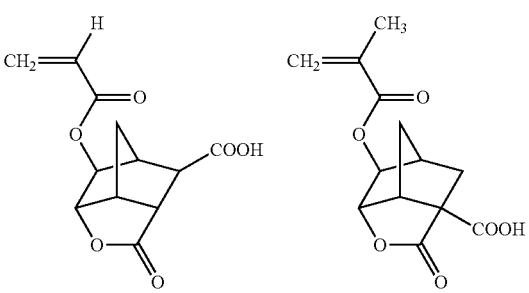
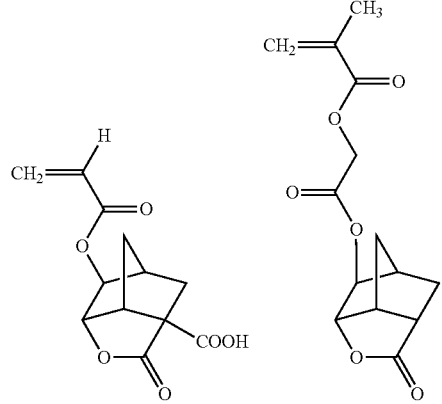
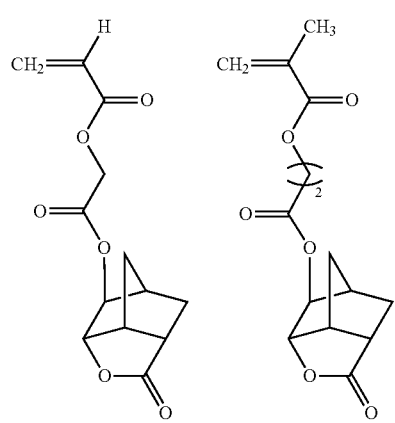
-continued
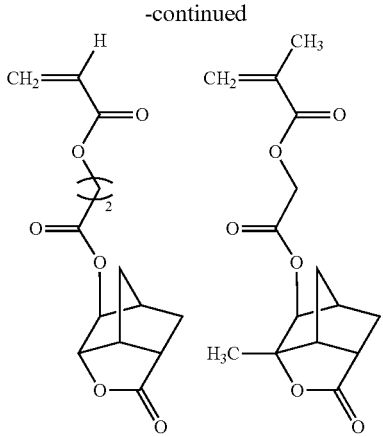
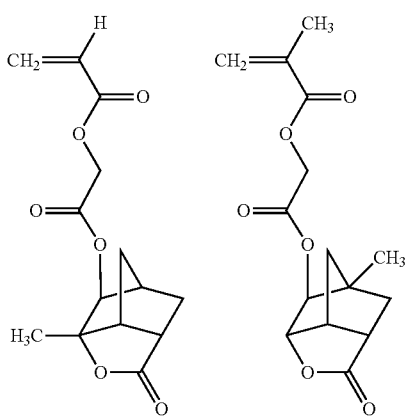
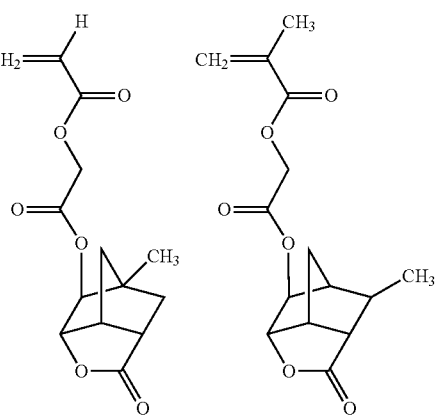
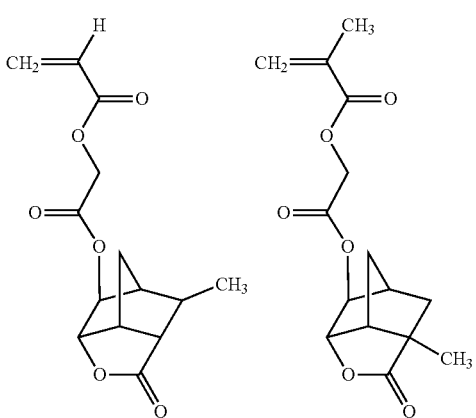

127
-continued
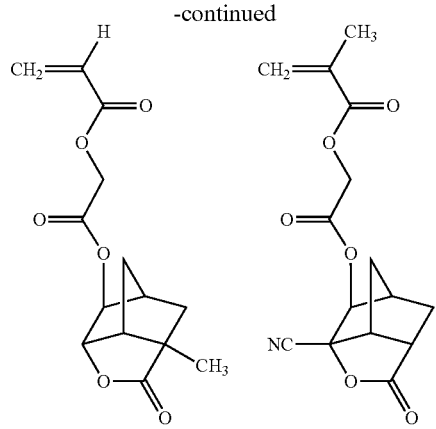
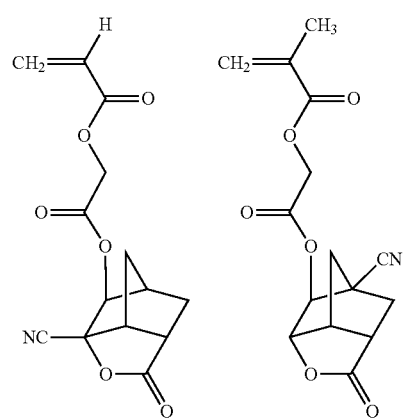
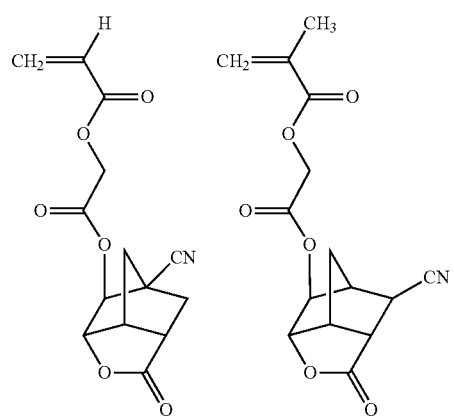
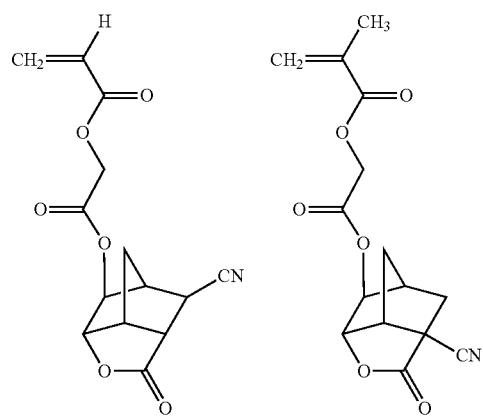
128
-continued
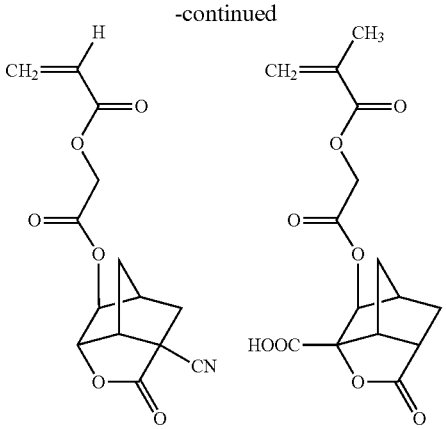
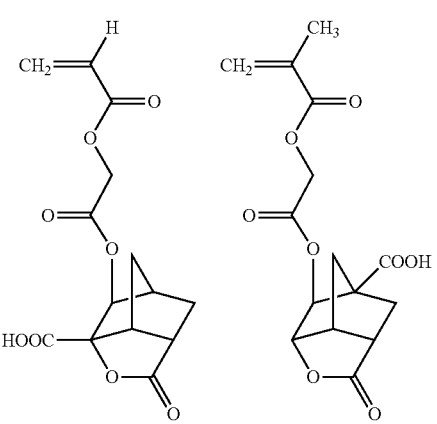
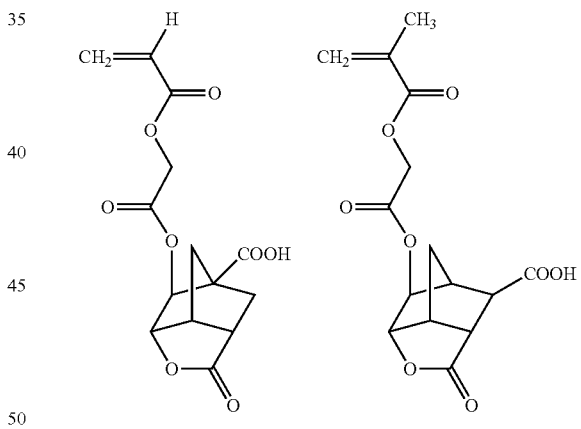
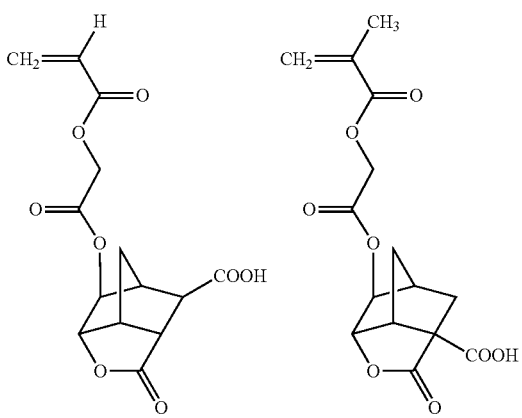

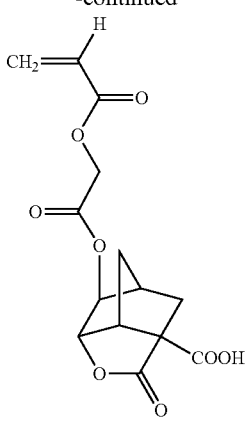
Examples of the monomer represented by the formula (a3-3) include the followings.
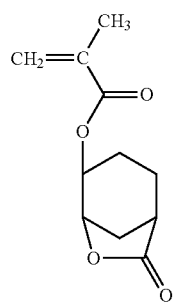 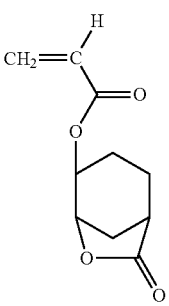 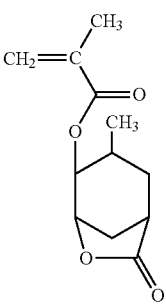
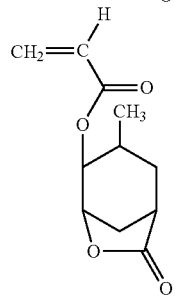 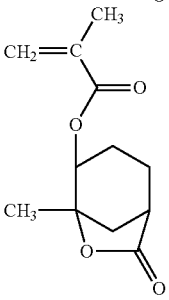 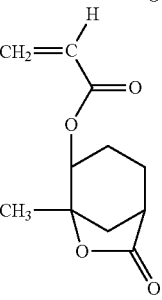
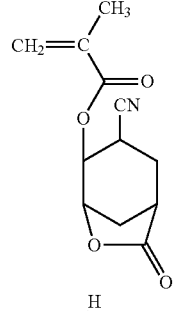 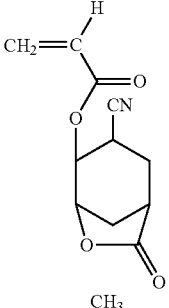 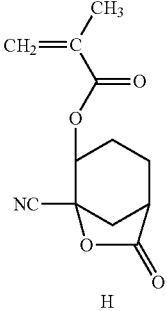
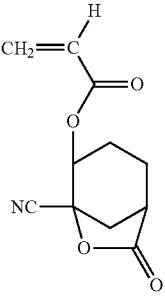 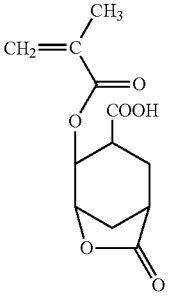 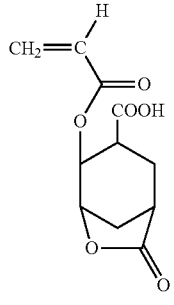
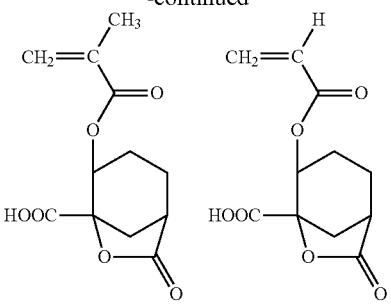
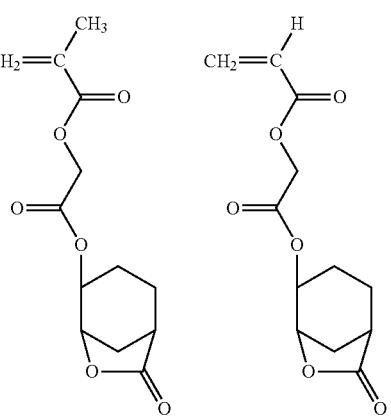
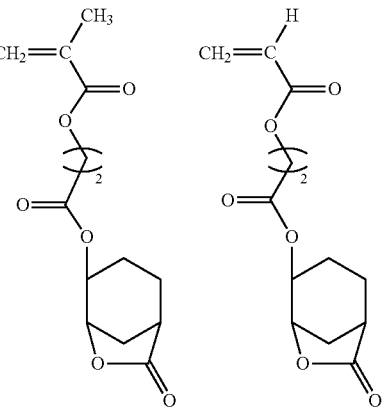
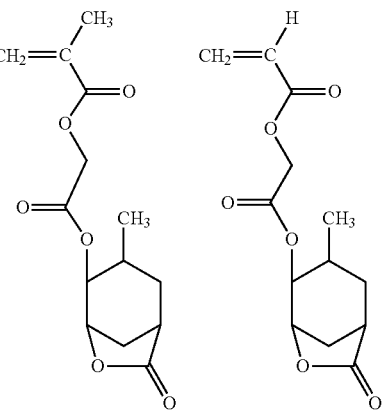

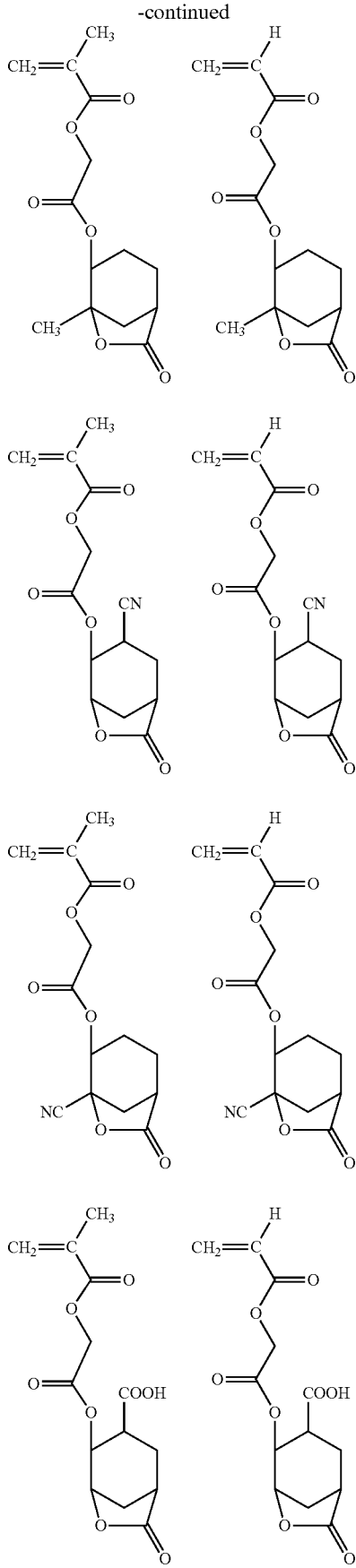
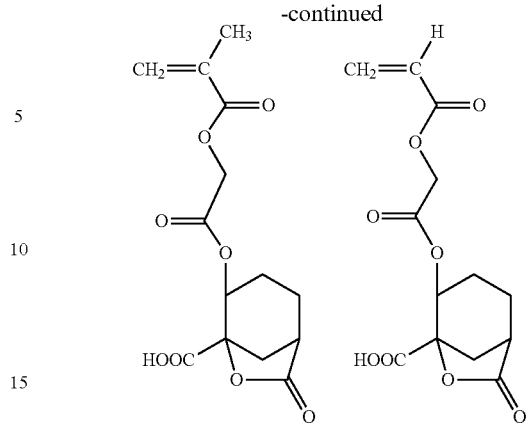

Among them, preferred are 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate, and more preferred are 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate.

When the resin contains the structural unit derived from the monomer having no acid-labile group and having a lactone ring, the content thereof is usually 5 to 70% by mole and preferably 10 to 65% by mole and more preferably 10 to 60% by mole based on total molar of all the structural units of the resin.

The resin can contain a structural unit derived from a monomer having an acid labile group containing a lactone ring. Examples of the monomer having an acid labile group containing a lactone ring include the followings.

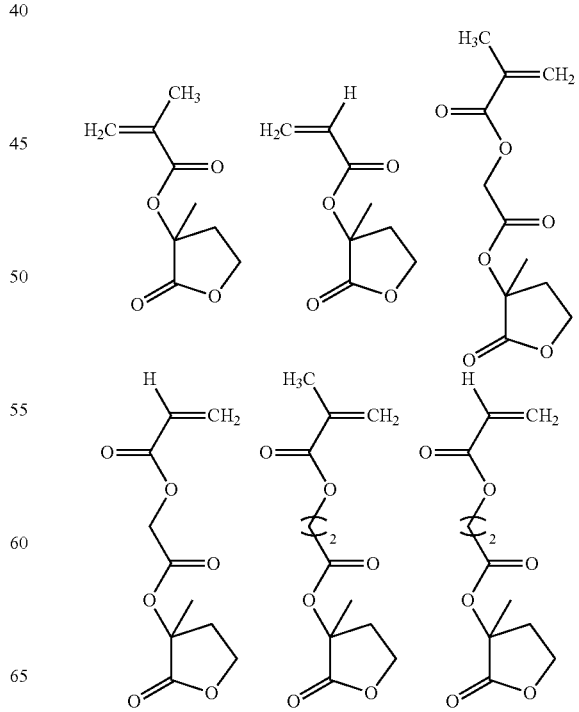

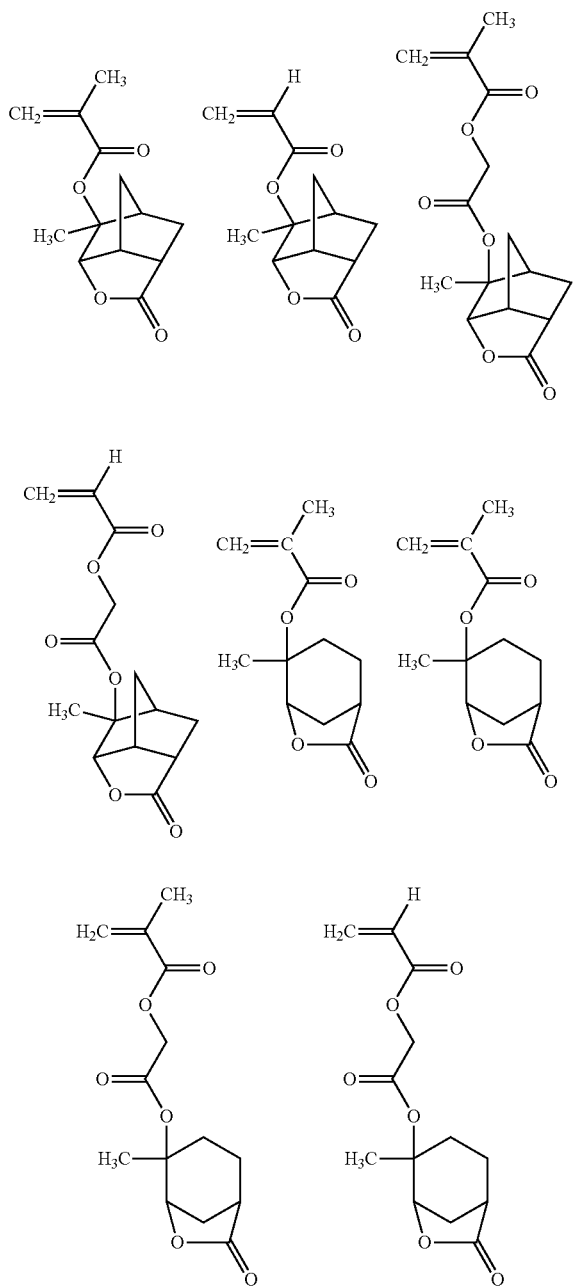

Examples of the other monomer having no acid-labile group include the monomers represented by the formulae (a4-1), (a4-2) and (a4-3):

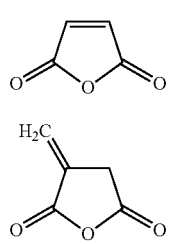

(a4-1)

(a4-2)

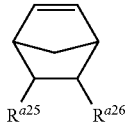

(a4-3)

wherein $R^{a25}$ and $R^{a26}$ independently represents a hydrogen atom, a C1-C3 aliphatic hydrocarbon group which can have one or more substituents, a carboxyl group, a cyano group or a —COOR$^{a27}$ group in which $R^{a27}$ represents a C1-C36 aliphatic hydrocarbon group or a C3-C36 saturated cyclic hydrocarbon group, and one or more —CH$_2$— in the C1-C36 aliphatic hydrocarbon group and the C3-C36 saturated cyclic hydrocarbon group can be replaced by —O— or —CO—, with the proviso that the carbon atom bonded to —O— of $R^{a27}$ of —COOR$^{a27}$ is not a tertiary carbon atom, or $R^{a25}$ and $R^{a26}$ are bonded together to form a carboxylic anhydride residue represented by —C(=O)OC(=O)—.

Examples of the substituent of the C1-C3 aliphatic hydrocarbon group include a hydroxyl group. Examples of the C1-C3 aliphatic hydrocarbon group which can have one or more substituents include a C1-C3 alkyl group such as a methyl group, an ethyl group and a propyl group, and a C1-C3 hydroxyalkyl group such a hydroxymethyl group and a 2-hydroxyethyl group. The C1-C36 aliphatic hydrocarbon group represented by $R^5$ is preferably a C1-C8 aliphatic hydrocarbon group and is more preferably a C1-C6 aliphatic hydrocarbon group. The C3-C36 saturated cyclic hydrocarbon group represented by $R^{25}$ is preferably a C4-C36 saturated cyclic hydrocarbon group, and is more preferably C4-C12 saturated cyclic hydrocarbon group. Examples of $R^{25}$ include a methyl group, an ethyl group, a propyl group, a 2-oxo-oxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a4-1), (a4-2) or (a4-3), the content thereof is usually 2 to 40% by mole and preferably 3 to 30% by mole and more preferably 5 to 20% by mole based on total molar of all the structural units of the resin.

Preferable resin is a resin containing the structural units derived from the monomer having an acid-labile group, and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, and preferably 3,000 or more of the weight-average molecular weight. The resin usually has 50,000 or less of the weight-average molecular weight, and preferably has 30,000 or less of the weight-average molecular weight. The weight-average molecular weight can be measured with gel permeation chromatography.

The content of the resin is usually 80% by weight or more in the solid component. In this specification, "solid component" means components other than solvents in the photoresist composition. The content of the solid component can be analyzed with conventional means such as liquid chromatography and gas chromatography.

The photoresist composition of the present invention can contain a basic compound as a quencher.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

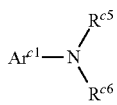

(C2)

wherein $Ar^{c1}$ represents an aromatic hydrocarbon group, and $R^{c5}$ and $R^{c6}$ each independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

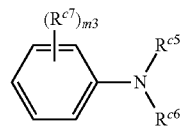

(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

(C3)

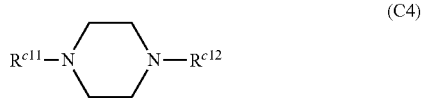

(C4)

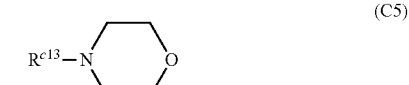

(C5)

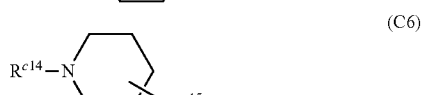

(C6)

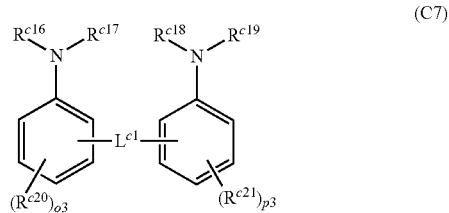

(C7)

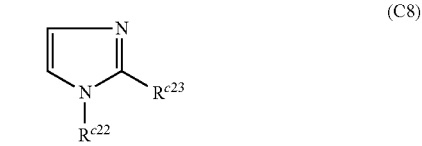

(C8)

(C9)

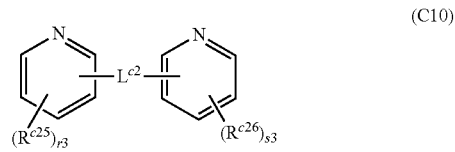

(C10)

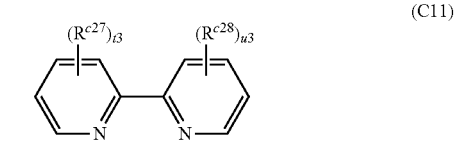

(C11)

wherein $R^{c8}$, $R^{c20}$, $R^{c21}$, and $R^{c23}$ to $R^{c28}$ each independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c66}$ each independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ each independently represents a divalent aliphatic hydrocarbon group, —CO—, —C(=NH)—, —C(=N$R^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the basic compound is used, the amount of the basic compound is usually 0.01 to 1 parts by weight per 100 parts by weight of solid component.

The photoresist composition of the present invention usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist composition of the present invention can contain, if necessary, a small amount of various additives such as a sensitizer, a dissolution inhibitor, other polymers, a surfactant, a stabilizer and a dye as long as the effect of the present invention is not prevented.

The photoresist composition of the present invention is useful for a chemically amplified photoresist composition.

A photoresist pattern can be produced by the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μl of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for ArF immersion lithography, EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: tetrahydrofuran, Flow rate: 1.0 mL/min., Detector: RI detector, Column temperature: 40° C., Injection volume: 100 μL] using standard polystyrene as a standard reference material available from TOSOH CORPORATION.

Example 1

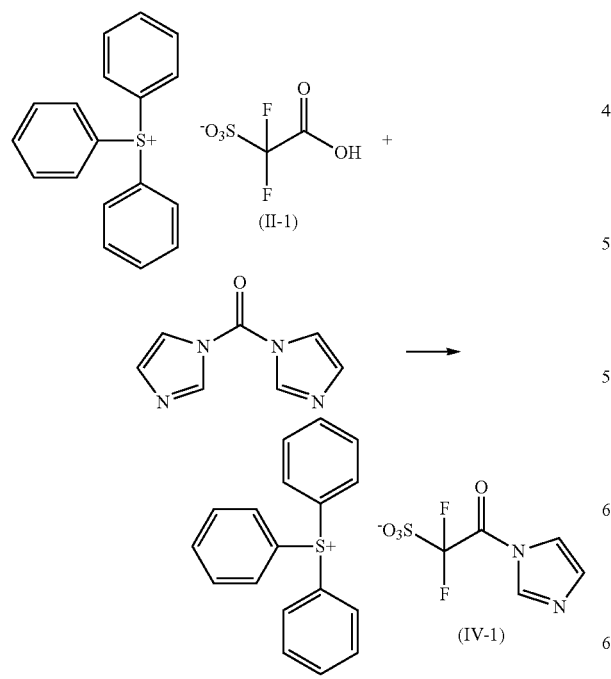

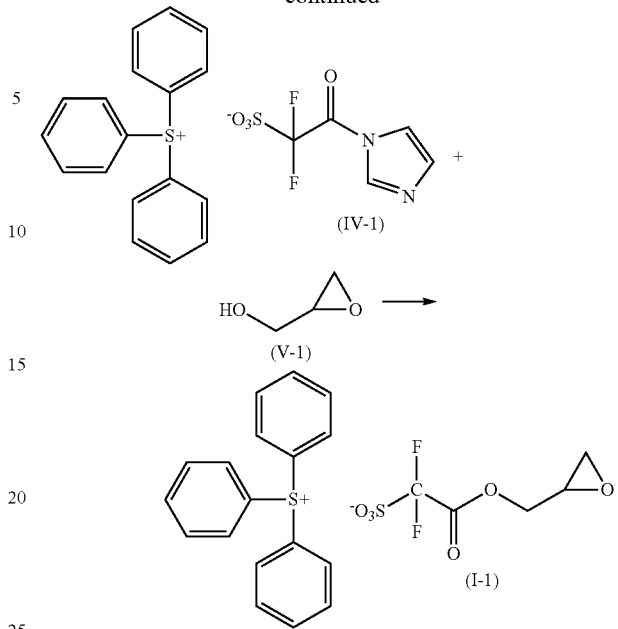

The salt represented by the formula (II-1) was prepared according to the method described in JP 2008-127367 A. A mixture of 10.00 parts of the salt represented by the formula (II-1), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 59.68 parts of a solution containing the salt represented by the formula (IV-1).

A mixture of 59.68 parts of a solution containing the salt represented by the formula (IV-1) and 1.64 parts of glycidol which was available from Aldrich was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 5.80 parts of a salt represented by the formula (I-1). This is called as Salt MS (ESI(+) Spectrum): M+ 263.1

MS (ESI(−) Spectrum): M− 231.0

Example 2

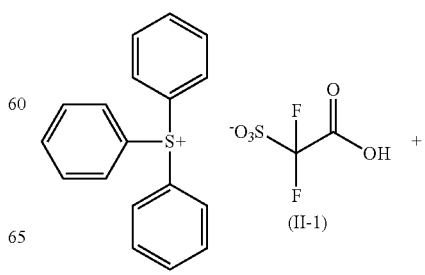

141
-continued

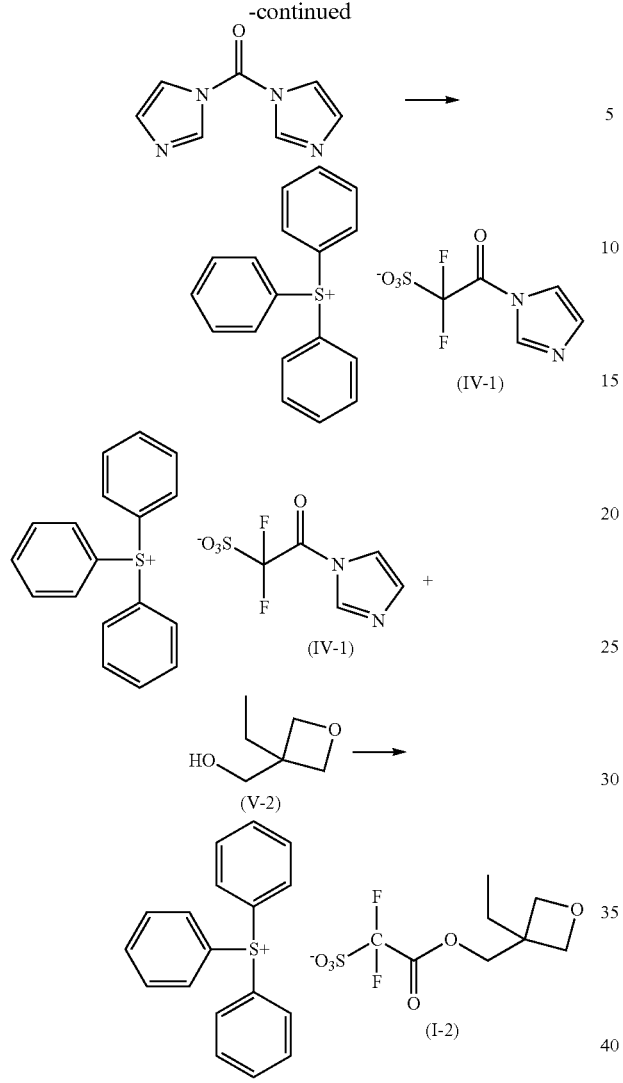

(IV-1)

(V-2)

(I-2)

142

Example 3

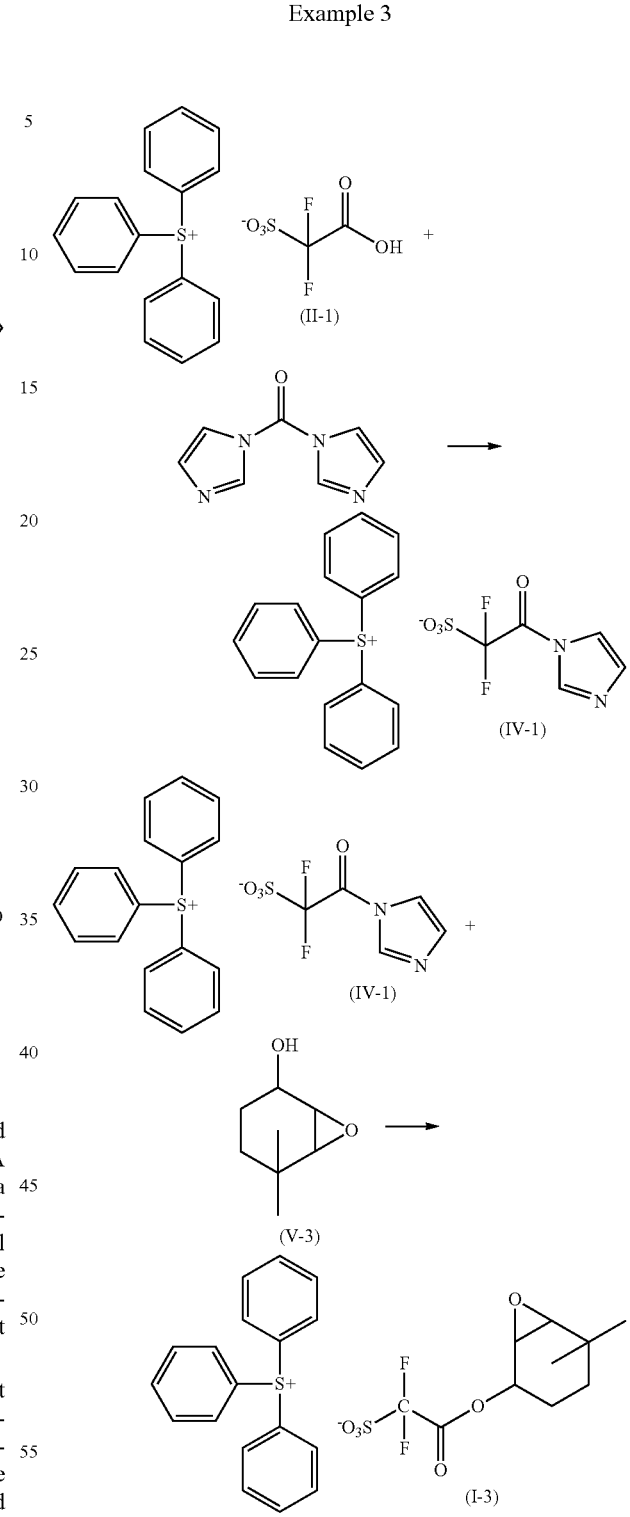

(II-1)

(IV-1)

(IV-1)

(V-3)

(I-3)

The salt represented by the formula (II-1) was prepared according to the method described in JP 2008-127367 A. A mixture of 10.00 parts of the salt represented by the formula (II-1), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 59.48 parts of a solution containing the salt represented by the formula (IV-1).

A mixture of 59.48 parts of a solution containing the salt represented by the formula (IV-1) and 2.57 parts of (3-ethyloxetane)methanol which was available from Tokyo Chemical Industry Co., Ltd. was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 8.73 parts of a salt represented by the formula (I-2). This is called as Salt I2.

MS (ESI(+) Spectrum): $M^+$ 263.1

MS (ESI(−) Spectrum): $M^+$ 273.0

The salt represented by the formula (II-1) was prepared according to the method described in JP 2008-127367 A. A mixture of 10.00 parts of the salt represented by the formula (II-1), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 59.88 parts of a solution containing the salt represented by the formula (IV-1).

A mixture of 59.88 parts of a solution containing the salt represented by the formula (IV-1) and 3.15 parts of 5,5-dimethyl-7-oxabicyclo[4.1.0]pentan-2-one which was available from Aldrich was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 5.42 parts of a salt represented by the formula (I-3). This is called as Salt I3.

MS (ESI (+) Spectrum): M$^+$263.1

MS (ESI(−) Spectrum): M$^-$ 299.0

Example 4

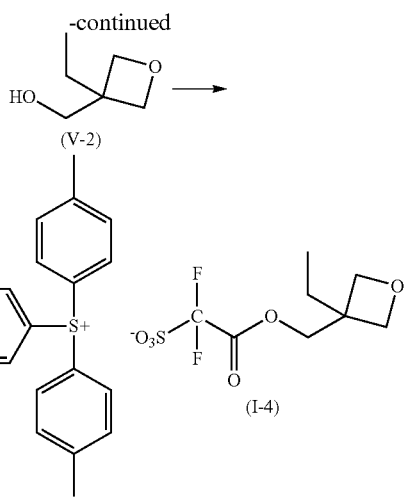

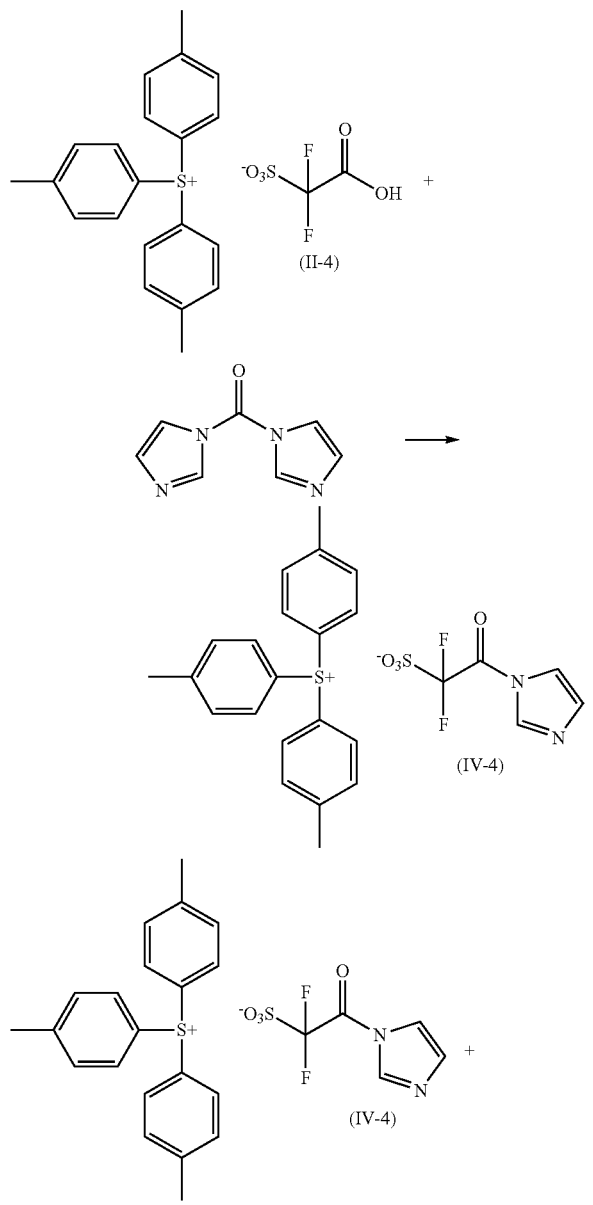

A mixture of 10.96 parts of the salt represented by the formula (II-4), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 60.54 parts of a solution containing the salt represented by the formula (IV-4).

A mixture of 60.54 parts of a solution containing the salt represented by the formula (IV-4) and 2.57 parts of (3-ethyloxetane)methanol which was available from Tokyo Chemical Industry Co., Ltd. was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 8.92 parts of a salt represented by the formula (I-4). This is called as Salt I4.

MS (ESI(+) Spectrum): M$^+$ 305.1

MS (ESI(−) Spectrum): M$^-$ 273.0

Example 5

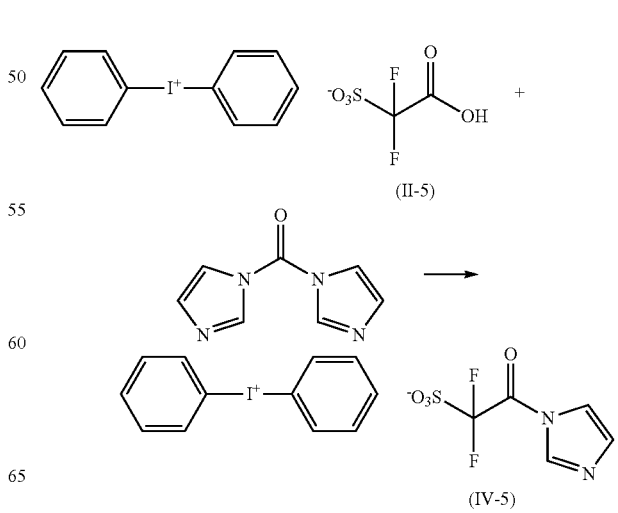

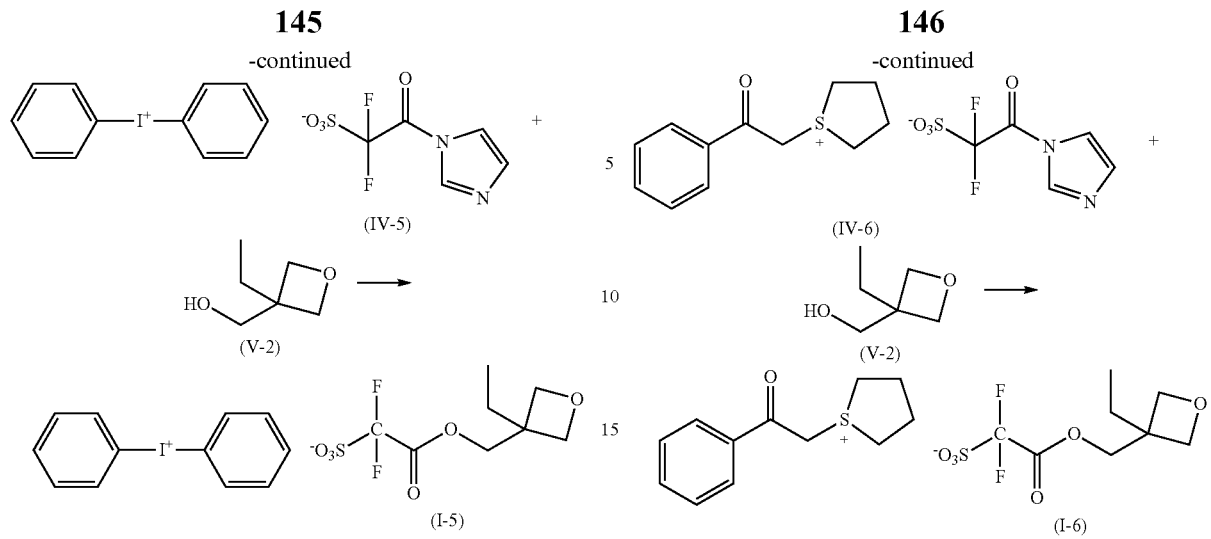

A mixture of 10.40 parts of the salt represented by the formula (II-5), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 59.98 parts of a solution containing the salt represented by the formula (IV-5).

A mixture of 59.98 parts of the solution containing the salt represented by the formula (IV-5) and 2.57 parts of (3-ethyloxetane)methanol which was available from Tokyo Chemical Industry Co., Ltd. was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 7.24 parts of a salt represented by the formula (I-5). This is called as Salt I5.

MS (ESI(+) Spectrum): M$^+$ 281.0

MS (ESI(−) Spectrum): M$^−$ 273.0

A mixture of 8.72 parts of the salt represented by the formula (II-6), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 58.24 parts of a solution containing the salt represented by the formula (IV-6).

A mixture of 58.24 parts of the solution containing the salt represented by the formula (IV-6) and 2.57 parts of (3-ethyloxetane)methanol which was available from Tokyo Chemical Industry Co., Ltd. was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 5.98 parts of a salt represented by the formula (I-6). This is called as Salt I6.

MS (ESI(+) Spectrum): M$^+$ 207.1

MS (ESI(−) Spectrum): M$^−$ 273.0

Monomers used in Resin Synthesis Examples are following monomers (A), (B), (C), (D), (E) and (F).

Example 6

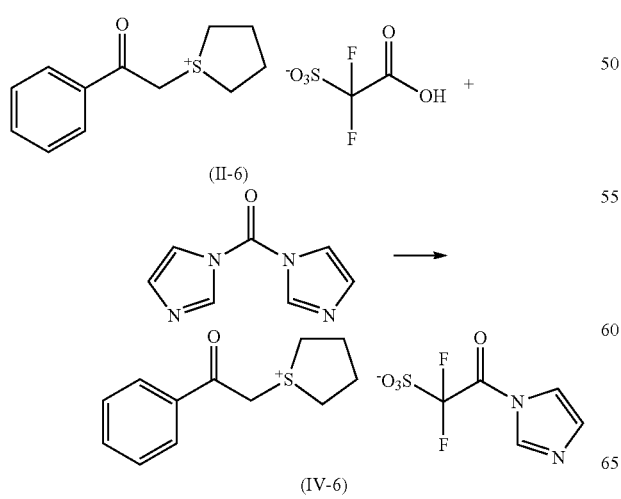

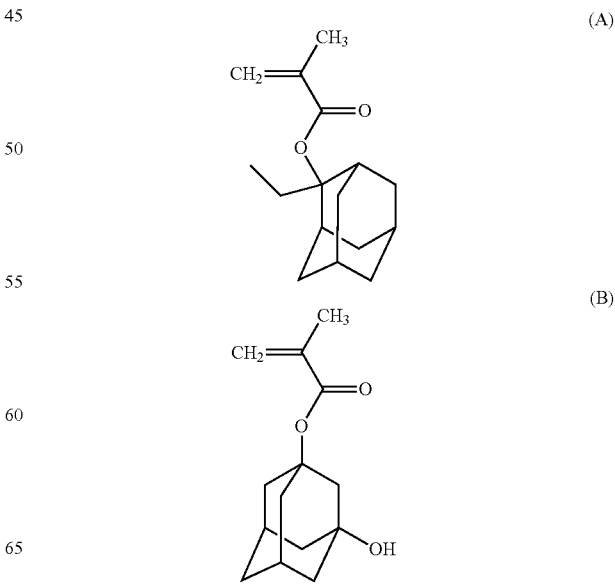

(C)

(D)

(E)

(F)

Resin Synthesis Example 1

The monomers (D), (E), (B), (C) and (F) were mixed in a molar ratio of 30/14/6/20/30 (monomer (D)/monomer (E)/ monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1.00 mol % based on all monomer molar amount and azobis(2,4-dimethylvaleronitrile) as an initiator in a ratio of 3.00 mol % based on all monomer molar amount were added, and the obtained mixture was heated at 73° C. for about 5 hours. The reaction mixture obtained was poured into a mixture of a large amount of methanol and water (methanol/water weight ratio=4/1) to cause precipitation, and this operation was further repeated twice for purification. As a result, a resin having a weight-average molecular weight of about $8.1 \times 10^3$ was obtained in a yield of 65%. The resin had the following structural units. This is called as resin A1.

Resin Synthesis Example 2

The monomers (A), (B) and (C) were mixed in a molar ratio of 50/25/25 (monomer (A)/monomer (B)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 77° C. for about 5 hours. The reaction mixture obtained was poured into a mixture of a large amount of methanol and water (methanol/water weight ratio=3/1) to cause precipitation, and this operation was further repeated three times for purification. As a result, a resin having a weight-average molecular weight of about $8.0 \times 10^3$ was obtained in a yield of 60%. The resin had the following structural units. This is called as resin A2.

-continued

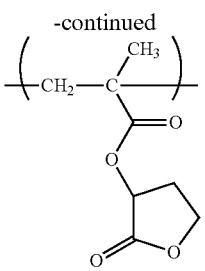

Examples 7 to 18 and Comparative Example 1

Resin

Resin A1, A2
<Acid Generator>
Acid Generator I1: Salt I1
Acid Generator I2: Salt I2
Acid Generator I3: Salt I3
Acid Generator I4: Salt I4
Acid Generator I5: Salt I5
Acid Generator I6: Salt I6
Acid Generator B1:

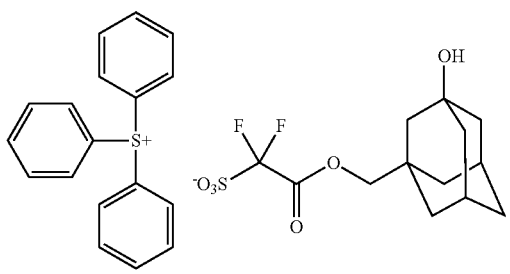

Acid Generator B2:

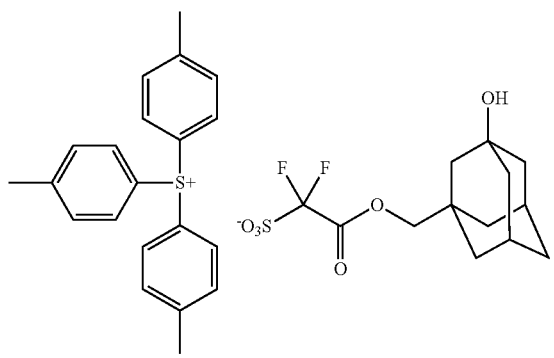

Acid Generator B3:

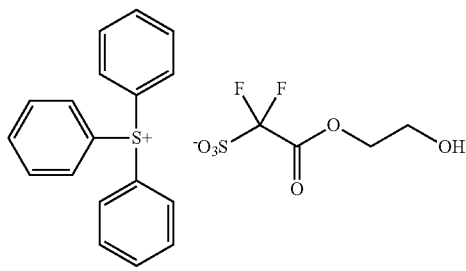

<Quencher>
C1: 2,6-diisopropylaniline

<Solvent>

| Y1: | propylene glycol monomethyl ether acetate | 265 parts |
| | 2-heptanone | 20 parts |
| | propylene glycol monomethyl ether | 20 parts |
| | γ-butyrolactone | 3.5 parts |

The following components were mixed and dissolved, further, filtrated through a fluorine resin filter having pore diameter of 0.2 μm, to prepare photoresist compositions.
Resin (kind and amount are described in Table 1)
Acid generator (kind and amount are described in Table 1)
Quencher (kind and amount are described in Table 1)
Solvent Y1

TABLE 1

| Ex. No. | Resin (kind/amount (part)) | Acid generator (kind/amount (part)) | Quencher (kind/amount (part)) | PB (° C.) | PEB (° C.) |
| --- | --- | --- | --- | --- | --- |
| Ex. 7 | A1/10 | I1/0.50 | C1/0.07 | 100 | 100 |
| Ex. 8 | A2/10 | I1/0.50 | C1/0.07 | 110 | 110 |
| Ex. 9 | A1/10 | I1/0.10 B2/0.70 | C1/0.07 | 100 | 100 |
| Ex. 10 | A1/10 | I1/0.10 B1/0.60 | C1/0.07 | 100 | 100 |
| Ex. 11 | A1/10 | I2/0.50 | C1/0.07 | 100 | 100 |
| Ex. 12 | A1/10 | I2/0.10 B2/0.70 | C1/0.07 | 100 | 100 |
| Ex. 13 | A1/10 | I3/0.50 | C1/0.07 | 100 | 100 |
| Ex. 14 | A1/10 | I3/0.10 B2/0.70 | C1/0.07 | 100 | 100 |
| Ex. 15 | A1/10 | I2/0.80 B2/0.80 | C1/0.07 | 100 | 100 |
| Ex. 16 | A1/10 | I4/0.80 B2/0.80 | C1/0.07 | 100 | 100 |
| Ex. 17 | A1/10 | I5/0.80 B2/0.80 | C1/0.07 | 100 | 100 |
| Ex. 18 | A1/10 | I6/0.80 B2/0.80 | C1/0.07 | 100 | 100 |
| Comp. Ex. 1 | A2/10 | B3/0.50 | C1/0.07 | 100 | 100 |

Silicon wafers having a diameter of 12 inches were each coated with "ARC-29", which is an organic anti-reflective coating composition available from Nissan Chemical Industries, Ltd., and then baked at 205° C. for 60 seconds, to form a 780 Å-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in a column of "PB" in Table 1 for 60 seconds. Using an ArF excimer stepper for immersion exposure ("XT: 1900Gi" manufactured by ASML, NA=1.35, ¾ Annular, X-Y polarization), each wafer thus formed with the respective resist film was subjected to line and space pattern immersion exposure, with the exposure quantity being varied stepwise.

After the exposure, each wafer was subjected to post-exposure baking on a hotplate at a temperature shown in column of "PEB" in Table 1 for 60 seconds and then to paddle development for 60 seconds with an aqueous solution of 2.38 wt % tetramethylammonium hydroxide.

Each of photoresist patterns developed on the organic anti-reflective coating substrate after the development was observed with a scanning electron microscope, the results of which are shown in Table 2.

Effective Sensitivity (ES): It is expressed as the amount of exposure that 50 nm line pattern and the space pattern become 1:1 after exposure and development.

Line Edge Roughness (LER): The photoresist pattern was observed with a scanning electron microscope, and the difference between the height of the highest point and height of the lowest point of the scabrous wall surface of the photoresist pattern was measured. When the difference is 4.5 nm or less, LER is very good and its evaluation is marked by "⊚", when the difference is more than 4.5 nm and 5 nm or less, LER is very good and its evaluation is marked by "○", and when the difference is more than 5 nm, LER is bad and its evaluation is marked by "X". The smaller the difference is, the better the photopattern is. The difference obtained was also shown in parentheses in Table 2.

TABLE 2

| Ex. No. | LER |
|---|---|
| Ex. 7 | ○ (4.68) |
| Ex. 8 | ○ (4.94) |
| Ex. 9 | ⊚ (3.44) |
| Ex. 10 | ⊚ (3.84) |
| Ex. 11 | ○ (4.52) |
| Ex. 12 | ⊚ (3.38) |
| Ex. 13 | ○ (4.53) |
| Ex. 14 | ⊚ (3.65) |
| Ex. 15 | ⊚ (3.34) |
| Ex. 16 | ⊚ (3.29) |
| Ex. 17 | ○ (4.51) |
| Ex. 18 | ⊚ (3.82) |
| Comp. Ex. 2 | X (6.24) |

The salt of the present invention is novel and is suitable for an acid generator, and the photoresist composition of the present invention provides a photoresist pattern having good line edge roughness.

What is claimed is:

1. A salt represented by the formula (I):

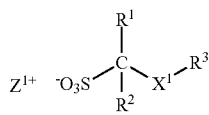

wherein $R^1$ and $R^2$ each independently represent a fluorine atom or a C1-C6 perfluoroalkyl group, $X^1$ represents a C1-C17 divalent saturated hydrocarbon group which can have one or more fluorine atoms and in which one or more —$CH_2$— can be replaced by —O— or —CO—, $R^3$ represents a structure containing an oxirane or oxetane ring, and $Z^{1+}$ represents an organic cation.

2. The salt according to claim 1, wherein $R^3$ represents a group represented by the formula (IA) or (IE):

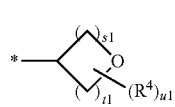

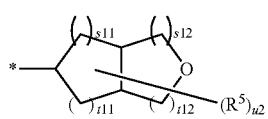

wherein $R^4$ is independently in each occurrence a C1-C12 saturated hydrocarbon group or a C6-C18 aromatic hydrocarbon group, and the saturated hydrocarbon group and the aromatic hydrocarbon group can have one or more substituents selected from the group consisting of a C1-C6 alkyl group and a nitro group, and one or more —$CH_2$— in the saturated hydrocarbon group can be replaced by —O—, u1 represents an integer of 0 to 8, s1 represents an integer of 1, t1 represents an integer of 0 to 1, $R^5$ is independently in each occurrence a hydroxyl group, a halogen atom, a C1-C6 alkyl group, a C1-C6 alkoxy group, a C1-C6 hydroxyalkyl group, a C2-C7 acyl group, a C2-C7 acyloxy group or a C2-C7 acylamino group, and two of $R^5$ can be bonded to each other to form a single bond or a ring, u2 represents an integer of 0 to 16, s11 represents an integer of 1 to 4, t11 represents an integer of 0 to 2, s12 represents an integer of 1 to 4, t12 represents an integer of 0, and * represents a binding position to —$X^1$—.

3. The salt according to claim 1, wherein the salt represented by the formula (I) is a salt represented by the formula (II):

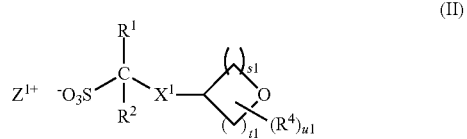

wherein $R^1$, $R^2$, $R^4$, $X^1$, s1, t1, u1 and $Z^{1+}$ are the same as defined above.

4. The salt according to claim 1, wherein $X^1$ is *—CO—O—$CH_2$— in which * represents a binding position to —$C(R^1)(R^2)$—.

5. The salt according to claim 1, wherein $Z^{1+}$ is a triarylsulfonium cation.

6. An acid generator comprising the salt according to claim 1.

7. A photoresist composition comprising the acid generator according to claim 6 and a resin.

8. The photoresist composition according to claim 7, wherein the resin comprises a structural unit having an acid-labile group, being insoluble or poorly soluble in an aqueous alkali solution but becoming soluble in an aqueous alkali solution by the action of an acid.

9. The photoresist composition according to claim 7 or 8, which further contains a basic compound.

10. A process for producing a photoresist pattern comprising the following steps (1) to (5):
(1) a step of applying the photoresist composition according to claim 7 or 8 on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

* * * * *